US011697682B2

(12) United States Patent
Mendel et al.

(10) Patent No.: US 11,697,682 B2
(45) Date of Patent: Jul. 11, 2023

(54) MOTILE SPERM DOMAIN CONTAINING PROTEIN 2 ANTIBODIES AND METHODS OF USE THEREOF

(71) Applicant: VASCULAR BIOGENICS LTD., Modiin (IL)

(72) Inventors: Itzhak Mendel, Rehovot (IL); Niva Yacov, Tel Aviv (IL); Erez Feige, Hemed (IL); Eyal Breitbart, Hashmona'im (IL)

(73) Assignee: VASCULAR BIOGENICS LTD., Modiin (IL)

(*) Notice: Subject to any disclaimer, the term of this patent is extended or adjusted under 35 U.S.C. 154(b) by 0 days.

(21) Appl. No.: 17/470,766

(22) Filed: Sep. 9, 2021

(65) Prior Publication Data

US 2022/0127342 A1     Apr. 28, 2022

Related U.S. Application Data

(60) Provisional application No. 63/167,317, filed on Mar. 29, 2021, provisional application No. 63/076,697, filed on Sep. 10, 2020.

(51) Int. Cl.
| | | |
|---|---|---|
| *A61K 39/00* | (2006.01) | |
| *A61K 39/395* | (2006.01) | |
| *C07K 16/00* | (2006.01) | |
| *C07K 16/46* | (2006.01) | |
| *C07H 21/04* | (2006.01) | |
| *C12N 5/02* | (2006.01) | |
| *C12N 5/20* | (2006.01) | |
| *C12N 15/00* | (2006.01) | |
| *C07K 16/18* | (2006.01) | |
| *A61P 37/00* | (2006.01) | |
| *A61P 1/00* | (2006.01) | |
| *A61P 25/00* | (2006.01) | |
| *A61P 29/00* | (2006.01) | |
| *A61P 35/04* | (2006.01) | |
| *A61K 45/06* | (2006.01) | |

(52) U.S. Cl.
CPC .............. *C07K 16/18* (2013.01); *A61K 45/06* (2013.01); *A61P 1/00* (2018.01); *A61P 25/00* (2018.01); *A61P 29/00* (2018.01); *A61P 35/04* (2018.01); *A61P 37/00* (2018.01); *A61K 2039/505* (2013.01)

(58) Field of Classification Search
None
See application file for complete search history.

(56) References Cited

U.S. PATENT DOCUMENTS

| | | |
|---|---|---|
| 2004/0171009 A1 | 9/2004 | Tang et al. |
| 2008/0089891 A1 | 4/2008 | Hahn et al. |
| 2009/0137687 A1 | 5/2009 | Chaplin |
| 2011/0015865 A1 | 1/2011 | Rosenberg et al. |
| 2011/0257034 A1 | 10/2011 | Barany et al. |
| 2012/0020954 A1 | 1/2012 | Achiron et al. |
| 2014/0128277 A1 | 5/2014 | Moller et al. |
| 2018/0214543 A1 | 8/2018 | Mendel et al. |
| 2019/0040150 A1 | 2/2019 | Mendel et al. |
| 2019/0276561 A1 | 9/2019 | Takagi |
| 2019/0345256 A1* | 11/2019 | Chang .............. G01N 33/57488 |
| 2020/0181249 A1* | 6/2020 | Curtis ..................... A61P 13/12 |
| 2020/0407434 A1 | 12/2020 | Mendel et al. |
| 2021/0077622 A1 | 3/2021 | Mendel et al. |
| 2021/0095044 A1 | 4/2021 | Mendel et al. |

FOREIGN PATENT DOCUMENTS

| | | |
|---|---|---|
| JP | A-S63-096123 | 4/1988 |
| JP | A-H10-237093 | 9/1998 |
| JP | 2006-151902 A | 6/2006 |
| WO | WO-0187981 A2 | 11/2001 |
| WO | WO-03015494 A1 | 2/2003 |
| WO | WO-03053407 A1 | 7/2003 |
| WO | WO-2010052718 A1 | 5/2010 |
| WO | WO-2012016706 A1 | 2/2012 |
| WO | WO-2012121679 A1 | 9/2012 |
| WO | WO-2013/014405 A2 | 1/2013 |
| WO | WO-2013088245 A1 | 6/2013 |
| WO | WO-2013113615 A1 | 8/2013 |
| WO | WO-2014128185 A1 | 8/2014 |
| WO | WO-2016185016 A1 | 11/2016 |
| WO | WO-2018/088403 A1 | 5/2018 |
| WO | WO-2019/175806 A1 | 9/2019 |
| WO | WO-2019/195409 A1 | 10/2019 |
| WO | WO-2020/006486 A1 | 1/2020 |
| WO | WO-2020/069349 A1 | 4/2020 |

OTHER PUBLICATIONS

Brown et al. Tolerance of single, but not multiple, amino acid replacements in antibody VH CDR2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28. (Year: 2002).*
Rabia et al. Understanding and overcoming trade-offs between antibody affinity, specificity, stability and solubility. Biochem Eng J. Sep. 15, 2018; 137: 365-374. (Year: 2018).*
Yacov et al. MOSPD2 is a therapeutic target for the treatment of CNS inflammation. Clinical and Experimental Immunology, 201:105-120, 2020. (Year: 2020).*

(Continued)

*Primary Examiner* — Maher M Haddad
(74) *Attorney, Agent, or Firm* — Sterne, Kessler, Goldstein & Fox P.L.L.C.

(57) ABSTRACT

The present disclosure relates to antibodies or antigen binding fragments thereof that specifically bind to Motile Sperm Domain Containing Protein 2 (MOSPD2) and methods of using the same.

29 Claims, 28 Drawing Sheets

Specification includes a Sequence Listing.

(56) References Cited

OTHER PUBLICATIONS

Yacov et al. MOSPD2: a novel therapeutic target for the treatment of CNS inflammation. Multiple Sclerosis Journal, (Oct. 2018) vol. 24, No. 2, Supp. pp. 463-464. Abstract No. P871 (Year: 2018).*
Press Release. Publication by VBL therapeutics highlights MOSPD2 as a potential new target for breast cancer therapy. Golbenewswire. Jul. 10, 2018. p. 1. (Year: 2018).*
Al-Khamis, F.A., "The use of immune modulating drugs for the treatment of multiple sclerosis," *Neurosciences*, 21(1):4-9 (2016), Elsevier Publisher, Edinburgh, United Kingdom.
Beurger, K. "Functional Analysis of the MOSPD Gene Family," Thesis Presented for the Degree of Doctor of Philosophy, University of Edinburgh, 2010.
Bonatti, F., et al., "Genetic susceptibility to ANCA-associated vasculitis: state of the art," *Frontiers in Immunology*, 5:1-14 (2014), International Union of Immunological Societies, Berlin, Germany.
Dermer, G.B., "Another Anniversary for the War on Cancer," *Bio/Technology*, 12:320 (1994), Wiley Online Library, New Jersey, United States.
Freshney, R.I., "Culture of Animal Cells: A Manual of Basic Technique," Alan R. Liss, Inc., 1983, New York, United States, pp. 3-4.
Han, S.M., et al. "Sperm and Oocyte Communication Mechanisms Controlling *C. elegans* Fertility," *Dev. Dynamics* 239:1265-1281, 2010, Wiley-Liss, Inc., United States.
Hang, B., et al., "A Novel Peptide Isolated from a Phage Display Peptide Library with Trastuzumab Can Mimic Antigen Epitope HER-2," *J. Biol. Chem.*, 280:4656-4662 (2005), American Society for Biochemistry and Molecular Biology, Maryland, United States.
Khotskaya, Y.B., et al., "S6K1 promotes invasiveness of breast cancer cells in a model of metastasis of triple-negative breast cancer," Am. J. Transl. Res. 6(4):361-376, 2014, e-Century Publishing Corporation, Madison, Wisconsin, United States.
Mendel, I., et al., "Identification of Motile Sperm Domain-Containing Protein 2 as Regulator of Human Monocyte Migration," *J. Immunol.*, 198:2125-2132 (2017), American Association of Immunologists, Rockville, Maryland, United States.
Ru, Y., et al., "Transient receptor potential-canonical 3 modulates sperm motility and capacitation-associated protein tyrosine phosphorylation via [Ca2+]i mobilization," *Acta Biochim. Biophys. Sin. (Shanghai)* 47(6):404-413, 2015, Oxford Press, United Kingdom.
Salem, Y., et al., "Newly characterized motile sperm domain-containing protein 2 promotes human breast cancer metastasis," Int. J. Cancer, 144:125-135 (2019), John Wiley & Sons, Hoboken, New Jersey, United States.
Stancovski, I., et al., "Mechanistic aspects of the opposing effects of monoclonal antibodies to the ERBB2 receptor on tumor growth," *Proc. Natl. Acad. Sci. USA*, 88:8691-8695 (1991), United States National Academy of Science, District of Columbia, United States.
Stephenson, S.-A., et al., "Anti-tumour effects of antibodies targeting the extracellular cysteine-rich region of the receptor tyrosine kinase EphB4," *Oncotarget* 6(10):7554-7569, 2015, Impact Journals. Orchard Park, New York, United States.
Thaler, R., et al., "Mospd1, a New Player in Mesenchymal Versus Epidermal Cell Differentiation," *J. Cell. Physiol.* 226:2505-2515, 2011, Wiley-Liss, Inc., United States.
Zips, D., et al., "New Anticancer Agents: In Vitro and In Vivo Evaluation," *In Vivo*, 19:1-8 (2005), International Institute of Anticancer Research, Kapandriti, Greece.
English language translation of Document FP11, JP-A-S63-096123.
English language translation of Document FP12, JP-A-H10-237093.
English language translation of Document FP13, JP-2006-151902-A.
Editorial: "Dishing out cancer treatment," *Nature Biotechnology*, 31:85 (2013), Nature Research, Berlin, Germany.
Unpublished co-pending U.S. Appl. No. 18/049,084, filed Oct. 24, 2022, Inventors: Mendel et al.
Chames, P., et al., "Bispecific antibodies for cancer therapy. The light at the end of the tunnel?," *mAbs*, 1(6):539-547, 2009, Landes Bioscience, Austin, Texas.
Mendel, I., et al., "MOSPD2: A novel target for Bi-specific Ab mediated killing of tumor cells," Cancer Research, AACR Annual Meeting 2018, 78(13, Supp. 1):LB-132, American Association for Cancer Research, Chicago, Illinois.
Yacov, N., et al., "CD3 MOSPD2 bi specific antibody significantly prolongs survival in a model of metastatic human cervical cancer without any evidence of toxicity," Cancer Research, AACR Annual Meeting 2018, 80(16, Supp. 1):LB-086, American Association for Cancer Research, Chicago, Illinois.

\* cited by examiner

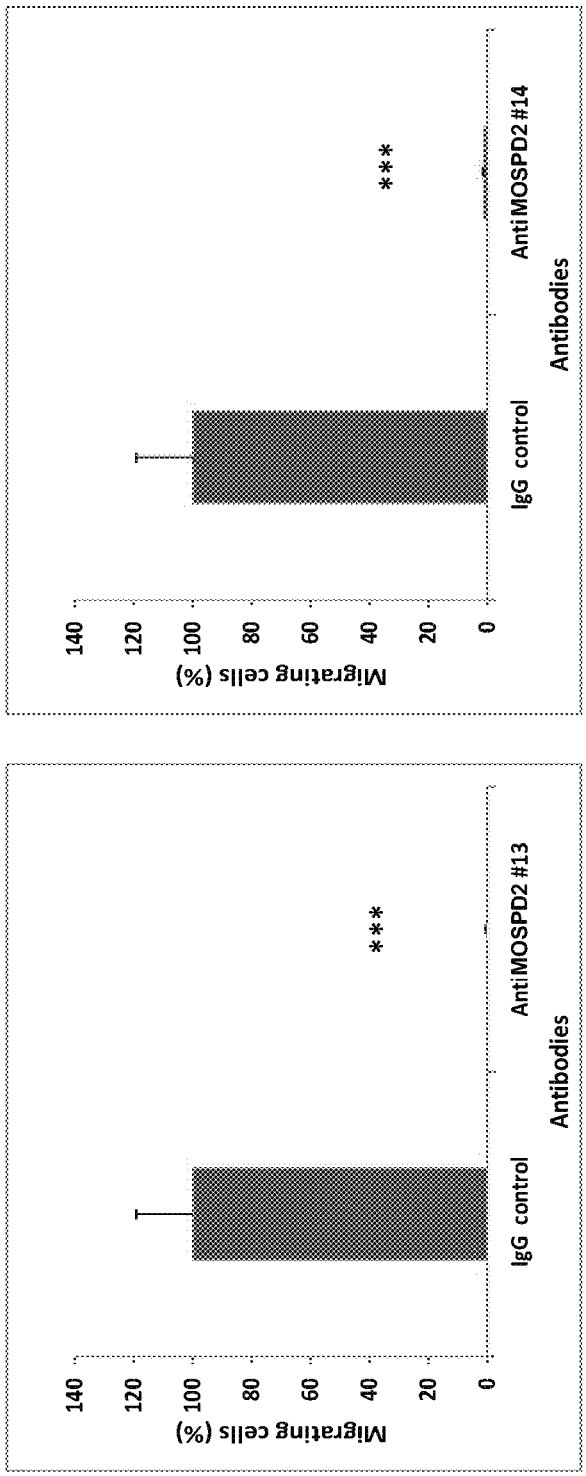

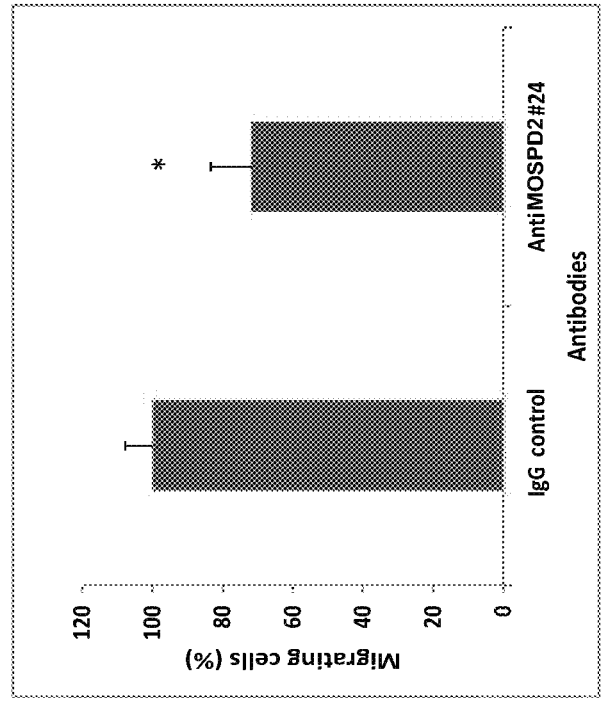
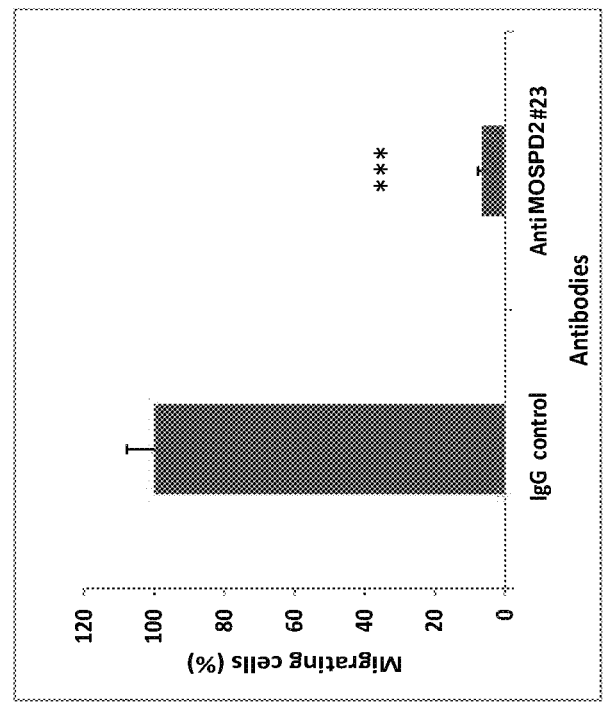
FIG. 4V
FIG. 4U

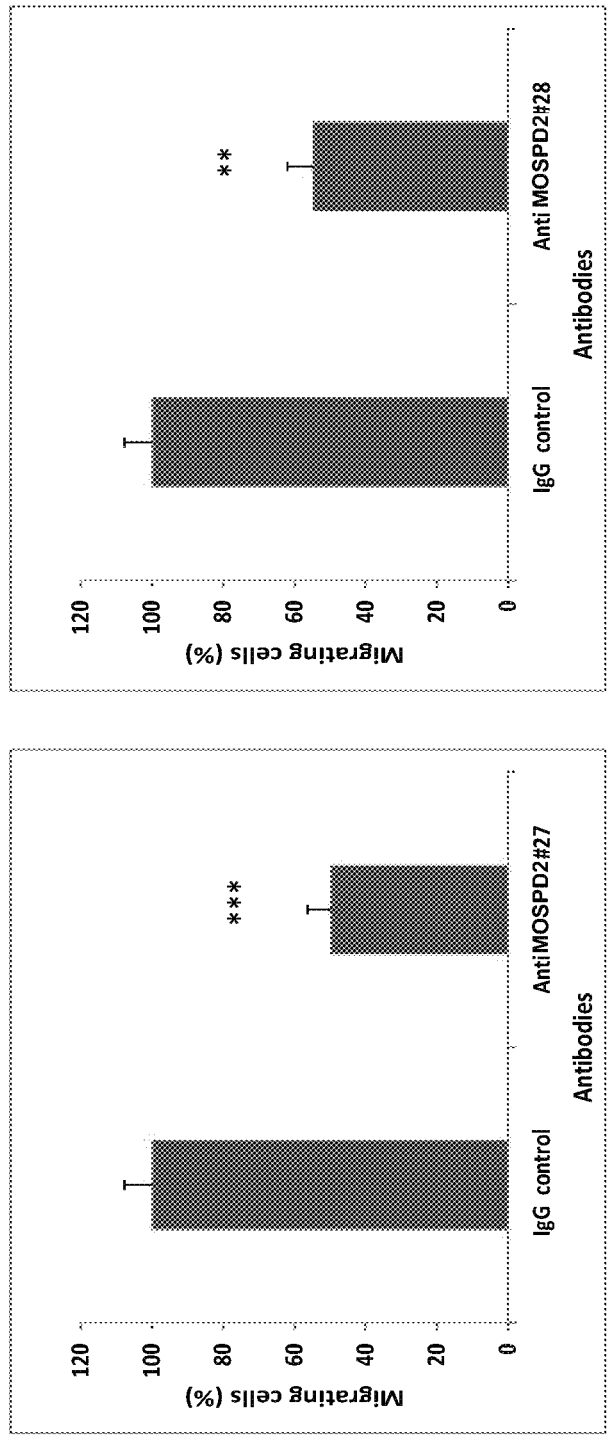

CHOW diet

Isotype control

Increased accumulation of CD68+ cells

Anti-MOSPD2

Reduced number of CD68+ cells

HFHC diet

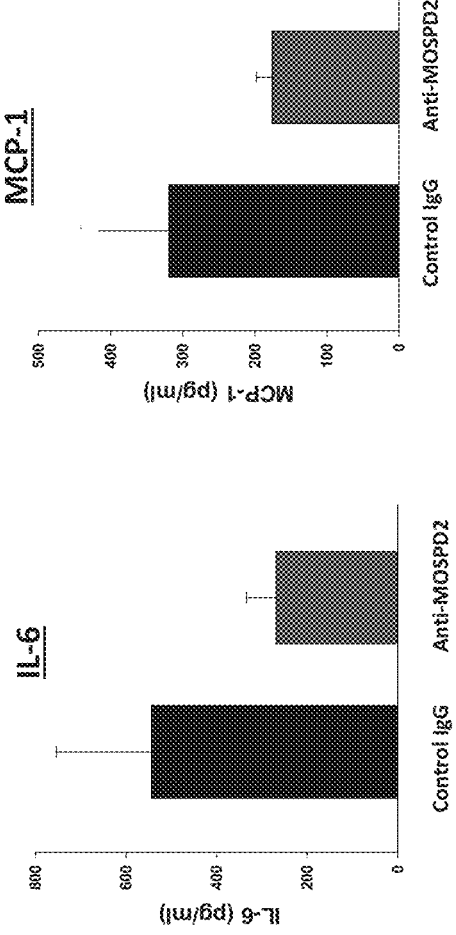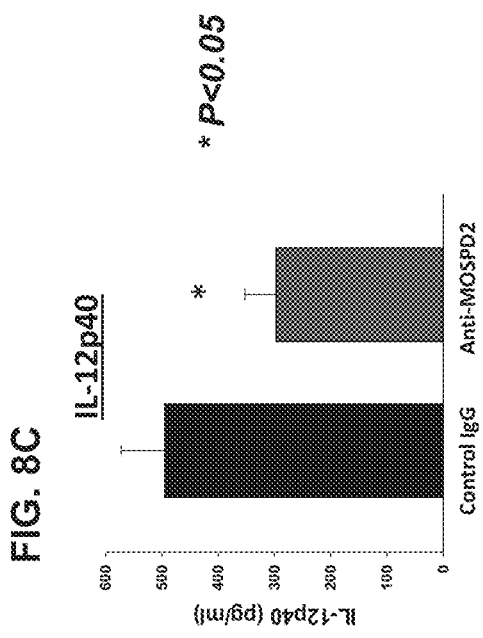

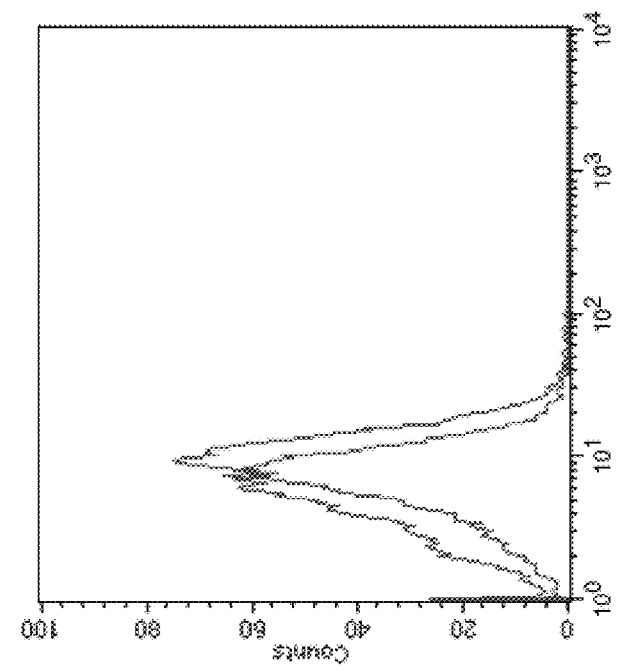
FIG. 13C   FIG. 13D
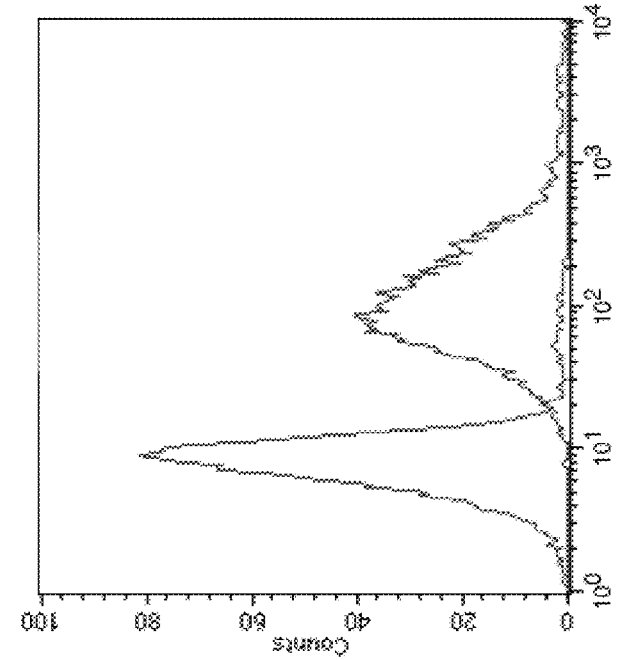

MOTILE SPERM DOMAIN CONTAINING PROTEIN 2 ANTIBODIES AND METHODS OF USE THEREOF

CROSS-REFERENCE TO RELATED APPLICATIONS

This application claims priority benefit to U.S. Provisional Appl. No. 63/076,697, filed Sep. 10, 2020, and U.S. Provisional Appl. No. 63/167,317, filed Mar. 29, 2021, the contents of which are hereby incorporated by reference in their entireties.

REFERENCE TO SEQUENCE LISTING SUBMITTED ELECTRONICALLY

The content of the electronically submitted sequence listing in ASCII text file (Name "3182_0960002_Seqlisting_ST25.txt"; Size: 40,794 bytes; and Date of Creation: Sep. 8, 2021) filed with the application is incorporated herein by reference in its entirety.

FIELD

The present disclosure relates to antibodies and antigen binding fragments thereof that specifically bind to Motile Sperm Domain Containing Protein 2 (MOSPD2) and methods of using the same.

BACKGROUND

Leukocytes are immune system cells involved in defending the body against infectious disease and foreign materials. Monocytes are a type of leukocytes and have critical roles in innate and adaptive immunity, immune surveillance, and particle scavenging. While a subset of monocytes is "resident" and recruited to tissues independently of inflammatory stimuli to assist in steady-state surveillance, wound-healing and resolution of inflammation, the majority (80-90%) of human circulating monocytes are classified as "inflammatory." Circulating monocytes can sense inflammatory stimuli and quickly migrate through the vascular or lymphatic endothelium to the periphery, where they can differentiate into macrophages and dendritic cells (DCs) which cooperate with additional cell subsets to promote inflammation. While playing a necessary role in host defense, monocytes are nonetheless identified as critical mediators of inflammatory disorders.

Chemokine receptors and adhesion molecules play a key role in regulation of leukocyte trafficking. A complex array of chemokine receptors, G-protein coupled receptors (GPCRs) that are differentially expressed on leukocyte lineages and subsets, regulates which cell types would migrate and to which tissue, under different conditions. Chemokines or chemotactic cytokines are secreted proteins that regulate migration and activation of leukocytes and stromal cells. Binding of chemokines to chemokine receptors activates signaling pathways such as the MAPK/ERK and PI3K/AKT pathways, resulting in phosphorylation of ERK and AKT, respectively. In the case of inflammatory monocytes, exit from the bone marrow across a monolayer of endothelial cells (diapedesis) to enter the circulatory system (intravasation) and to migrate to the inflamed tissue is dependent on C—C motif receptor 2 (CCR2) signaling, in response to activation by chemokine C—C motif ligand (CCL) 2 (also known as monocyte chemotactic protein-1; MCP-1) and CCL7 (MCP-3). On the other hand, constitutive migration of resident monocytes to non-inflamed tissues is mostly dependent on CCL3 (also known as Macrophage inflammatory protein-1α; MIP-1α) and chemokine (C-X3-C motif) ligand 1 (CX3CL1).

Inhibition of inflammatory cell migration (e.g., leukocyte chemotaxis) towards inflammatory sites is an attractive anti-inflammatory approach to treat chronic diseases. Suppressing the accumulation of unwanted monocytes and/or macrophages in chronically inflamed tissue has therapeutic potential, and migration inhibitors have accordingly demonstrated beneficial therapeutic results in animal models and clinical trials. Nevertheless, there have been several phase II clinical trial failures with chemokine and chemokine receptor antagonists, possibly due to redundancy of the target receptor and the complexity of heterogeneous diseases such as multiple sclerosis and rheumatoid arthritis.

Fibrosis is the formation of excess fibrous connective tissue in an organ or tissue. Fibrosis is similar to the process of scarring, in that both involve stimulated cells (e.g., fibroblasts) laying down connective tissue, including collagen and glycosaminoglycans. Fibrogenesis is a dynamic process and occurs in four phases: i) initiation, due to injury of the organ/tissue; ii) inflammation and activation of effector cells; iii) enhanced synthesis of extracellular matrix (ECM); and iv) deposition of ECM with progression to end-organ failure.

Fibrosis can cause severe morbidity and deleterious effects on patients' daily function, activity of daily living (ADL) and quality of life, and can lead to poor prognosis. For example, idiopathic pulmonary fibrosis (IPF) is a chronic intractable disease associated with worsening and debilitating shortness of breath. IPF patients become oxygen dependent, and have an average median survival time of three years and a five year survival rate of 20% to 40% after diagnosis. Therefore, the development of new therapies for fibrosis is needed.

Metastasis, the spread of cancer cells from their tissue of origin to other organs, is a result of a multi-step process that involves a number of molecules. Evidence suggests that chemokines and chemokine receptors play an important role in tumor metastasis.

MOSPD2 is a 518-amino acid long, highly conserved protein with 90% homology between human and mouse. Bioinformatic analyses indicate that MOSPD2 contains a CRAL-TRIO region, named after the cellular retinaldehyde-binding protein (CRALBP) and the TRIO protein. MOSPD2 also contains a structurally related region to the nematode major sperm protein and one transmembrane region.

MOSPD2 is expressed on the surface of monocytes that have infiltrated into inflamed tissues and on a variety of tumor types (Int'l Pub. No. WO 2017/021857). It is associated with metastasis of cancer cells and promotes monocyte migration (Int'l Pub. No. WO 2017/021857). Accordingly, inhibition of MOSPD2 (e.g., with anti-MOSPD2 antibodies) has been described as a treatment for inflammatory diseases and disorders (Int'l Pub. No. WO 2017/021855) and for cancer and cancer metastasis (Int'l Pub. No. WO 2017/021857).

BRIEF SUMMARY

Provided herein is an antibody or antigen binding fragment thereof that specifically binds to Motile Sperm Domain Containing Protein 2 (MOSPD2), comprising:

a heavy chain CDR1 comprising the amino acid sequence of SEQ ID NO:1 or a sequence having 80% or greater identity to SEQ ID NO:1;

a heavy chain CDR2 comprising the amino acid sequence of any one of SEQ ID NOs:2-8 or a sequence having 80% or greater identity to any one of SEQ ID NOs:2-8;

a heavy chain CDR3 comprising the amino acid sequence of SEQ ID NO:9;

a light chain CDR1 comprising the amino acid sequence of any one of SEQ ID NOs:10-18 or a sequence having 80% or greater identity to any one of SEQ ID NOs:10-18;

a light chain CDR2 comprising the amino acid sequence of any one of SEQ ID NOs:19-24 or a sequence having 80% or greater identity to any one of SEQ ID NOs:19-24; and a light chain CDR3 comprising the amino acid sequence of SEQ ID NO:25 or a sequence having 80% or greater identity to SEQ ID NO:25.

In some aspects, the antibody or antigen binding fragment thereof comprises:

a heavy chain CDR1 comprising the amino acid sequence of SEQ ID NO:1 or a sequence having 90% or greater identity to SEQ ID NO:1;

a heavy chain CDR2 comprising the amino acid sequence of any one of SEQ ID NOs:2-8 or a sequence having 90% or greater identity to any one of SEQ ID NOs:2-8;

a heavy chain CDR3 comprising the amino acid sequence of SEQ ID NO:9;

a light chain CDR1 comprising the amino acid sequence of any one of SEQ ID NOs:10-18 or a sequence having 90% or greater identity to any one of SEQ ID NOs:10-18;

a light chain CDR2 comprising the amino acid sequence of any one of SEQ ID NOs:19-24 or a sequence having 90% or greater identity to any one of SEQ ID NOs:19-24; and a light chain CDR3 comprising the amino acid sequence of SEQ ID NO:25 or a sequence having 90% or greater identity to SEQ ID NO:25.

In some aspects, the antibody or antigen binding fragment thereof comprises:

a heavy chain CDR1 comprising the amino acid sequence of SEQ ID NO:1 or a sequence having 95% or greater identity to SEQ ID NO:1;

a heavy chain CDR2 comprising the amino acid sequence of any one of SEQ ID NOs:2-8 or a sequence having 95% or greater identity to any one of SEQ ID NOs:2-8;

a heavy chain CDR3 comprising the amino acid sequence of SEQ ID NO:9;

a light chain CDR1 comprising the amino acid sequence of any one of SEQ ID NOs:10-18 or a sequence having 95% or greater identity to any one of SEQ ID NOs:10-18;

a light chain CDR2 comprising the amino acid sequence of any one of SEQ ID NOs:19-24 or a sequence having 95% or greater identity to any one of SEQ ID NOs:19-24; and a light chain CDR3 comprising the amino acid sequence of SEQ ID NO:25 or a sequence having 95% or greater identity to SEQ ID NO:25.

In some aspects, the antibody or antigen binding fragment thereof comprises:

a heavy chain CDR1 comprising the amino acid sequence of SEQ ID NO:1;

a heavy chain CDR2 comprising the amino acid sequence of any one of SEQ ID NOs:2-8;

a heavy chain CDR3 comprising the amino acid sequence of SEQ ID NO:9;

a light chain CDR1 comprising the amino acid sequence of any one of SEQ ID NOs:10-18;

a light chain CDR2 comprising the amino acid sequence of any one of SEQ ID NOs:19-24; and a light chain CDR3 comprising the amino acid sequence of SEQ ID NO:25.

In some aspects, the antibody or antigen binding fragment comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the antibody or antigen binding fragment comprises a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the antibody or antigen binding fragment comprises a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the antibody or antigen binding fragment comprises a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:6; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:22; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:6; a heavy chain CDR3 comprising the amino acid sequence of SEQ ID NO:9; a light chain CDR1 comprising the amino acid sequence of SEQ ID NO:14; a light chain CDR2 comprising the amino acid sequence of SEQ ID NO:23; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:8; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:16; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:18; a light chain CDR2 comprising the amino acid sequence of SEQ ID NO:19; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:22; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:24; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:24; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:22; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:24; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:22; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:24; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:22; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:24; and a light chain CDR3 comprising the amino acid sequence of SEQ ID NO:25.

In some aspects, the antibody or antigen binding fragment thereof comprises a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:22; and a light chain CDR3 comprising the amino acid sequence of SEQ ID NO:25.

Provided herein is an antibody or antigen binding fragment thereof that specifically binds to MOSPD2, comprising:

a heavy chain CDR1 comprising the amino acid sequence of SEQ ID NO:1 or a sequence having one or more conservative substitutions in SEQ ID NO:1;

a heavy chain CDR2 comprising the amino acid sequence of any one of SEQ ID NOs:2-8 or a sequence having one or more conservative substitutions in SEQ ID NOs:2-8;

a heavy chain CDR3 comprising the amino acid sequence of SEQ ID NO:9 or a sequence having one or more conservative substitutions in SEQ ID NO:9;

a light chain CDR1 comprising the amino acid sequence of any one of SEQ ID NOs:10-18 or a sequence having one or more conservative substitutions in any one of SEQ ID NOs:10-18;

a light chain CDR2 comprising the amino acid sequence of any one of SEQ ID NOs:19-24 or a sequence having one or more conservative amino acid substitutions in any one of SEQ ID NOs:19-24; and a light chain CDR3 comprising the amino acid sequence of SEQ ID NO:25 or a sequence having one or more conservative substitutions in SEQ ID NO:25.

In some aspects, the antibody or antigen binding fragment thereof is a polyclonal, monoclonal, murine, human, humanized, or chimeric antibody.

In some aspects, the antibody or antigen binding fragment thereof is a Fab, Fab', F(ab')2, Fv, scFv, sdFv fragment, VH domain, VL domain, or a combination thereof.

In some aspects, the antibody or antigen binding fragment thereof is an IgG1, IgG2, IgG3, IgG4, a variant thereof, or a combination thereof.

In some aspects, the antibody or antigen binding fragment thereof binds to MOSPD2 with a Ka value of from about $1 \times 10^5$ (l/Ms) to about $7 \times 10^6$ (l/Ms); a Kd value of from about $1 \times 10^{-4}$ (l/s) to about 0.4 (l/s); and/or a calculated KD of from about $2 \times 10^{-10}$ (M) to about $6 \times 10^{-8}$ (M).

In some aspects, the MOSPD2 is human MOSPD2. In some aspects, the MOSPD2 has an amino acid sequence of any one of SEQ ID NOs:26-29. In some aspects, the MOSPD2 has an amino acid sequence encoded by the nucleic acid sequence of any one of SEQ ID NOs:30-33.

Provided herein is a nucleic acid encoding an antibody or antigen binding fragment thereof described herein.

Provided herein is a vector comprising a nucleic acid encoding an antibody or antigen binding fragment thereof described herein.

Provided herein is a cell comprising a vector comprising a nucleic acid encoding an antibody or antigen binding fragment thereof described herein.

Provided herein is a method of producing an antibody or antigen binding fragment thereof that specifically binds to MOSPD2, comprising culturing a cell comprising a vector comprising a nucleic acid encoding an antibody or antigen binding fragment thereof described herein under suitable conditions and isolating the antibody or antigen binding fragment.

Provided herein is a composition comprising an antibody or antigen binding fragment thereof described herein, a nucleic acid encoding an antibody or antigen binding fragment thereof described herein, a vector comprising a nucleic acid encoding an antibody or antigen binding fragment thereof described herein, or a cell comprising a vector comprising a nucleic acid encoding an antibody or antigen binding fragment thereof described herein, and a carrier.

Provided herein is a kit comprising an antibody or antigen binding fragment thereof described herein, a nucleic acid encoding an antibody or antigen binding fragment thereof described herein, a vector comprising a nucleic acid encoding an antibody or antigen binding fragment thereof described herein, or a cell comprising a vector comprising a nucleic acid encoding an antibody or antigen binding fragment thereof described herein, and an instruction for use.

Provided herein is a method of treating or preventing an inflammatory disease or disorder, comprising administering to a subject in need thereof a therapeutically effective amount of an antibody or antigen binding fragment described herein.

Provided herein is a method of inhibiting or preventing migration of an inflammatory cell, comprising administering to a subject in need thereof a therapeutically effective amount of an antibody or antigen binding fragment described herein. In some aspects, the inflammatory cell is a monocyte or neutrophil.

Provided herein is a method of treating or preventing nonalcoholic fatty liver disease (NAFLD) or nonalcoholic steatohepatitis (NASH), comprising administering to a subject in need thereof a therapeutically effective amount of an antibody or antigen binding fragment described herein.

Provided herein is a method of treating or preventing fibrosis, comprising administering to a subject in need thereof a therapeutically effective amount of an antibody or antigen binding fragment described herein. In some aspects, the fibrosis is liver fibrosis.

Provided herein is a method of treating or preventing arthritis, comprising administering to a subject in need thereof a therapeutically effective amount of an antibody or antigen binding fragment described herein. In some aspects, the arthritis is rheumatoid arthritis or psoriatic arthritis. In some aspects, the method further comprises administering to the subject an additional therapeutic agent. In some aspects, the additional therapeutic agent is methotrexate, baricitinib, hydroxychloroquine, prednisone, etanercept, sulfasalazine, infliximab, adalimumab, ixekizumab, or a combination thereof.

Provided herein is a method of treating or preventing multiple sclerosis, comprising administering to a subject in need thereof a therapeutically effective amount of an antibody or antigen binding fragment described herein. In some aspects, the multiple sclerosis is relapsing remitting multiple sclerosis, primary progressive multiple sclerosis, or secondary progressive multiple sclerosis. In some aspects, the method further comprises administering to the subject an additional therapeutic agent. In some aspects, the additional therapeutic agent is teriflunomide, natalizumab, dimethyl fumarate, ocrelizumab, IFNβ-1a, cladribine, glatiramer acetate, or a combination thereof.

Provided herein is a method of treating or preventing inflammatory bowel disease, comprising administering to a subject in need thereof a therapeutically effective amount of an antibody or antigen binding fragment described herein. In some aspects, the inflammatory bowel disease is ulcerative colitis or Crohn's disease. In some aspects, the method further comprises administering to the subject an additional therapeutic agent. In some aspects, the additional therapeutic agent is infliximab, vedolizumab, azathioprine, adalimumab, masalazine, or a combination thereof.

Provided herein is a method of treating or preventing metastasis of cancer, comprising administering to a subject in need thereof a therapeutically effective amount of an antibody or antigen binding fragment described herein.

Provided herein is a method of treating or preventing cancer, comprising administering to a subject in need thereof a therapeutically effective amount of an antibody or antigen binding fragment described herein.

In some aspects, the cancer is breast cancer, cervical cancer, melanoma, myeloid cancer, colon cancer, kidney cancer, liver cancer, lung cancer, ovarian cancer, pancreatic cancer, thyroid cancer, or prostate cancer.

In some aspects, the antibody or antigen binding fragment thereof is administered to the subject intravenously or subcutaneously.

In some aspects, the subject is human.

BRIEF DESCRIPTION OF THE DRAWINGS

Some aspects of the invention are herein described, by way of example only, with reference to the accompanying drawings. With specific reference now to the drawings in detail, it is stressed that the particulars shown are by way of example and for purposes of illustrative discussion of aspects of the invention.

FIGS. 8A-8C (FIGS. 8A-8C) shows the effect of anti-MOSPD2 antibody treatment on IL-6, MCP-1 and IL-12p40 levels in a TNBS-induced Colitis mouse model. *p<0.05.

FIGS. 13A-13D (FIGS. 13A-13D) shows flow cytometry analysis for surface expression of MOSPD2 of different human cancer cell lines.

DETAILED DESCRIPTION OF THE INVENTION

Figure 1:
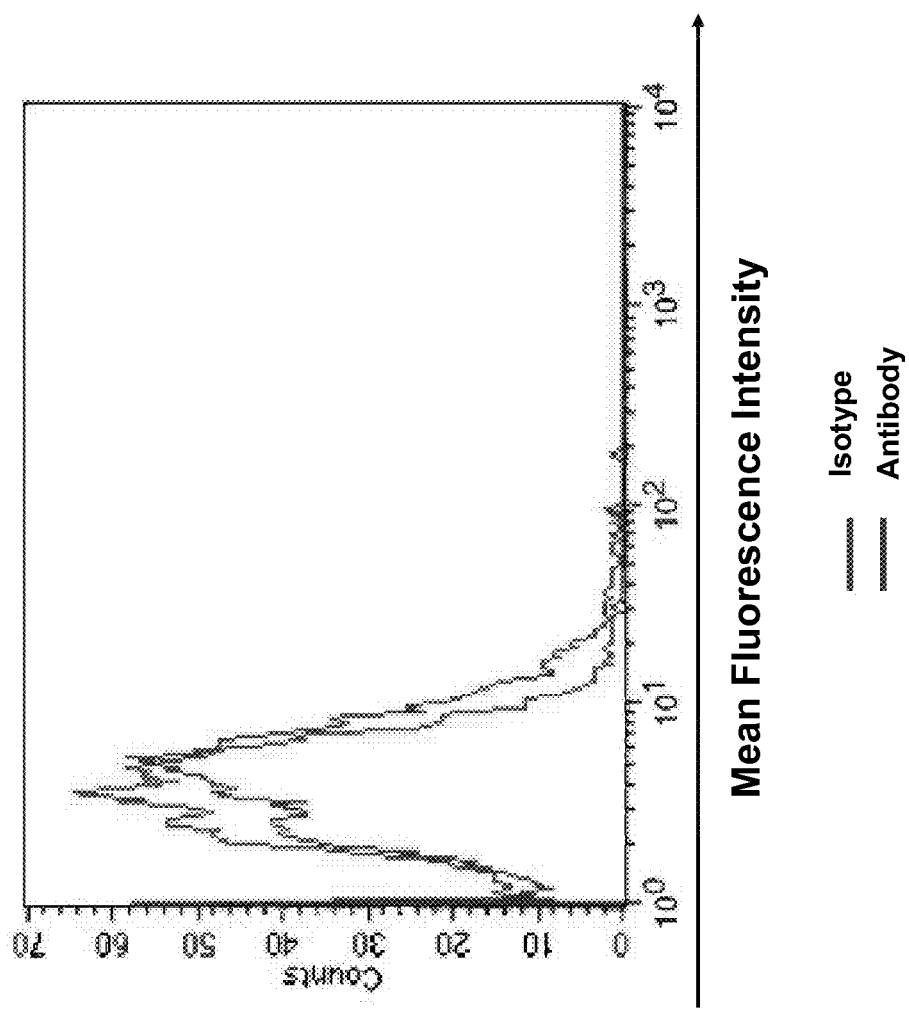
FIG. 1 (FIG. 1) shows a flow cytometry analysis for surface expression of MOSPD2 on human monocytes.

In order that the present disclosure may be more readily understood, certain terms are first defined. As used in this application, except as otherwise expressly provided herein, each of the following terms shall have the meaning set forth below. Additional definitions are set forth throughout the application.

Definitions

Various terms relating to aspects of disclosure are used throughout the specification and claims. Such terms are to be given their ordinary meaning in the art, unless otherwise indicated. Other specifically defined terms are to be construed in a manner consistent with the definition provided herein.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

Where not expressly stated, and unless the context indicates otherwise, the term "antibody" includes monospecific, bispecific, or multi-specific antibodies, as well as a single chain antibody.

An "antigen binding fragment" refers to a portion of an intact antibody that binds to an antigen. An antigen binding fragment can contain an antigen recognition site of an intact antibody (e.g., complementarity determining regions (CDRs) sufficient to specifically bind antigen). Examples of antigen binding fragments of antibodies include, but are not limited to Fab, Fab', F(ab')2, and Fv fragments, linear antibodies, and single chain antibodies. An antigen binding fragment of an antibody can be derived from any animal species, such as rodents (e.g., mouse, rat, or hamster) and humans or can be artificially produced.

A "monoclonal" antibody or antigen binding fragment thereof refers to a homogeneous antibody or antigen binding fragment population involved in the highly specific binding of a single antigenic determinant, or epitope. This is in contrast to polyclonal antibodies that typically include different antibodies directed against different antigenic determinants. The term "monoclonal" antibody or antigen binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen binding fragment thereof refers to such antibodies and antigen binding fragments thereof made in any number of manners including but not limited to by hybridoma, phage selection, recombinant expression, and transgenic animals.

The term "humanized" antibody or antigen binding fragment thereof refers to forms of non-human (e.g. murine) antibodies or antigen binding fragments that are specific immunoglobulin chains, chimeric immunoglobulins, or fragments thereof that contain minimal non-human (e.g., murine) sequences. Typically, humanized antibodies or antigen binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., *Nature* 321:522-525 (1986); Riechmann et al., *Nature* 332:323-327 (1988); Verhoeyen et al., *Science* 239:1534-1536 (1988)). In some instances, certain Fv framework region (FR) residues of a human immunoglobulin are replaced with the corresponding residues in an antibody or fragment from a non-human species that has the desired specificity, affinity, and capability. The humanized antibody or antigen binding fragment thereof can be further modified by the substitution of additional residues either in the Fv framework region and/or within the non-human CDR residues to refine and optimize antibody or antigen binding fragment thereof specificity, affinity, and/or capability. In general, the humanized antibody or antigen binding fragment thereof will comprise variable domains containing all or substantially all of the CDR regions that correspond to the non-human immunoglobulin whereas all or substantially all of the FR regions are those of a human immunoglobulin consensus sequence. The humanized antibody or antigen binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., *Proc. Natl. Acad. Sci., USA*, 91(3):969-73 (1994), and Roguska et al., *Protein Eng.* 9(10):895-904 (1996).

The term "human" antibody or antigen binding fragment thereof means an antibody or antigen binding fragment thereof having an amino acid sequence derived from a human immunoglobulin gene locus, where such antibody or antigen binding fragment is made using any technique known in the art. This definition of a human antibody or antigen binding fragment thereof includes intact or full-length antibodies and fragments thereof.

As used herein, the term "treating" includes abrogating, inhibiting, slowing or reversing the progression of a condition, substantially ameliorating clinical or aesthetical symptoms of a condition or substantially preventing the appearance of clinical or aesthetical symptoms of a condition.

The terms "administer," "administering," "administration," and the like, as used herein, refer to methods that can be used to enable delivery of an antibody or antigen binding fragment thereof to the desired site of biological action (e.g., intravenous administration). Administration techniques that can be employed with the agents and methods described herein are found in e.g., Goodman and Gilman, The Pharmacological Basis of Therapeutics, current edition, Pergamon; and Remington's, Pharmaceutical Sciences, current edition, Mack Publishing Co., Easton, Pa. and Matucci, A. et al., *Respiratory Research*, 19(1):154 (2018).

The terms "subject" and "patient" are used interchangeably and include any animal. Mammals are preferred, including companion (e.g., cat, dog) and farm mammals (e.g., pig, horse, cow), as well as rodents, including mice, rabbits, and rats, guinea pigs, and other rodents. Non-human primates are more preferred, and human are highly preferred.

As used herein, "MOSPD2" refers to any polypeptide classified as Motile Sperm Domain Containing Protein 2. Examples of MOSPD2 include, but are not limited to, the polypeptides of SEQ ID NOs:26-29, or any variant thereof (e.g., having a sequence at least 75%, at least 80%, at least 85%, at least 90%, at least 95%, at least 96%, at least 97%, at least 98%, or at least 99% identical to any one of SEQ ID NOs:26-29). Other examples of MOSPD2 include, but are not limited to, a polypeptide encoded by a polynucleotide of any one of SEQ ID NOs:30-33, or any variant thereof (e.g., a polynucleotide having at least 75%, at least 80%, at least 85%, at least 90%, at least 95%, at least 96%, at least 97%, at least 98%, or at least 99% identical to any one of SEQ ID NOs:30-33). Polynucleotide sequences encoding MOSPD2 can be codon optimized for expression in a particular organism by methods known in the art. Other examples of MOSPD2 can be identified by searching public databases (e.g., BLAST), as well known to one skilled in the art.

A "constant region" of an antibody refers to the constant region of the antibody light chain or the constant region of the antibody heavy chain, either alone or in combination.

The term "Fc region" is used to define a C-terminal region of an immunoglobulin heavy chain. The "Fc region" can be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3.

By "specifically binds," it is generally meant that an antibody or fragment, variant, or derivative thereof binds to an epitope by its antigen binding domain, and that the binding entails some complementarity between the antigen binding domain and the epitope. According to this definition, an antibody or fragment, variant, or derivative thereof is said to "specifically bind" to an epitope when it binds to that epitope via its antigen binding domain more readily than it would bind to a random, unrelated epitope.

The term "inflammatory cell" includes, but is not limited to, a leukocyte, granulocyte, neutrophil, basophil, eosinophil, monocyte, macrophage, lymphocyte, mast cell, dendritic cell, or the like.

The term "percent identity," as known in the art, is a relationship between two or more polypeptide sequences or two or more polynucleotide sequences, as determined by comparing the sequences. In the art, "identity" and "sequence identity" also mean the degree of sequence relatedness between polypeptide or polynucleotide sequences, as the case may be, as determined by the match between strings of such sequences. "Identity" and "similarity" can be readily calculated by known methods and publicly available resources, including but not limited to those described in: (1) Computational Molecular Biology (Lesk, A. M., Ed.) Oxford University: NY (1988); (2) Biocomputing: Informatics and Genome Projects (Smith, D. W., Ed.) Academic: NY (1993); (3) Computer Analysis of Sequence Data, Part I (Griffin, A. M., and Griffin, H. G., Eds.) Humania: NJ (1994); (4) Sequence Analysis in Molecular Biology (von Heinje, G., Ed.) Academic (1987); and (5) Sequence Analysis Primer (Gribskov, M. and Devereux, J., Eds.) Stockton: NY (1991).

As used in the present disclosure and claims, the singular forms "a," "an," and "the" include plural forms unless the context clearly dictates otherwise.

It is understood that wherever aspects of the present disclosure are described herein with the language "comprising," otherwise analogous aspects described in terms of "consisting of" and/or "consisting essentially of" are also provided.

Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of ±10% of the value or range remain within the intended meaning of the recited value or range. As is understood by one skilled in the art, reference to "about" a value or range herein includes (and describes) instances that are directed to that value or range per se. For example, description referring to "about X" includes description of "X."

Any compositions or methods provided herein can be combined with one or more of any of the other compositions and methods provided herein.

Throughout this application, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Anti-MOSPD2 Antibodies and Antigen Binding Fragments Thereof

In some aspects, the disclosure provides an antibody or antigen binding fragment thereof that specifically binds to MOSPD2. In some aspects, the disclosure provides an antibody or antigen binding fragment thereof that specifically binds to MOSPD2, comprising, consisting of, or consisting essentially of:

(i) a heavy chain CDR1 comprising the amino acid sequence of SEQ ID NO:1 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:3; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:4; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:11; a light chain CDR2 comprising the amino acid sequence of SEQ ID NO:20; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:5; a heavy chain CDR3 comprising the amino acid sequence of SEQ ID NO:9; a light chain CDR1 comprising the amino acid sequence of SEQ ID NO:12; a light chain CDR2 comprising the amino acid sequence of SEQ ID NO:21; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:6; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:22; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:6; a heavy chain CDR3 comprising the amino acid sequence of SEQ ID NO:9; a light chain CDR1 comprising the amino acid sequence of SEQ ID NO:14; a light chain CDR2 comprising the amino acid sequence of SEQ ID NO:23; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:8; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:16; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:18; a light chain CDR2 comprising the amino acid sequence of SEQ ID NO:19; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:22; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:2; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:24; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:24; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:10; a light chain CDR2 comprising the amino acid sequence of SEQ ID NO:22; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:24; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:15; a light chain CDR2 comprising the amino acid sequence of SEQ ID NO:22; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:24; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:17; a light chain CDR2 comprising the amino acid sequence of SEQ ID NO:22; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:24; and a light chain CDR3 comprising the amino acid sequence of SEQ ID NO:25.

In some aspects, the disclosure provides an antibody or antigen binding fragment thereof, comprising a heavy chain CDR1 comprising the amino acid sequence of SEQ ID NO:1; a heavy chain CDR2 comprising the amino acid sequence of SEQ ID NO:7; a heavy chain CDR3 comprising the amino acid sequence of SEQ ID NO:9; a light chain CDR1 comprising the amino acid sequence of SEQ ID NO:13; a light chain CDR2 comprising the amino acid sequence of SEQ ID NO:22; and a light chain CDR3 comprising the amino acid sequence of SEQ ID NO:25.

In other aspects, the antibodies or antigen binding fragments thereof comprise a constant region. In some aspects, the constant region of the light chain comprises the amino acid sequence of a human kappa light chain constant region or a human lambda light chain constant region. In some aspects, the constant region of the heavy chain comprises the amino acid sequence of a human gamma heavy chain constant region. Non-limiting examples of human constant region sequences have been described, e.g., see U.S. Pat. No. 5,693,780 and Kabat, E A et al., (1991).

In some aspects, the disclosure provides an antibody or antigen binding fragment thereof that specifically binds to MOSPD2, comprising, consisting of, or consisting essentially of (i) a heavy chain CDR1 comprising the amino acid sequence of SEQ ID NO:1 or a sequence having one or more conservative substitutions in SEQ ID NO:1 (e.g., from about 1 to about 20 conservative substitutions, or any value of range of values therein);

(ii) a heavy chain CDR2 comprising the amino acid sequence of any one of SEQ ID NOs:2-8 or a sequence having one or more conservative substitutions in SEQ ID NOs:2-8 (e.g., from about 1 to about 20 conservative substitutions, or any value of range of values therein);

(iii) a heavy chain CDR3 comprising the amino acid sequence of SEQ ID NO:9 or a sequence having one or more conservative substitutions in SEQ ID NO:9 (e.g., from about 1 to about 20 conservative substitutions, or any value of range of values therein);

(iv) a light chain CDR1 comprising the amino acid sequence of any one of SEQ ID NOs:10-18 or a sequence having one or more conservative substitutions in any one of SEQ ID NOs:10-18 (e.g., from about 1 to about 20 conservative substitutions, or any value of range of values therein);

(v) a light chain CDR2 comprising the amino acid sequence of any one of SEQ ID NOs:19-24 or a sequence having one or more conservative substitutions in any one of SEQ ID NOs:19-24 (e.g., from about 1 to about 20 conservative substitutions, or any value of range of values therein); and (vi) a light chain CDR3 comprising the amino acid sequence of SEQ ID NO:25 or a sequence having one or more conservative substitutions in SEQ ID NO:25 (e.g., from about 1 to about 20 conservative substitutions, or any value of range of values therein).

In some aspects, the conservative substitution is a replacement of an amino acid with a different amino acid having similar charge, hydrophobicity and/or size. In some aspects, the conservative substitution is a substitution of one or more of the amino acids in Table 1 for another amino acid in the same class.

TABLE 1

Examples of Conservative Substitutions

| Class | Amino Acids |
|---|---|
| Aliphatic | Glycine, Alanine, Valine, Leucine, Isoleucine |
| Hydroxyl or sulfur/selenium-containing | Serine, Cysteine, Selenocysteine, Threonine, Methionine |
| Aromatic | Phenylalanine, Tyrosine, Tryptophan |
| Basic | Histidine, Lysine, Arginine |
| Acidic and their amides | Aspartate, Glutamate, Asparagine, Glutamine |

Methods for making substitutions in an amino acid sequence are known in the art and described, for example, in Yampolsky et al., "The Exchangeability of Amino Acids in Proteins," Genetics. 170(4):1459-1472; 2005

An antibody or antigen-binding fragment thereof is preferably monoclonal, and more preferably is a full length antibody comprising two heavy chains and two light chains. In some aspects, the antibody or antigen-binding fragment thereof comprises a derivative or fragment or portion of an antibody that retains the antigen-binding specificity, and also preferably retains most or all of the affinity, of the full length recombinant antibody. For example, derivatives may comprise at least one variable region (either a heavy chain or light chain variable region). Other examples of suitable antibody derivatives and fragments include, without limitation, antibodies with polyepitopic specificity, bispecific antibodies, multi-specific antibodies, diabodies, single-chain molecules, as well as FAb, F(Ab')$_2$, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies can be multi-valent. All antibody isotypes can be used to produce antibody derivatives, fragments, and portions. Antibody derivatives, fragments, and/or portions can be recombinantly produced and expressed by any cell type, prokaryotic or eukaryotic.

In a full-length antibody, each heavy chain is comprised of a heavy chain variable region and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Typically, the antigen binding properties of an antibody are less likely to be disturbed by changes to FR sequences than by changes to the CDR sequences. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In some aspects, an antibody or antigen binding fragment thereof is fully human. Fully human antibodies are those where the whole molecule is human or otherwise of human origin, or includes an amino acid sequence identical to a human form of the antibody. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may nevertheless include amino acid residues not encoded by human sequences, e.g., mutations introduced by random or site directed mutations.

In some aspects, an antibody or antigen binding fragment thereof comprises non-immunoglobulin derived protein frameworks. For example, reference may be made to Ku & Schutz, Proc. Natl. Acad. Sci. USA, 92:6552-6 (1995), which describes a four-helix bundle protein cytochrome b562 having two loops randomized to create CDRs, which have been selected for antigen binding.

In some aspects, the recombinant or antigen binding fragment thereof comprises post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. Moieties include any chemical group or combinations of groups commonly found on immunoglobulin molecules in nature or otherwise added to antibodies by recombinant expression systems, including prokaryotic and eukaryotic expression systems.

Examples of side chain modifications contemplated by the disclosure include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

In some aspects, an antibody or antigen binding fragment thereof includes one or more modifications that modulate serum half-life and biodistribution, including without limitation, modifications that modulate the antibody's interaction with the neonatal Fc receptor (FcRn), a receptor with a key role in protecting IgG from catabolism, and maintaining high serum antibody concentration.

An antibody or antigen binding fragment thereof may be labelled, bound, or conjugated to any chemical or biomolecule moieties. Labelled antibodies may find use in therapeutic, diagnostic, or basic research applications. Such labels/conjugates can be detectable, such as fluorochromes, electrochemiluminescent probes, quantum dots, radiolabels, enzymes, fluorescent proteins, luminescent proteins, and biotin. The labels/conjugates may be chemotherapeutic agents, toxins, isotopes, and other agents used for treating conditions such as the killing of cancer cells. Chemotherapeutic agents may be any which are suitable for the purpose for which the antibody is being used.

In some aspects, the antibody or antigen binding fragment thereof can be derivatized by known protecting/blocking groups to prevent proteolytic cleavage or enhance activity or stability.

In some aspects, the antibody or antigen binding fragment thereof is a polyclonal, monoclonal, murine, human, humanized, or chimeric antibody.

In some aspects, the antibody or antigen binding fragment thereof is a Fab, Fab', F(ab')2, Fv, scFv, sdFv fragment, VH domain, VL domain, or a combination thereof.

In some aspects, the antibody or antigen binding fragment thereof is an IgG, IgM, IgE, IgA, IgD, a variant thereof, or a combination thereof. In some aspects, the antibody or antigen binding fragment thereof is an IgG1, IgG2, IgG3, IgG4, a variant thereof, or a combination thereof.

In some aspects, the antibody or antigen binding fragment thereof binds to MOSPD2 with a Ka value of from about $1\times10^5$ (l/Ms) to about $7\times10^6$ (l/Ms); a Kd value of from about $1\times10^{-4}$ (l/s) to about 0.4 (l/s); and/or a calculated KD of from about $2\times10^{-10}$ (M) to about $6\times10^{-8}$ (M).

In some aspects, the disclosure provides an antibody or antigen binding fragment that specifically binds to MOSPD2 wherein the MOSPD2 is human MOSPD2.

In some aspects, the disclosure provides an antibody or antigen binding fragment thereof that specifically binds to MOSPD2 having an amino acid sequence of any one of SEQ ID NOs:26-29 or an amino acid sequence having about 75%, 80%, 85%, 90%, 95%, 96%, 97%, 98%, 99% or greater identity to any one of SEQ ID NOs:26-29.

In some aspects, the disclosure provides an antibody or antigen binding fragment thereof that specifically binds to MOSPD2 having an amino acid sequence encoded by the nucleic acid sequence of any one of SEQ ID NOs:30-33 or an amino acid sequence having about 75%, 80%, 85%, 90%, 95%, 96%, 97%, 98%, 99% or greater identity to any one of SEQ ID NOs:30-33.

In some aspects, the disclosure provides an antibody or antigen binding fragment thereof that competes for binding to MOSPD2 with an antibody or antigen binding fragment described herein. Competition for binding can be determined using assays known to one of skill in the art, including but not limited to, ELISA competitive assays, surface plasmon resonance, and Scatchard analysis.

In some aspects, the disclosure provides a nucleic acid encoding an antibody or antigen binding fragment thereof described herein that specifically binds to MOSPD2. In some aspects, the disclosure provides a vector comprising a nucleic acid encoding an antibody or antigen binding fragment thereof described herein that specifically binds to MOSPD2. In some aspects, the disclosure provides a cell comprising a vector comprising a nucleic acid encoding an antibody or antigen binding fragment thereof described herein that specifically binds to MOSPD2, or a nucleic acid encoding an antibody or antigen binding fragment thereof described herein that specifically binds to MOSPD2.

In some aspects, the disclosure provides a method of producing an antibody or antigen binding fragment thereof that specifically binds to MOSPD2, comprising culturing a cell comprising a vector comprising a nucleic acid encoding an antibody or antigen binding fragment thereof described herein that specifically binds to MOSPD2 under suitable conditions and isolating the antibody or antigen binding fragment.

Compositions and Kits

In some aspects, the disclosure provides a composition comprising an antibody or antigen binding fragment described herein. In some aspects, the disclosure provides a composition comprising an antibody or antigen binding fragment comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a composition comprising an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the composition comprises an antibody or antigen binding fragment described herein and a carrier. In some aspects, the carrier is a diluent, adjuvant, excipient, or vehicle with which the compound is administered. Examples of a carrier include, but are not limited to, liquids, such as water and oils. Water, aqueous solution saline, and aqueous dextrose and glycerol solutions can also be employed as carriers, particularly for injectable solutions.

In some aspects, the composition is formulated for administration as an injection or infusion. Routes of administration by injection or infusion include intravenous, intraperitoneal, intramuscular, intrathecal and subcutaneous.

In some aspects, the disclosure provides a composition comprising a nucleic acid encoding an antibody or antigen binding fragment thereof described herein, a vector comprising such a nucleic acid, or a cell comprising such a nucleic acid or vector. In some aspects, the composition further comprises a carrier.

In some aspects, the disclosure provides a kit comprising (i) an antibody or antigen binding fragment described herein, a nucleic acid encoding an antibody or antigen binding fragment thereof described herein, a vector comprising such a nucleic acid, or a cell comprising such as nucleic acid or vector; and (ii) an instruction for use.

In some aspects, the disclosure provides a composition comprising an antibody or antigen binding fragment described herein and one or more additional active agents.

Methods of Use

In some aspects, the disclosure provides a method of treating or preventing an inflammatory disease or disorder, comprising administering to a subject in need thereof a therapeutically effective amount of an antibody or antigen binding fragment described herein. In some aspects, the disclosure provides a method of treating or preventing an inflammatory disease or disorder, comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing an inflammatory disease or disorder, comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the inflammatory disease or disorder is an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, necrosis, an inflammatory implant-related disease or disorder, an inflammatory aging process, an immunodeficiency disease or disorder, or an inflammatory pulmonary disease or disorder.

In some aspects, the hypersensitivity is Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, or TH2 lymphocyte mediated hypersensitivity.

In some aspects, the inflammatory cardiovascular disease or disorder is an occlusive disease or disorder, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, or anti-helper T lymphocyte autoimmunity.

In some aspects, the inflammatory cerebrovascular disease or disorder is stroke, cerebrovascular inflammation, cerebral hemorrhage, or vertebral arterial insufficiency.

In some aspects, the peripheral vascular disease or disorder is gangrene, diabetic vasculopathy, thrombosis, diabetic retinopathy, or diabetic nephropathy.

In some aspects, the autoimmune disease or disorder is systemic lupus erythematosus, scleroderma, mixed connective tissue disease, polyarteritis nodosa, polymyositis/dermatomyositis, Sjogren's syndrome, Bechet's disease, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides, or heparin induced thrombocytopenia.

In some aspects, the inflammatory glandular disease or disorder is a pancreatic disease or disorder, Type I diabetes, thyroid disease or disorder, Graves' disease or disorder, thyroiditis, spontaneous autoimmune thyroiditis, Hashimoto's thyroiditis, idiopathic myxedema, ovarian autoimmunity, autoimmune anti-sperm infertility, autoimmune prostatitis, or Type I autoimmune polyglandular syndrome.

In some aspects, the inflammatory cutaneous disease or disorder is acne, autoimmune bullous skin disease or disorder, pemphigus vulgaris, bullous pemphigoid, pemphigus foliaceus, contact dermatitis, or drug eruption.

In some aspects, the inflammatory hepatic disease or disorder is autoimmune hepatitis, hepatic cirrhosis, or biliary cirrhosis.

In some aspects, the inflammatory neurological disease or disorder is Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis, stroke, an inflammatory retinal disease or disorder, an inflammatory ocular disease or disorder, optic neuritis, spongiform encephalopathy, migraine, headache, cluster headache, or stiff-man syndrome.

In some aspects, the inflammatory connective tissue disease or disorder is Duchenne muscular dystrophy (DMD), autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, ankylosing spondylitis, a skeletal inflammation, an autoimmune ear disease or disorder, or an autoimmune disease or disorder of the inner ear.

In some aspects, the inflammatory renal disease or disorder is autoimmune interstitial nephritis.

In some aspects, the inflammatory reproductive disease or disorder is repeated fetal loss, ovarian cyst, or a menstruation associated disease or disorder.

In some aspects, the inflammatory systemic disease or disorder is systemic lupus erythematosus, systemic sclerosis, septic shock, toxic shock syndrome, or cachexia.

In some aspects, the infectious disease or disorder is a chronic infectious disease or disorder, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, or severe acute respiratory syndrome.

In some aspects, the inflammatory transplantation-related disease or disorder is graft rejection, chronic graft rejection, subacute graft rejection, acute graft rejection hyperacute graft rejection, or graft versus host disease or disorder.

In some aspects, the implant is a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, or a respirator tube.

In some aspects, the inflammatory pulmonary disease or disorder is asthma, allergic asthma, emphysema, chronic obstructive pulmonary disease or disorder, sarcoidosis, or bronchitis.

In some aspects, the inflammatory disease or disorder is vascular inflammation in a subject suffering from a chronic autoimmune or chronic inflammatory disease. In some aspects, the chronic autoimmune or inflammatory disease is psoriasis. In some aspects, the vascular inflammation is associated with a cardiovascular disease, a peripheral vascular disease, a coronary artery disease, a cerebral vascular disease, a renal artery stenosis, an ischemic disease, or an aortic aneurism. In some aspects, the vascular inflammation is associated with an ischemic heart disease, atherosclerosis, acute coronary syndrome, unstable angina, stable angina, or stroke. In other aspects, the vascular inflammation is inflammation of a carotid artery. In other aspects, the vascular inflammation is inflammation of an aorta.

In some aspects, the inflammatory disease or disorder is inflammation associated with an implant. In some aspects, the inflammation associated with an implant is a local inflammation or a systemic inflammatory reaction. In some aspects, the implant is a silicone, a saline, a metal, a plastic, or a polymeric implant. In some aspects, the implant is a cosmetic implant, a prosthetic implant, a subdermal implant, a transdermal implant, a bone replacement implant, or a bone fracture repair device. In some aspects, the implant is a drug delivery implant or a drug release implant. In other aspects, the implant is an artificial joint, an artificial heart, an artificial heart valve, a testicular prosthesis, a breast implant, a dental implant, an ocular implant, a cochlear implant, a penile implant, a cardiac implant, a catheter, an implantable urinary continence device, a pacemaker, an electrode, a Hernia support device, or a respirator tube.

In some aspects, the disclosure provides a method of inhibiting or preventing migration of an inflammatory cell (e.g., a monocyte or neutrophil), comprising administering to a subject in need thereof a therapeutically effective amount of an antibody or antigen binding fragment described herein. In some aspects, the disclosure provides a method of inhibiting or preventing migration of an inflammatory cell (e.g., a monocyte or neutrophil), comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of inhibiting or preventing migration of an inflammatory cell (e.g., a monocyte or neutrophil), comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the disclosure provides a method of treating or preventing nonalcoholic fatty liver disease (NAFLD), steatohepatitis, or nonalcoholic steatohepatitis (NASH), comprising administering to a subject in need thereof a therapeutically effective amount of an antibody or antigen binding fragment described herein. In some aspects, the disclosure provides a method of treating or preventing nonalcoholic fatty liver disease (NAFLD), steatohepatitis, or nonalcoholic steatohepatitis (NASH), comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing nonalcoholic fatty liver disease (NAFLD), steatohepatitis, or nonalcoholic steatohepatitis (NASH), comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the disclosure provides a method of treating or preventing fibrosis, comprising administering to a subject in need thereof a therapeutically effective amount of an antibody or antigen binding fragment described herein. In some aspects, the disclosure provides a method of treating or preventing fibrosis, comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing fibrosis, comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the fibrosis is liver fibrosis, kidney fibrosis, lung fibrosis (pulmonary fibrosis), skin fibrosis, idiopathic pulmonary fibrosis (IPF), cystic fibrosis, progressive massive fibrosis, cirrhosis, endomyocardial fibrosis, mediastinal fibrosis, myelofibrosis, retroperitoneal fibrosis, nephrogenic systemic fibrosis, or arthrofibrosis. In some aspects, the kidney fibrosis is focal segmental glomerulosclerosis (FSGS) or glomerulosclerosis.

In some aspects, the disclosure provides a method of treating or preventing arthritis (e.g., rheumatoid arthritis or psoriatic arthritis), comprising administering to a subject in need thereof a therapeutically effective amount of an antibody or antigen binding fragment described herein. In some aspects, the disclosure provides a method of treating or preventing arthritis (e.g., rheumatoid arthritis or psoriatic arthritis), comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing arthritis (e.g., rheumatoid arthritis or psoriatic arthritis), comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the arthritis is rheumatoid arthritis, osteoarthritis, juvenile arthritis, or psoriatic arthritis. In some aspects, the rheumatoid arthritis is chronic rheumatoid arthritis or juvenile rheumatoid arthritis.

In some aspects, the disclosure provides a method of treating or preventing multiple sclerosis, comprising administering to a subject in need thereof a therapeutically effective amount of an antibody or antigen binding fragment described herein. In some aspects, the disclosure provides a method of treating or preventing multiple sclerosis, comprising administering to a subject in need thereof a therapeutically effective amount of an antibody or antigen binding fragment, comprising
  (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;
  (ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;
  (iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;
  (iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;
  (v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and
  (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing multiple sclerosis, comprising administering to a subject in need thereof a therapeutically effective amount of an antibody or antigen binding fragment thereof that specifically binds to MOSPD2, comprising
  (i) a heavy chain CDR1 comprising the amino acid sequence of SEQ ID NO:1 or a sequence having one or more conservative substitutions in SEQ ID NO:1;
  (ii) a heavy chain CDR2 comprising the amino acid sequence of any one of SEQ ID NOs:2-8 or a sequence having one or more conservative substitutions in SEQ ID NOs:2-8;
  (iii) a heavy chain CDR3 comprising the amino acid sequence of SEQ ID NO:9 or a sequence having one or more conservative substitutions in SEQ ID NO:9;
  (iv) a light chain CDR1 comprising the amino acid sequence of any one of SEQ ID NOs:10-18 or a sequence having one or more conservative substitutions in any one of SEQ ID NOs:10-18;
  (v) a light chain CDR2 comprising the amino acid sequence of any one of SEQ ID NOs:19-24 or a sequence having one or more conservative substitutions in any one of SEQ ID NOs:19-24; and
  (vi) a light chain CDR3 comprising the amino acid sequence of SEQ ID NO:25 or a sequence having one or more conservative substitutions in SEQ ID NO:25.

In some aspects, the multiple sclerosis is relapsing remitting multiple sclerosis (RRMS), primary progressive multiple sclerosis (PPMS), or secondary progressive multiple sclerosis (SPMS). In some aspects, the method further comprises administering to the subject an additional therapeutic agent. In some aspects, the method comprises an additional therapeutic agent is teriflunomide, natalizumab, dimethyl fumarate, ocrelizumab, IFNβ-1a, cladribine, glatiramer acetate, or a combination thereof.

In some aspects, the disclosure provides a method of treating or preventing colitis or inflammatory bowel disease, comprising administering to a subject in need thereof a therapeutically effective amount of an antibody or antigen binding fragment described herein. In some aspects, the disclosure provides a method of treating or preventing colitis or inflammatory bowel disease, comprising administering to a subject in need thereof a therapeutically effective amount of an antibody or antigen binding fragment, comprising
  (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;
  (ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;
  (iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;
  (iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;
  (v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and
  (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing colitis or inflammatory bowel disease, comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the inflammatory bowel disease is ulcerative colitis or Crohn's disease. In some aspects, the method further comprises administering to the subject an additional therapeutic agent. In some aspects, the additional therapeutic agent is infliximab, vedolizumab, azathioprine, adalimumab, masalazine, or a combination thereof.

In some aspects, the disclosure provides a method of treating or preventing cancer or metastasis of cancer, comprising administering to a subject in need thereof a therapeutically effective amount of an antibody or antigen binding fragment described herein. In some aspects, the disclosure provides a method of treating or preventing cancer or metastasis of cancer, comprising administering to a subject in need thereof a therapeutically effective amount of an antibody or antigen binding fragment, comprising (i) a heavy chain CDR1 comprising the amino acid sequence of SEQ ID NO:1 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:1;

(ii) a heavy chain CDR2 comprising the amino acid sequence of any one of SEQ ID NOs:2-8 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:2-8;

(iii) a heavy chain CDR3 comprising the amino acid sequence of SEQ ID NO:9 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:9;

(iv) a light chain CDR1 comprising the amino acid sequence of any one of SEQ ID NOs:10-18 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:10-18;

(v) a light chain CDR2 comprising the amino acid sequence of any one of SEQ ID NOs:19-24 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to any one of SEQ ID NOs:19-24; and (vi) a light chain CDR3 comprising the amino acid sequence of SEQ ID NO:25 or a sequence having about 80%, 81%, 82%, 83%, 84%, 85%, 86%, 87%, 88%, 89%, 90%, 91%, 92%, 93%, 94%, 95%, 96%, 97%, 98%, or 99% or greater identity to SEQ ID NO:25.

In some aspects, the disclosure provides a method of treating or preventing cancer or metastasis of cancer, comprising administering to a subject in need thereof a therapeutically effective amount of an antibody or antigen binding fragment thereof that specifically binds to MOSPD2, comprising (i) a heavy chain CDR1 comprising the amino acid sequence of SEQ ID NO:1 or a sequence having one or more conservative substitutions in SEQ ID NO:1;

(ii) a heavy chain CDR2 comprising the amino acid sequence of any one of SEQ ID NOs:2-8 or a sequence having one or more conservative substitutions in SEQ ID NOs:2-8;

(iii) a heavy chain CDR3 comprising the amino acid sequence of SEQ ID NO:9 or a sequence having one or more conservative substitutions in SEQ ID NO:9;

(iv) a light chain CDR1 comprising the amino acid sequence of any one of SEQ ID NOs:10-18 or a sequence having one or more conservative substitutions in any one of SEQ ID NOs:10-18;

(v) a light chain CDR2 comprising the amino acid sequence of any one of SEQ ID NOs:19-24 or a sequence having one or more conservative substitutions in any one of SEQ ID NOs:19-24; and (vi) a light chain CDR3 comprising the amino acid sequence of SEQ ID NO:25 or a sequence having one or more conservative substitutions in SEQ ID NO:25.

In some aspects, the cancer is bladder cancer, breast cancer, colon cancer, ovarian cancer, rectal cancer, kidney cancer, liver cancer, lung cancer, esophageal cancer, gall bladder cancer, ovarian cancer, pancreatic cancer, stomach cancer, cervical cancer, thyroid cancer, prostate cancer, skin cancer, hematopoietic cancer, cancer of mesenchymal origin, cancer of central or peripheral nervous system, endometrial cancer, head and neck cancer, glioblastoma, malignant ascites, neuroendocrine cancer, gastrointestinal cancer, or recurrent or primary cancers.

In some aspects, the lung cancer is a small-cell lung cancer or a non-small-cell lung cancer.

In some aspects, the skin cancer is squamous cell carcinoma, basal cell cancer, melanoma, dermatofibrosarcoma protuberans, Merkel cell carcinoma, Kaposi's sarcoma, keratoacanthoma, spindle cell tumors, sebaceous carcinomas, microcystic adnexal carcinoma, Paget's disease of the breast, atypical fibroxanthoma, leiomyosarcoma, or angiosarcoma.

In some aspects, the hematopoietic cancer is a hematopoietic cancer of lymphoid lineage. In some aspects, the hematopoietic cancer of lymphoid lineage is leukemia, acute lymphocytic leukemia, chronic lymphocytic leukemia, acute lymphoblastic leukemia, B-cell lymphoma, T-cell-lymphoma, Hodgkin's lymphoma, non-Hodgkin's lymphoma, hairy cell lymphoma or Burkitt's lymphoma.

In some aspects, the hematopoietic cancer is a hematopoietic cancer of myeloid lineage. In some aspects, the hematopoietic cancer of myeloid lineage is acute myelogenous leukemia, chronic myelogenous leukemia, myelodysplastic syndrome, and promyelocytic leukemia.

In some aspects, the cancer of mesenchymal origin is fibrosarcoma, rhabdomyosarcoma, soft tissue sarcoma, or bone sarcoma.

In some aspects, the cancer of the central or peripheral nervous system is astrocytoma, neuroblastoma, glioma, schwannomas, or glioblastoma.

In some aspects, the cancer is anal cancer, bone cancer, gastrointestinal stomal cancer, gestational trophoblastic disease, Hodgkin's lymphoma, Kaposi sarcoma, keratoacanthoma, malignant mesothelioma, multicentric castleman disease, multiple myeloma and other plasma cell neoplasms, myeloproliferative neoplasms, neuroblastoma, non-Hodgkin's lymphoma, osteosarcoma, ovarian, fallopian tube, or primary peritoneal cancer, penile cancer, retinoblastoma, rhabdomyosarcoma, seminoma, soft tissue sarcoma, stomach (gastric) cancer, testicular cancer, teratocarcinoma, thyroid follicular cancer, vaginal cancer, vulvar cancer, Wilms tumor and other childhood kidney cancers, or xeroderma pigmentosum.

In some aspects, the method further comprises administering to the subject an additional therapeutic agent. In some aspects, the additional therapeutic agent is an anticancer agent. In some aspects, the anticancer agent is Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Akynzeo (Netupitant and Palonosetron Hydrochloride), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Becenum (Carmustine), Beleodaq (Belinostat), Belinostat, Bendamustine Hydrochloride, BEP, Bevacizumab, Bexarotene, Bexxar (Tositumomab and I 131 Iodine Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPDX, Carboplatin, Carboplatin-Taxol, Carfilzomib, Carmubris (Carmustine), Carmustine, Carmustine Implant, Casodex (Bicalutamide), CeeNU (Lomustine), Ceritinib, Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, CMF, Cometriq (Cabozantinib-S-Malate), COPP, COPP-ABV, Cosmegen (Dactinomycin), Crizotinib, CVP, Cyclophosphamide, Cyfos (Ifosfamide), Cyramza (Ramucirumab), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folflox, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Keytruda (Pembrolizumab), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Netupitant and Palonosetron Hydrochloride, Neupogen (Filgrastim), Nexavar (Sorafenib Tosylate), Nilotinib, Nivolumab, Nolvadex (Tamoxifen Citrate), Nplate (Romiplostim), Obinutuzumab, OEPA, Ofatumumab, OFF, Olaparib, Omacetaxine Mepesuccinate, Oncaspar (Pegaspargase), Ontak (Denileukin Diftitox), Opdivo (Nivolumab), OPPA, Oxaliplatin, Paclitaxel, Paclitaxel Albumin-stabilized Nanoparticle Formulation, PAD, Palbociclib, Palifermin, Palonosetron Hydrochloride, Pamidronate Disodium, Panitumumab, Panobinostat, Paraplat (Carboplatin), Paraplatin (Carboplatin), Pazopanib Hydrochloride, Pegaspargase, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, R-EPOCH, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Siltuximab, Sipuleucel-T, Somatuline Depot (Lanreotide Acetate), Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synovir (Thalidomide), Synribo (Omacetaxine Mepesuccinate), TAC, Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Tositumomab and I 131 Iodine Tositumomab, Totect (Dexrazoxane Hydrochloride), TPF, Trametinib, Trastuzumab, Treanda (Bendamustine Hydrochloride), Trisenox (Arsenic Trioxide), Tykerb (Lapatinib Ditosylate), Unituxin (Dinutuximab), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), or Zytiga (Abiraterone Acetate).

In some aspects of any of the methods described herein, the subject is a human. In some aspects, the subject is a mammal. In some aspects, the subject is a veterinary animal (e.g., a dog, cat, bird, mouse, horse, sheep, cow, goat, or the like).

EXAMPLES

Reference is now made to the following examples, which together with the above descriptions illustrate some aspects of the disclosure in a non-limiting fashion.

Example 1

Anti-MOSPD2 Antibodies

Anti-MOSPD2 monoclonal antibodies were generated according to the following methods. For each antibody, an endotoxin-free DNA preparation of the heavy and light chain was introduced into the pTXs1 expression construct. By using a proprietary Xten transfection protocol, the plasmids were then transiently transfected in the proprietary XtenCHO cells (80 ml-culture). Culture medium samples were collected when the viability dropped <50% (14 days post-transfection), and the antibodies were then purified on a protein G resin by using the following standard method: (i) clarification by 0.22 μm filtration, (ii) equilibration, binding, and washing with phosphate buffered saline (PBS) pH 7.5, (iii) elution by pH shift with Tris-Glycine pH 2.7, (iv) neutralization with Tris-Hydrochloride (Tris-HCl) pH 8.5, and (v) pool of the fractions of interest and buffer exchange vs. PBS pH 7.5. Yields were estimated using Octet RED95 instrument. Purity was determined based on non-reduced sodium dodecyl sulfate polyacrylamide gel electrophoresis (SDS-PAGE). The antibodies generated are listed in Table 2.

TABLE 2

Anti-MOSPD2 Antibodies

| # | VH CDR1 | VH CDR2 | VH CDR3 | VL CDR1 | VL CDR2 | VL CDR3 |
|---|---|---|---|---|---|---|
| (1) | SYSMS | TISRGGSYTYYPDSVKG | GK | KSSQSLLDSDGKTNLN | LVSKLDS | WQGTHFPRT |
| S2 (2) | SYSMS | TISRGGSYTYYPDSVKG | GK | KSSQSLVDSDAKTNLN | LVSKRDS | WQGTHFPRT |
| S3 (3) | SYSMS | TISRGGSYTYYPDSVKG | GK | RSSQSLVDSDAKTNLN | LVSNRDS | WQGTHFPRT |
| S4 (4) | SYSMS | TISRSSSYIYYADSVKG | GK | KSSQSLLDSDGKTNLN | LVSKLDS | WQGTHFPRT |
| S5 (5) | SYSMS | TISRSSSYIYYADSVKG | GK | KSSQSLVDSDAKTNLN | LVSKRDS | WQGTHFPRT |
| S6 (6) | SYSMS | TISRSSSYIYYADSVKG | GK | RSSQSLVDSDAKTNLN | LVSNRDS | WQGTHFPRT |
| S10 (7) | SYSMS | TISRGGSNKYYADSVKG | GK | KSSQSLLDSDGKTNLN | LVSKLDS | WQGTHFPRT |
| S11 (8) | SYSMS | TISRGGSNKYYADSVKG | GK | KSSQSLVDSDAKTNLN | LVSKRDS | WQGTHFPRT |
| S12 (9) | SYSMS | TISRGGSNKYYADSVKG | GK | RSSQSLVDSDAKTNLN | LVSNRDS | WQGTHFPRT |

TABLE 2-continued

Anti-MOSPD2 Antibodies

| # | VH CDR1 | VH CDR2 | VH CDR3 | VL CDR1 | VL CDR2 | VL CDR3 |
|---|---------|---------|---------|---------|---------|---------|
| S16 (10) | SYSMS | TISRSGGSTSYAQKVQG | GK | KSSQSLLDSDGKTNLN | LVSKLDS | WQGTHFPRT |
| S17 (11) | SYSMS | TISRSGGSTSYAQKVQG | GK | KSSQSLVDSDAKTNLN | LVSKRDS | WQGTHFPRT |
| S18 (12) | SYSMS | TISRSGGSTSYAQKVQG | GK | RSSQSLVDSDAKTNLN | LVSNRDS | WQGTHFPRT |
| S10N (13) | SYSMS | TISRGGSNKYYAESVKG | GK | KSSQSLLESEGKTNLN | LVSKLES | WQGTHFPRT |
| S11N (14) | SYSMS | TISRGGSNKYYAESVKG | GK | KSSQSLVESEGKTNLN | LVSKRES | WQGTHFPRT |
| M1 (15) | SYSMS | TISRGGSYTYYPESVKG | GK | KSSQSLLDSDGKTNLN | LVSKLDS | WQGTHFPRT |
| M2 (16) | SYSMS | TISRGGSYTYYPDTVKG | GK | KSSQSLLDSDGKTNLN | LVSKLDS | WQGTHFPRT |
| M3 (17) | SYSMS | TISRGGSYTYYPDSVKG | GK | KSSQSLLESDGKTNLN | LVSKLDS | WQGTHFPRT |
| M4 (18) | SYSMS | TISRGGSYTYYPDSVKG | GK | KSSQSLLDTDGKTNLN | LVSKLDS | WQGTHFPRT |
| M5 (19) | SYSMS | TISRGGSYTYYPDSVKG | GK | KSSQSLLDSEGKTNLN | LVSKLDS | WQGTHFPRT |
| M6 (20) | SYSMS | TISRGGSYTYYPDSVKG | GK | KSSQSLLDSDAKTNLN | LVSKLDS | WQGTHFPRT |
| M7 (21) | SYSMS | TISRGGSYTYYPDSVKG | GK | KSSQSLLDSDGKTNLN | LVSKLES | WQGTHFPRT |
| M8 (22) | SYSMS | TISRGGSYTYYPDSVKG | GK | KSSQSLLDSDGKTNLN | LVSKLDT | WQGTHFPRT |
| c56-23-13 S1 (23) | SYSMS | TISRGGSYTYYPESVKG | GK | KSSQSLLDSDGKTNLN | LVSKLDT | WQGTHFPRT |
| c56-23-13 S2 (24) | SYSMS | TISRGGSYTYYPESVKG | GK | KSSQSLLDSDGKTNLN | LVSKLES | WQGTHFPRT |
| c56-23-13 S3 (25) | SYSMS | TISRGGSYTYYPESVKG | GK | KSSQSLLESDGKTNLN | LVSKLDT | WQGTHFPRT |
| c56-23-13 S4 (26) | SYSMS | TISRGGSYTYYPESVKG | GK | KSSQSLLESDGKTNLN | LVSKLES | WQGTHFPRT |
| c56-23-13 S5 (27) | SYSMS | TISRGGSYTYYPESVKG | GK | KSSQSLLDSEGKTNLN | LVSKLDT | WQGTHFPRT |
| c56-23-13 S6 (28) | SYSMS | TISRGGSYTYYPESVKG | GK | KSSQSLLDSEGKTNLN | LVSKLES | WQGTHFPRT |
| c56-23-13 S7 (29) | SYSMS | TISRGGSYTYYPESVKG | GK | KSSQSLLESEGKTNLN | LVSKLDT | WQGTHFPRT |
| c56-23-13 S8 (30) | SYSMS | TISRGGSYTYYPESVKG | GK | KSSQSLLESEGKTNLN | LVSKLES | WQGTHFPRT |

The KD of the anti-MOSPD2 antibodies was determined using Biacore T200. The antigen (10 µg/ml) was immobilized on a CM5 sensor chip. A solution containing antibodies at 2-fold increasing concentrations (1-32 nM) was flown over the CM5 chip. Response captured over time was showing the progress of the interaction and association/dissociation cycle. The kinetics parameters and affinity were calculated using BIAevaluation software. The values obtained are listed in Table 3.

TABLE 3

Binding Properties of Anti-MOSPD2 Antibodies

| Antibody | ka (1/Ms) | kd (1/s) | KD (M) |
|---|---|---|---|
| (1) | $4.892 \times 10^5$ | $1.936 \times 10^{-4}$ | $3.958 \times 10^{-10}$ |
| S4 (4) | $2.008 \times 10^5$ | $5.757 \times 10^{-4}$ | $2.868 \times 10^{-9}$ |
| S5 (5) | $3.259 \times 10^5$ | $7.465 \times 10^{-4}$ | $2.290 \times 10^{-9}$ |
| S6 (6) | $6.699 \times 10^5$ | 0.004452 | $6.646 \times 10^{-9}$ |
| S10 (7) | $3.310 \times 10^5$ | $5.386 \times 10^{-4}$ | $1.627 \times 10^{-9}$ |
| S11 (8) | $7.598 \times 10^5$ | $8.554 \times 10^{-4}$ | $1.126 \times 10^{-9}$ |
| S12 (9) | $1.146 \times 10^6$ | 0.006540 | $5.708 \times 10^{-9}$ |
| S16 (10) | $3.782 \times 10^5$ | 0.001048 | $2.770 \times 10^{-9}$ |
| S17 (11) | $2.177 \times 10^5$ | 0.001312 | $6.027 \times 10^{-9}$ |
| S18 (12) | $1.977 \times 10^6$ | 0.001421 | $7.188 \times 10^{-10}$ |
| S11-N (14) | $6.826 \times 10^6$ | 0.3799 | $5.565 \times 10^{-8}$ |
| M1 (15) | $2.391 \times 10^6$ | 0.001147 | $4.797 \times 10^{-10}$ |
| M2 (16) | $2.173 \times 10^6$ | 0.001462 | $6.730 \times 10^{-10}$ |
| M3 (17) | $2.464 \times 10^6$ | 0.002899 | $1.177 \times 10^{-9}$ |
| M4 (18) | $1.147 \times 10^6$ | 0.001802 | $1.571 \times 10^{-9}$ |
| M5 (19) | $1.526 \times 10^6$ | 0.001388 | $9.094 \times 10^{-10}$ |
| M6 (20) | $1.053 \times 10^6$ | 0.001921 | $1.824 \times 10^{-9}$ |
| M7 (21) | $1.885 \times 10^6$ | 0.006983 | $3.704 \times 10^{-9}$ |
| M8 (22) | $2.068 \times 10^6$ | 0.001516 | $7.328 \times 10^{-10}$ |
| c56-23-13 S1 (23) | $1.070 \times 10^6$ | $3.162 \times 10^{-4}$ | $2.954 \times 10^{-10}$ |
| c56-23-13 S2 (24) | $1.969 \times 10^6$ | 0.001797 | $9.126 \times 10^{-10}$ |
| c56-23-13 S3 (25) | $2.348 \times 10^6$ | $7.419 \times 10^{-4}$ | $3.160 \times 10^{-10}$ |
| c56-23-13 S4 (26) | $3.049 \times 10^6$ | 0.002253 | $7.391 \times 10^{-10}$ |
| c56-23-13 S5 (27) | $9.349 \times 10^5$ | $3.853 \times 10^{-4}$ | $4.122 \times 10^{-10}$ |
| c56-23-13 S6 (28) | $1.546 \times 10^6$ | 0.001771 | $1.145 \times 10^{-9}$ |
| c56-23-13 S7 (29) | $2.913 \times 10^6$ | $7.751 \times 10^{-4}$ | $2.661 \times 10^{-10}$ |
| c56-23-13 S8 (30) | $3.503 \times 10^6$ | 0.002513 | $7.173 \times 10^{-10}$ |

Example 2

Binding of Anti-MOSPD2 Antibodies to Surface Expressed Human MOSPD2

A study was performed to evaluate the binding of anti-MOSPD2 antibodies (i.e., antibody S11 (#8) in Table 2 of Example 1) to MOSPD2 in its native form in human monocytes. For that, red blood cells were lysed from 250 µl of human peripheral blood. Leukocytes were stained with an isotype control antibody or 2 µg of anti-MOSPD2 antibody, followed by incubation with FITC conjugated anti-CD14 antibody (1 µg) for gating on monocytes and a secondary APC conjugated anti-human Fcγ antibody (1:200). Analysis was performed by flow cytometry. The results in FIG. 1 gated on CD14 positive cells show that anti-MOSPD2 antibody binds surface expressed MOSPD2 on human monocytes.

Example 3

Binding Affinities of Anti-MOSPD2 Antibodies

A study to determine the binding affinity profile an anti-MOSPD2 antibodies (i.e., antibody S11 (#8) in Table 2 of Example 1) was conducted. For this, human MOSPD2 (10 µg/ml) was immobilized on CM5 sensor chip. Anti-MOSPD2 antibody at 1, 2, 4, 8, and 16 nM was contacted over the CM5 chip and the response was captured over time, showing the progress of the interaction and association/dissociation cycle. Regeneration between different antibody concentrations was performed to remove all remaining bound antibody from chip. The kinetics parameters and affinity were calculated using BIAevaluation software.

Figure 2:
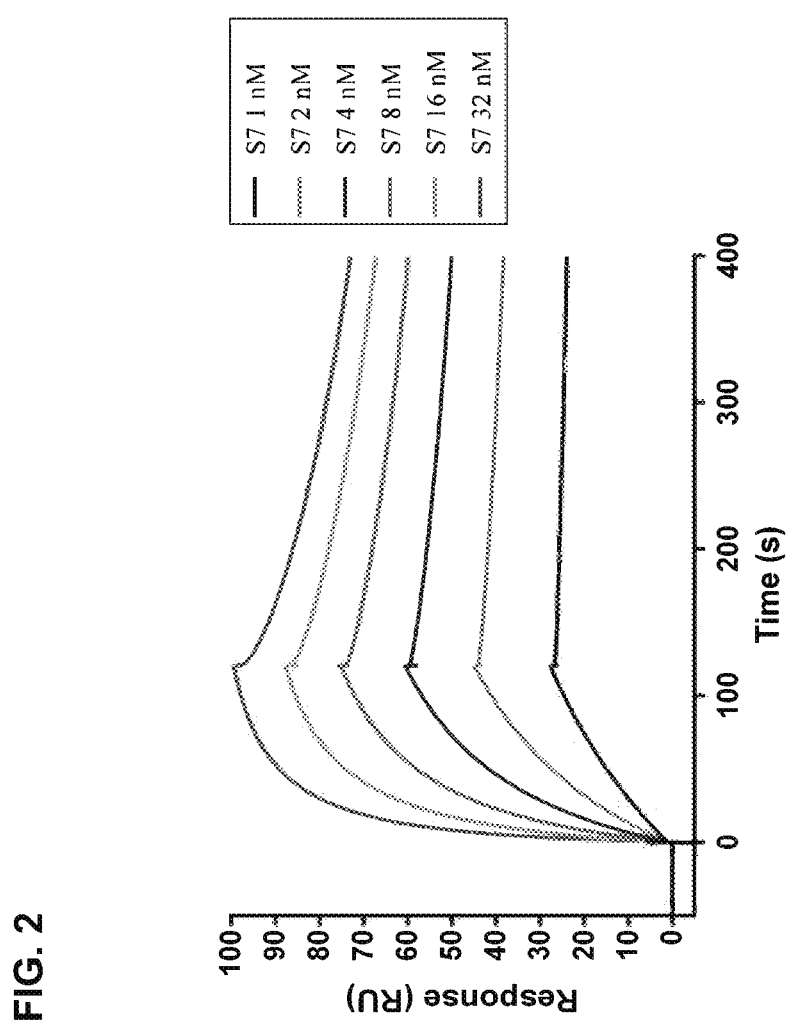
FIG. 2 (FIG. 2) shows a sensorgram plot of binding to human MOSPD2 with 1-16 nM of anti-MOSPD2 antibody.

The results show that the anti-MOSPD2 antibody binds to MOSPD2 with a Ka value of $9.51 \times 10^5$, Kd value of $1.32 \times 10^{-3}$ and a calculated KD of $1.39 \times 10^{-9}$ M. In addition, a sensorgram showed a dose-response relationship with smooth and consistent curves (FIG. 2).

Example 4

In-Vitro Dose Ranging Efficacy and EC50 for Anti-MOSPD2 Antibodies

Figure 3A:
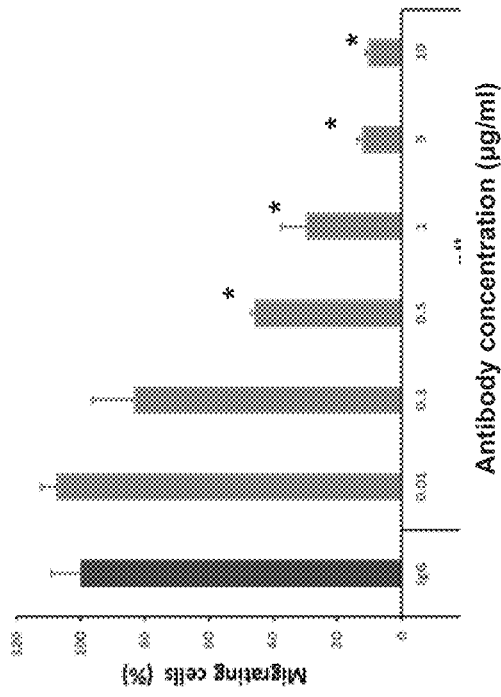
FIG. 3A (FIG. 3A) shows dose response inhibition of monocyte migration with increasing dose of anti-MOSPD2 antibody. The results shown are means of triplicate experiments ±standard deviation. * $p<0.001$ FIG. 3B (FIG. 3B) shows the calculation of EC50 based on the results in Example 4.
Figure 3B:
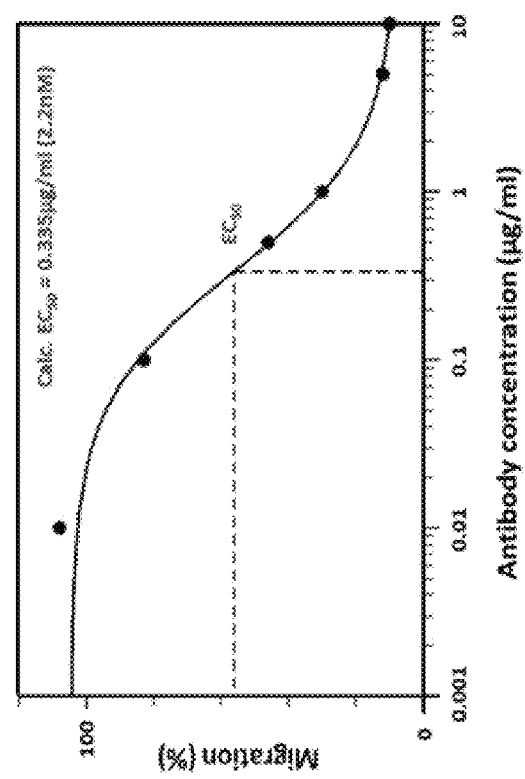

Experiments were conducted to demonstrate dose ranging efficacy and determine the concentration in which anti-MOSPD2 antibodies affect monocyte migration by half of maximal response, i.e., $EC_{50}$. SDF-1 and MCP-1 (100 ng/ml) were placed in the lower chamber of a QCM 24-well migration assay plate. Human primary monocytes ($3 \times 10^5$) were pre-incubated for 30 min with 0.01, 0.1, 0.5, 1, 5 or 10 µg/ml anti-MOSPD2 antibody or with 10 µg/ml of an IgG1 control antibody. Monocytes were then seeded in the upper chamber for 3 h, after which the number of cells that migrated to the lower compartment was determined by fluorescence-activated cell sorting (FACS). The data in FIGS. 3A-3B demonstrate that significant inhibition of migration could be reached at a dose as low as 0.5 µg/ml. Moreover, the $EC_{50}$ for the antibody was in the low nM range.

Example 5

In-Vitro Efficacy Studies with Variants of Anti-MOSPD2 Antibodies

Figure 4A:
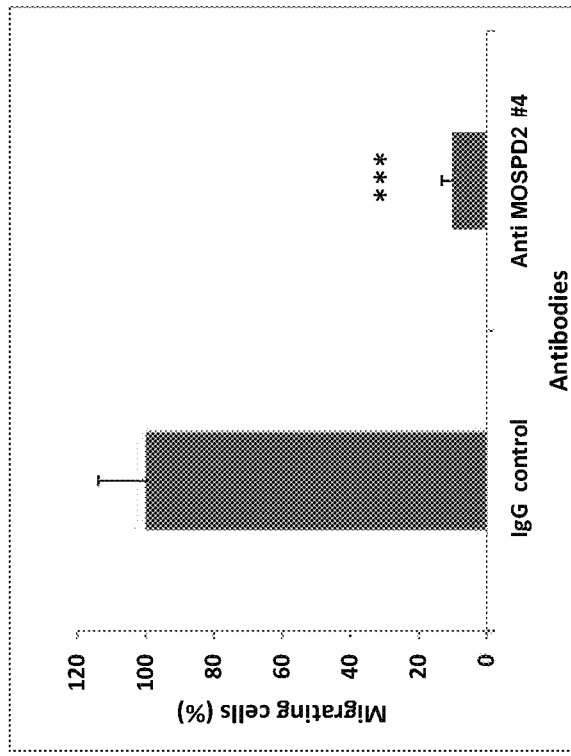
FIGS. 4A-4BB (FIGS. 4A-4BB) shows several anti-MOSPD2 antibody variants that significantly inhibit monocyte migration. Results shown are mean of triplicate experiments ±standard deviation. * $p<0.05$,  $p<0.01$, * $p<0.001$.
Figure 4B:
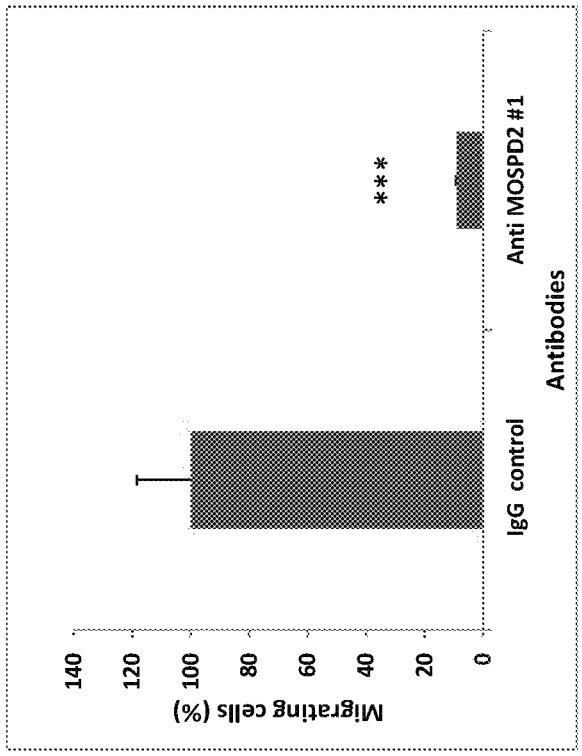
Figure 4D:
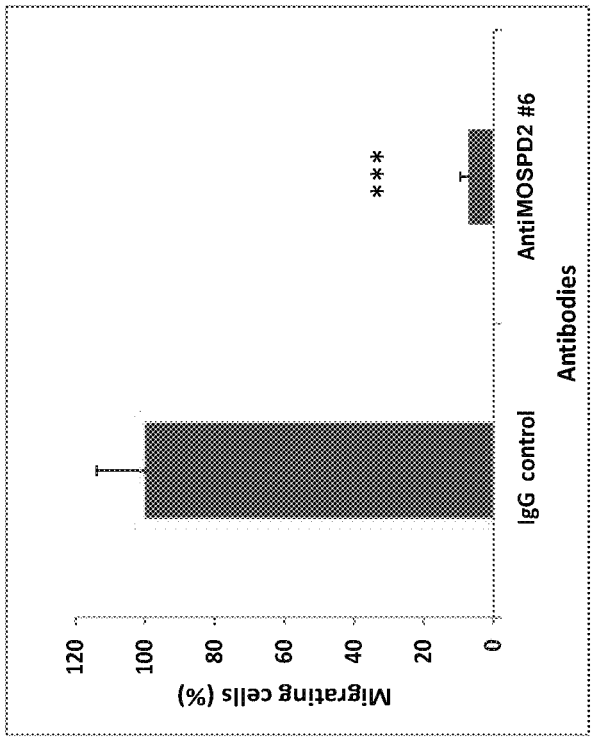
Figure 4C:
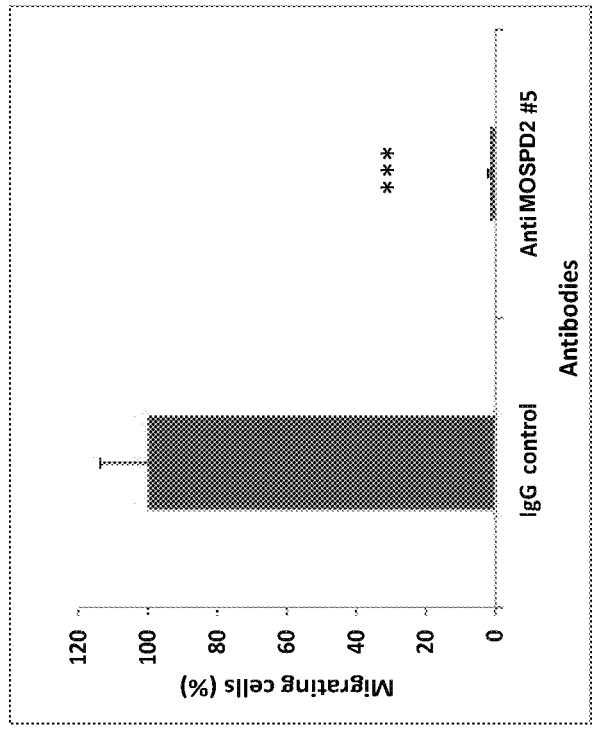
Figure 4E:
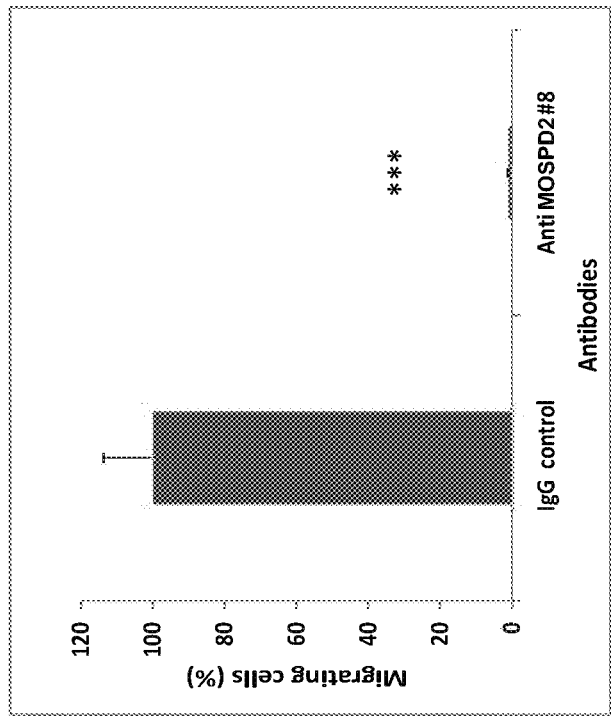
Figure 4F:
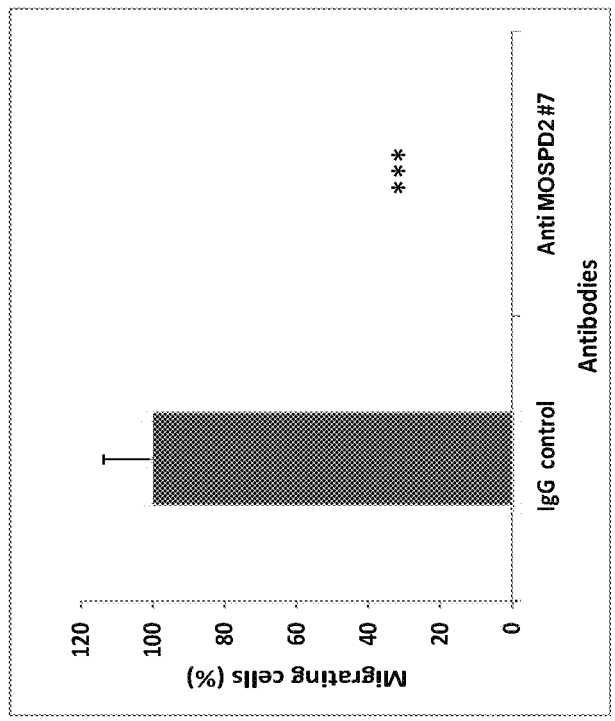
Figure 4H:
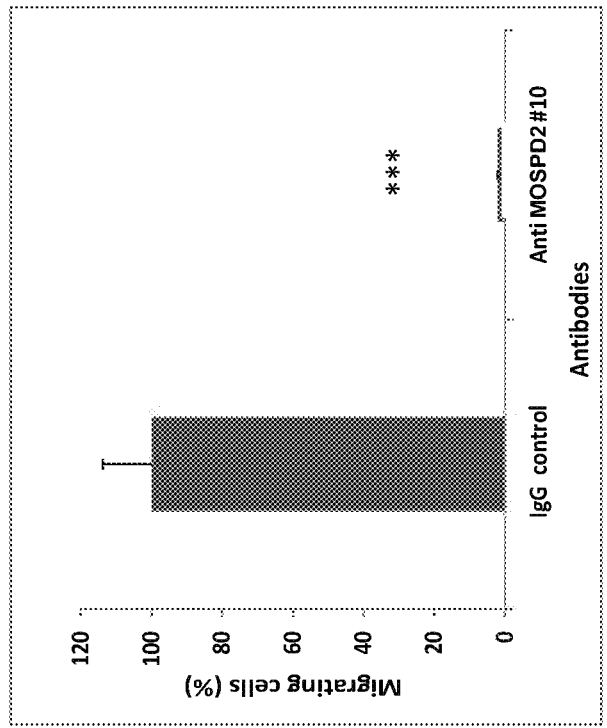
Figure 4G:
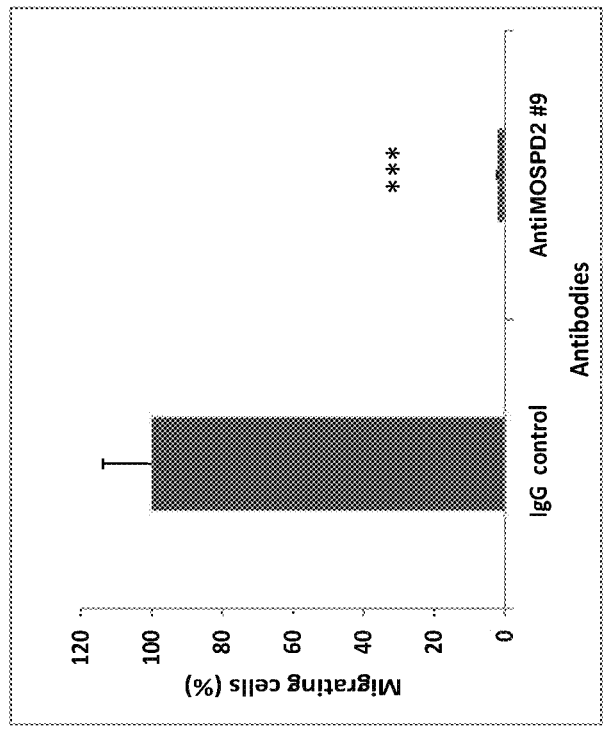
Figure 4J:
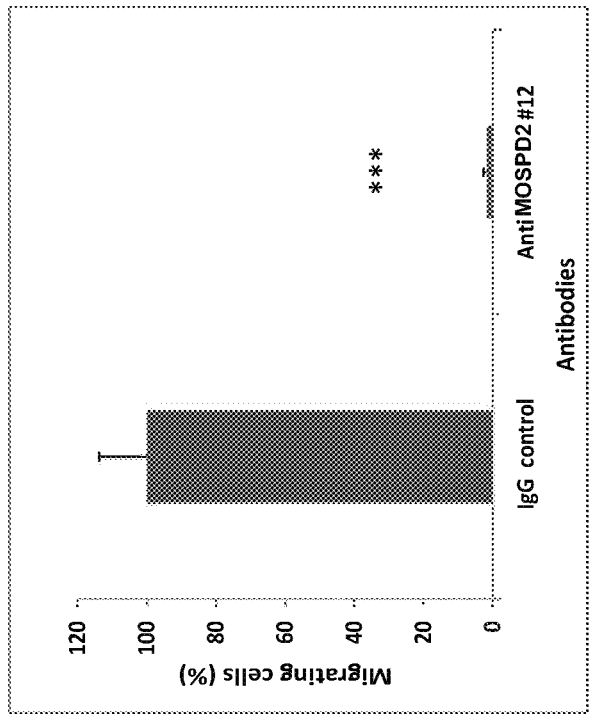
Figure 4I:
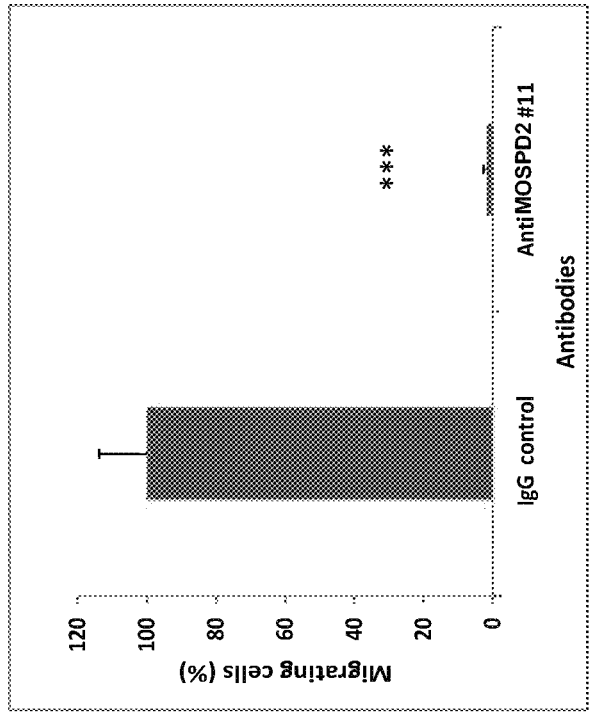
Figure 4N:
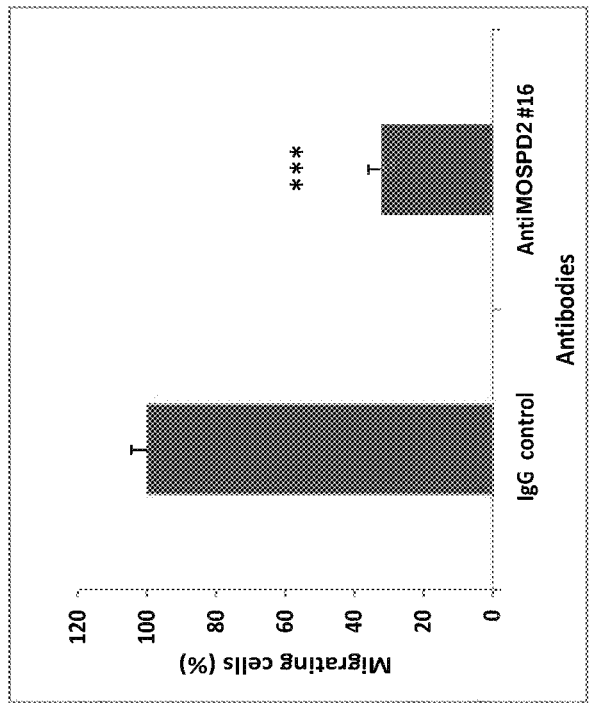
Figure 4M:
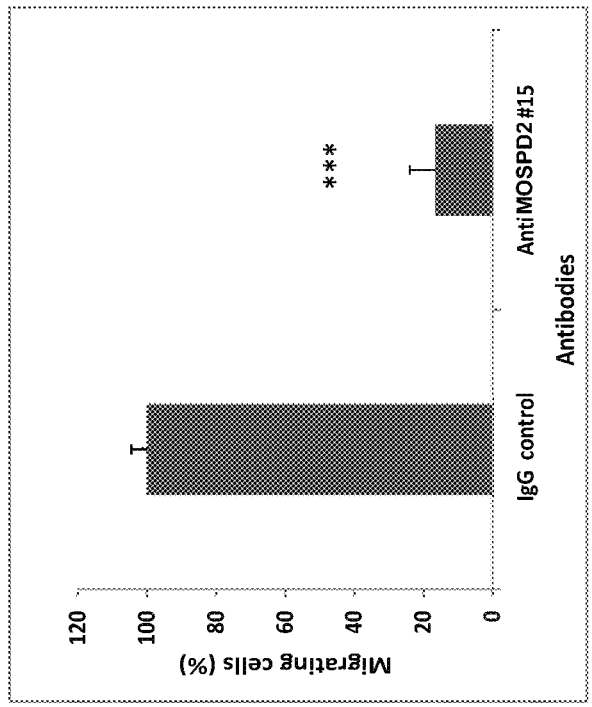
Figure 4P:
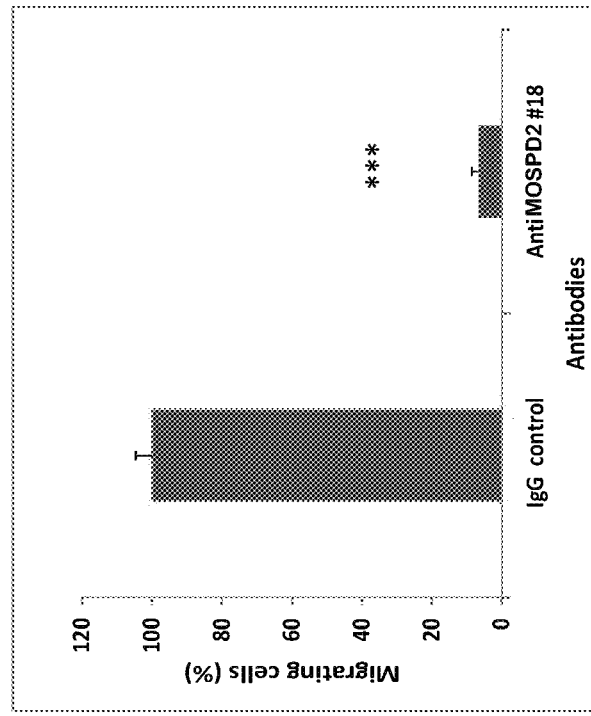
Figure 4O:
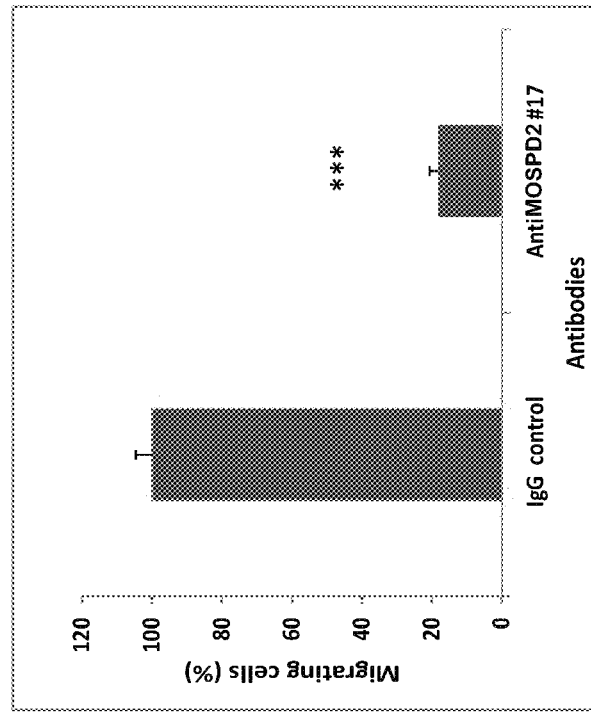
Figure 4Q:
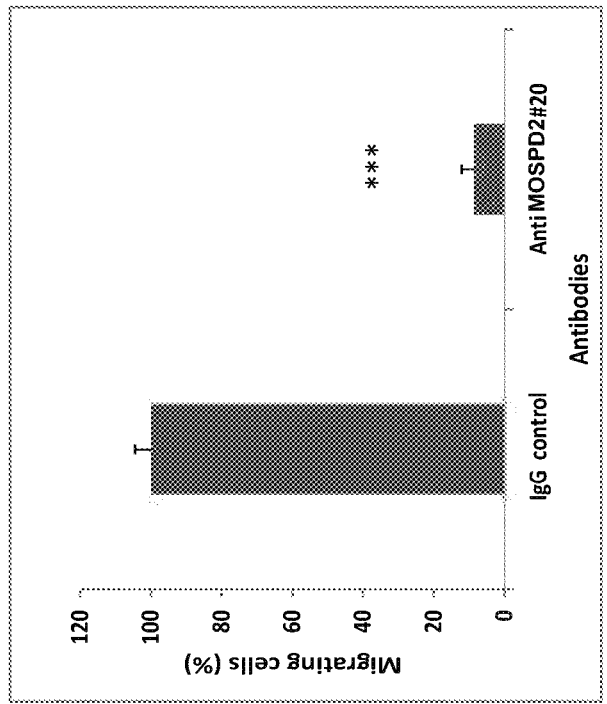
Figure 4R:
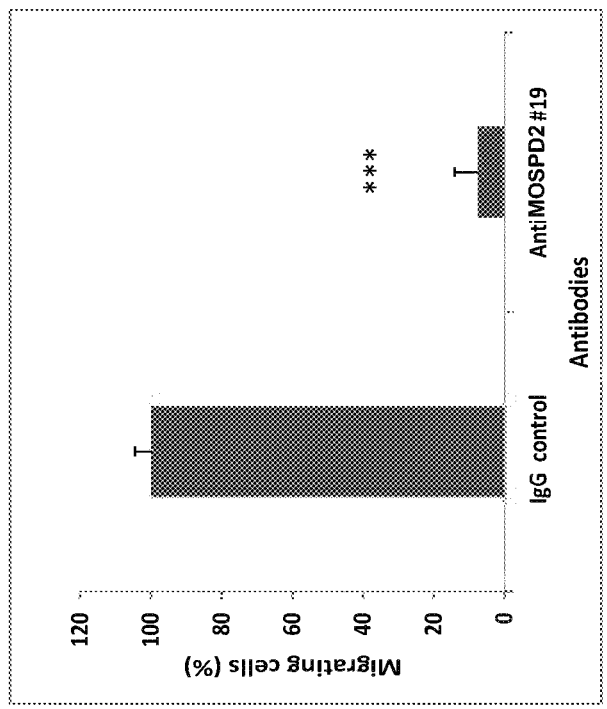
Figure 4T:
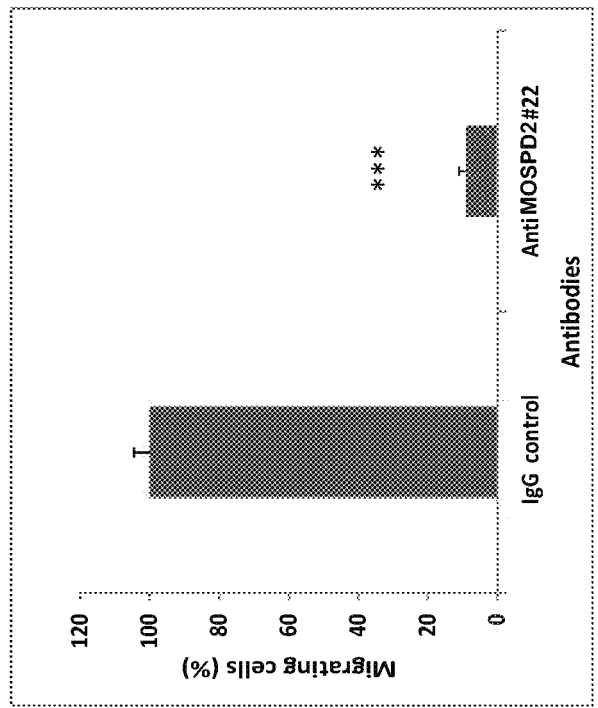
Figure 4S:
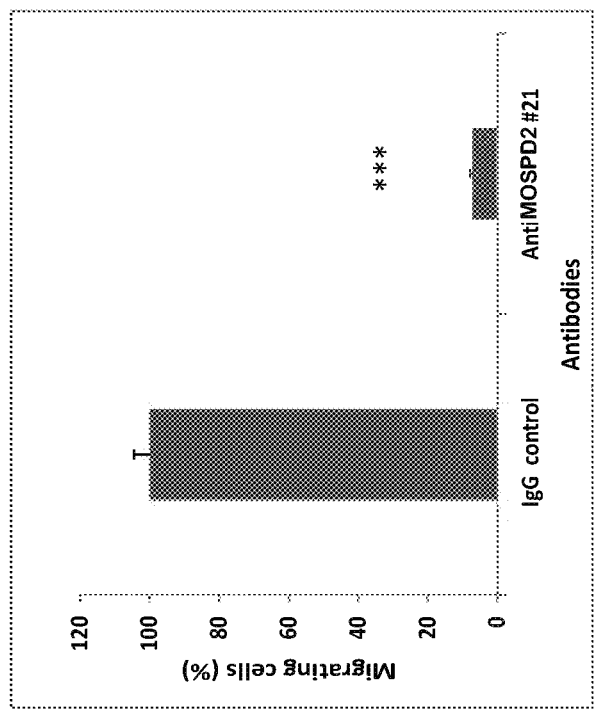
Figure 4X:
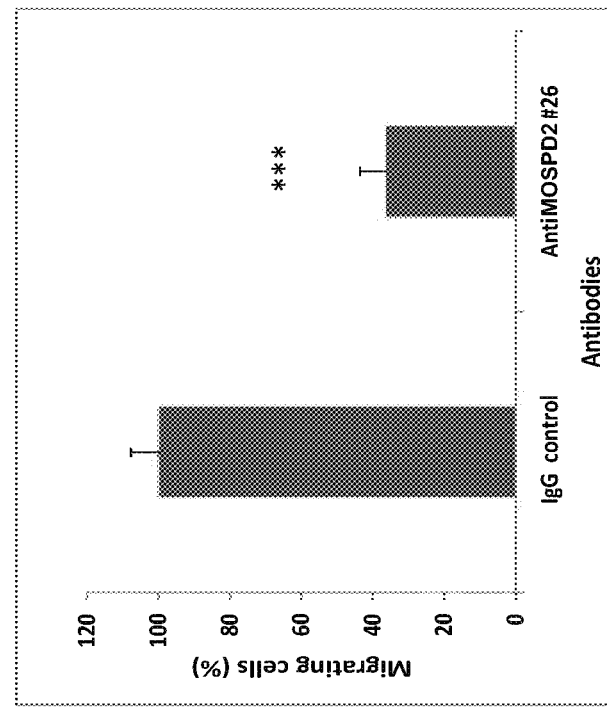
Figure 4W:
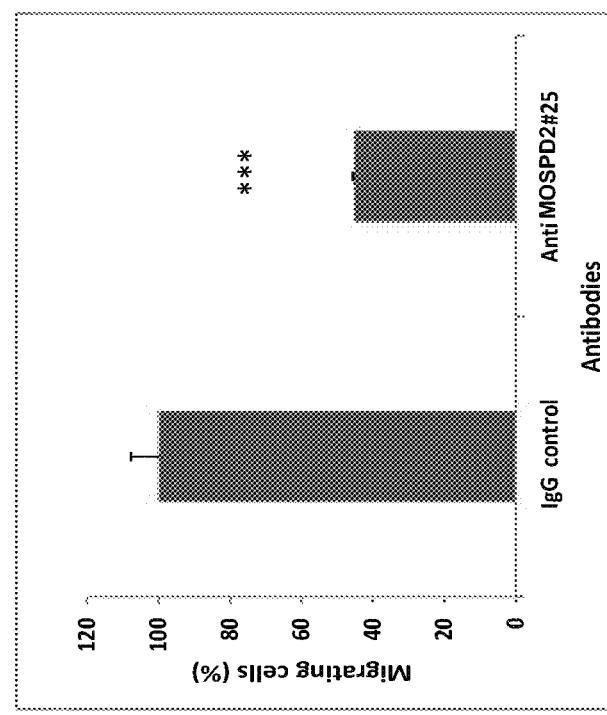
Figure 4B:
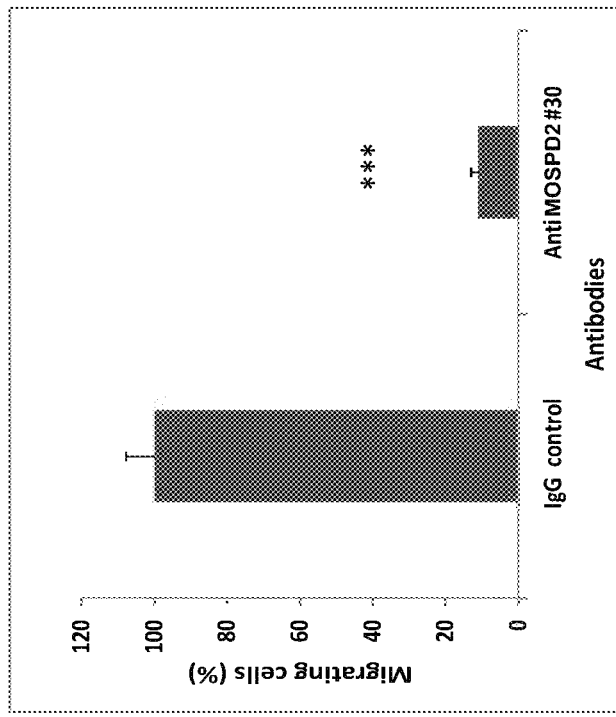
Figure 4A:
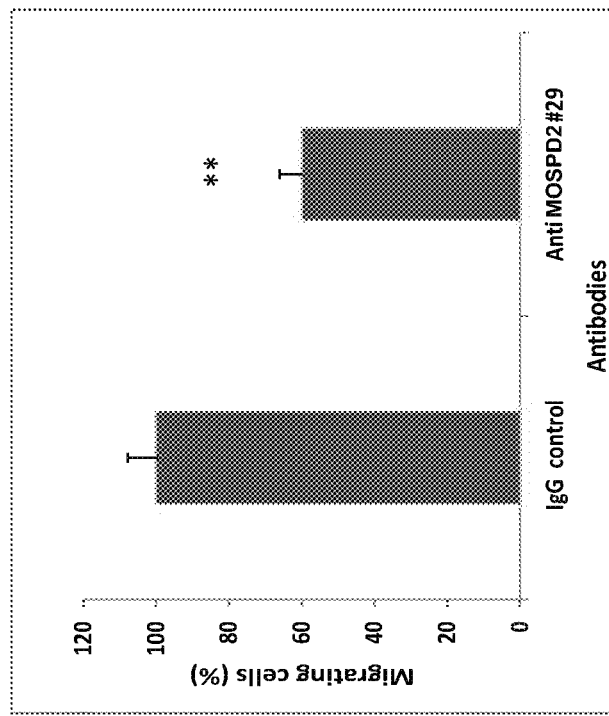

Experiments were conducted to demonstrate the effect on monocyte migration by different anti-MOSPD2 antibodies. Stromal cell-derived factor 1 (SDF-1) and monocyte chemoattractant protein-1 (MCP-1) (100 ng/ml) were placed in the lower chamber of a QCM 24-well migration assay plate. Human primary monocytes ($3 \times 10^5$) were pre-incubated for 30 min with 10 µg/ml of anti-MOSPD2 antibody or with 10 µg/ml of an IgG1 control antibody. Monocytes were then seeded in the upper chamber for 3 h, after which the number of cells that migrated to the lower compartment was determined by FACS. The data in FIGS. 4A-4BB demonstrates that all anti-MOSPD2 antibodies tested significantly inhibited migration of monocytes. The numbering of the antibodies in FIGS. 4A-4BB corresponds to the numbering of antibodies in Table 2.

Example 6

Figure 5:
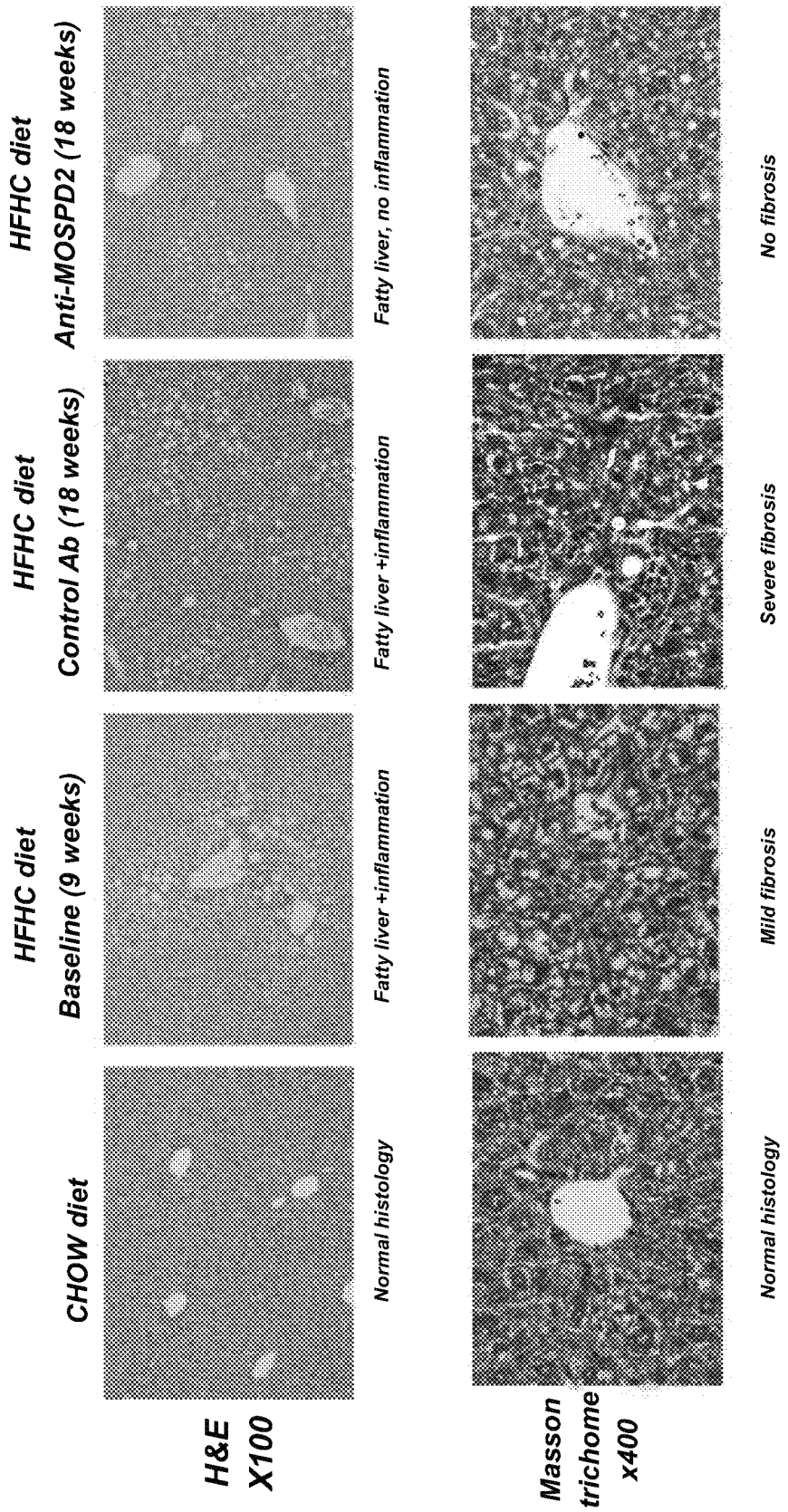
FIG. 5 (FIG. 5) shows liver histology and development of fibrosis following induction of NASH with a HFHC diet and following treatment with control antibody (Control Ab) or anti-MOSPD2 antibodies. Results from two staining protocols, H&E and masson tricome, are shown, and are representative of 10-11 animals tested.

Anti-MOSPD2 Antibodies Reduce Inflammation and Fibrosis in HFHC NASH Mouse Model Mice were fed a high-fat high-carbohydrate (HFHC) diet combined with water enriched with fructose and sucrose for 18 weeks to induce nonalcoholic steatohepatitis (NASH) or a control diet (CHOW diet). From week 10, mice were treated once a week intraperitoneally with 500 µg of anti-MOSPD2 antibody or a control antibody (Control Ab) for 9 weeks. Following treatment, livers were harvested from the mice, and samples were stained with haemotoxylin and eosin (H&E) or masson trichome and the histology was evaluated for presence of fatty liver, inflammation and fibrosis. As shown in FIG. 5, treatment with anti-MOSPD2 antibodies reduced inflammation and fibrosis in NASH.

Example 7

Anti-MOSPD2 Antibodies Reduce Monocyte Accumulation and Fibrosis in HFHC NASH Mouse Model Mice were fed a high-fat high-carbohydrate (HFHC) diet combined with water enriched with fructose and sucrose for 18 weeks to induce nonalcoholic steatohepatitis (NASH) or a control diet (CHOW diet). From week 10, mice were treated once a week intraperitoneally with 500 μg of anti-MOSPD2 antibody or a control antibody (Isotype control) for 9 weeks. Following treatment, livers were harvested from the mice, and immunohistochemical staining was performed on 4 μm sections. Sections were dewaxed and pretreated with epitope-retrieval solution at pH=6 for 10 minutes followed by 30 minutes incubation with anti CD68 antibody (1:400). The Leica Refine-HRP kit was used for detection. Histology evaluation was performed with the Olympus BX60 microscope.

Figure 6A:
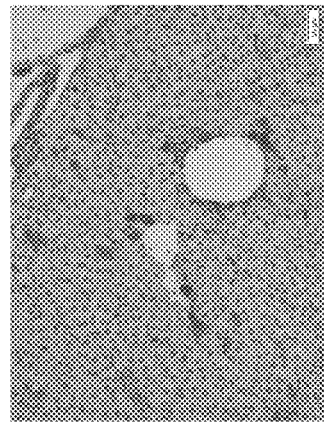
FIGS. 6A-6C (FIGS. 6A-6C) shows staining of CD68+ cells in liver samples of mice fed a control diet (CHOW diet) or an HFHC diet, following treatment with control antibody (Isotype control) or anti-MOSPD2 antibodies.
Figure 6B:
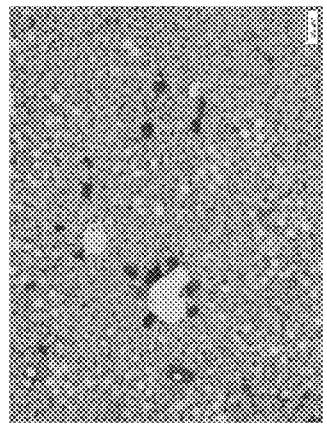
Figure 6C:
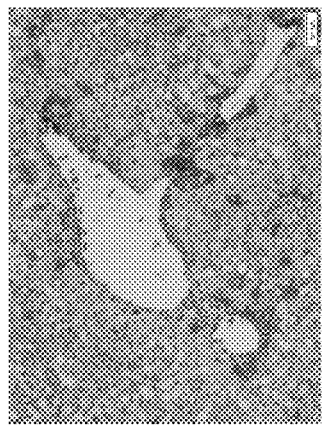
Figure 6D:
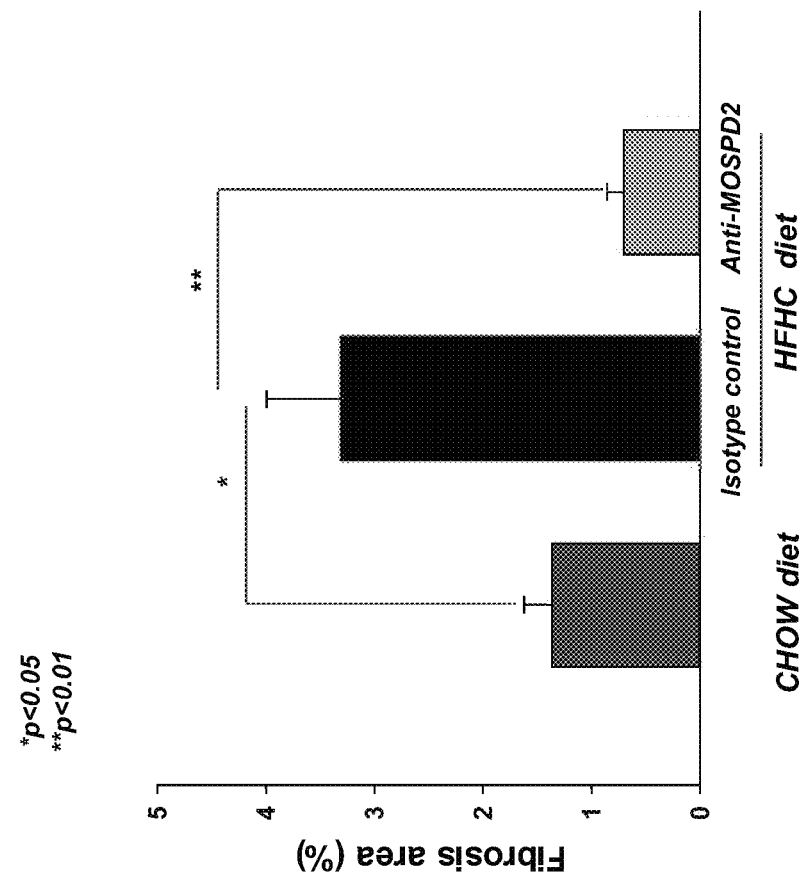
FIG. 6D shows quantification of fibrosis areas of these samples. * p<0.05, ** p<0.01.
Figure 7:
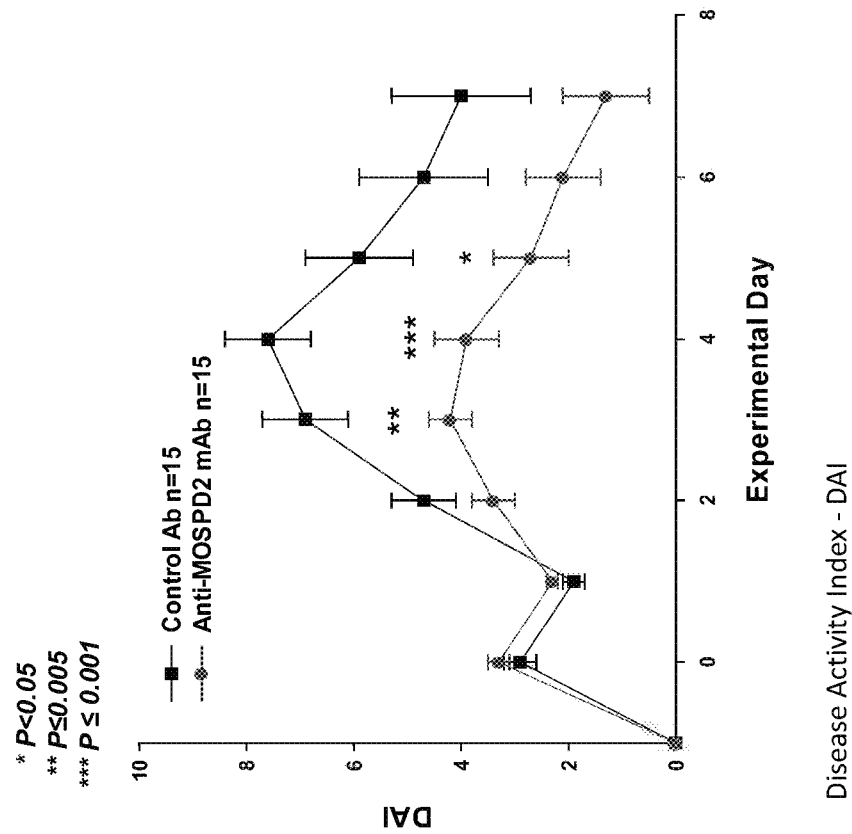
FIG. 7 (FIG. 7) shows the effect of anti-MOSPD2 antibody treatment on disease activity in a trinitrobenzenesulfonic acid (TNBS)-induced Colitis mouse model. *p<0.05,  p≤0.005, * p≤0.001. Results shown are from 15 animals.

Staining results are shown in FIGS. 6A-6C, and the percent fibrosis area is shown in FIG. 6D. FIGS. 6A-6D show anti-MOSPD2 antibodies reduced accumulation of CD68+ cells (i.e., monocytes) and fibrosis.

Example 8

Anti-MOSPD2 Antibody Treatment Significantly Ameliorates Disease Activity in the TNBS-Induced Colitis Mouse Model Colitis was induced in mice using trinitrobenzenesulfonic acid (TNBS). Twenty-four hours after fasting, 100 μl of a solution containing 1.4% TNBS in 50% ethanol was administered into the rectum through a polyurethane catheter with a 21G in diameter inserted 4 cm into the colon (day 0). Then, the anus of the mice was pinched, and the mice were inverted for 3-4 min by grabbing the tail. On days -2, 0 and 3, mice were treated intraperitoneally with 500 μg of anti-MOSPD2 antibody or a control antibody (Isotype control). Disease activity index (DAI) was calculated based on the scoring method shown in Table 4.

Example 9

Anti-MOSPD2 Antibody Treatment Significantly Ameliorates Disease Activity in the TNBS-Induced Colitis Mouse Model Colitis was induced in mice using trinitrobenzenesulfonic acid (TNBS). Twenty-four hours after fasting, 100 μl of a solution containing 1.4% TNBS in 50% ethanol was administered into the rectum through a polyurethane catheter with a 21G in diameter inserted 4 cm into the colon (day 0). Then, the anus of the mice was pinched, and the mice were inverted for 3-4 min by grabbing the tail. On days -2, 0 and 3, mice were treated intraperitoneally with 500 μg of anti-MOSPD2 antibody or a control antibody (Isotype control). Disease activity index (DAI) was calculated based on the scoring method shown in Table 4.

TABLE 4

| | DAI Scoring Method | | |
|---|---|---|---|
| Weight loss (%) | Stool performance | Bloody stool index | Index |
| 0-1 | Normal | None | 0 |
| 1-5.50 | Soft and shaped | None/Fecal occult blood | 1 |
| 5.51-10.50 | Loose | Fecal occult blood | 2 |
| 10.51-15.50 | Loose/Diarrhea | Fecal occult blood/ Defecated hemorrhage | 3 |
| >15.51 | Diarrhea | Defecated hemorrhage | 4 |

At the end of the experiment, 1 cm of colon from the anus and up was washed and place in a 24 well plate with 1 ml medium. Supernatants were collected and tested for cytokines by enzyme-linked immunoassay (ELISA).

As shown in FIGS. 7 and 8A-8C, anti-MOSPD2 antibodies significantly ameliorates colitis disease activity, and reduces the inflammatory mediators, IL-6, MCP-1 and IL-12p40.

Example 10

Anti-MOSPD2 Antibodies Significantly Inhibit Migration of Monocytes from RRMS Patients SDF-1 and MCP-1 (100 ng/ml) were placed in the lower chamber of a QCM 24-well migration assay plate. Human primary monocytes ($3 \times 10^5$) from relapsing remitting multiple sclerosis (RRMS) patients were pre-incubated for 30 min with 10 μg/ml of anti-MOSPD2 monoclonal antibody (mAb) or with 10 μg/ml of an IgG1 control antibody. Monocytes were then seeded in the upper chamber for 3 h, after which the number of cells that migrated to the lower compartment was determined by FACS.

Figure 9:
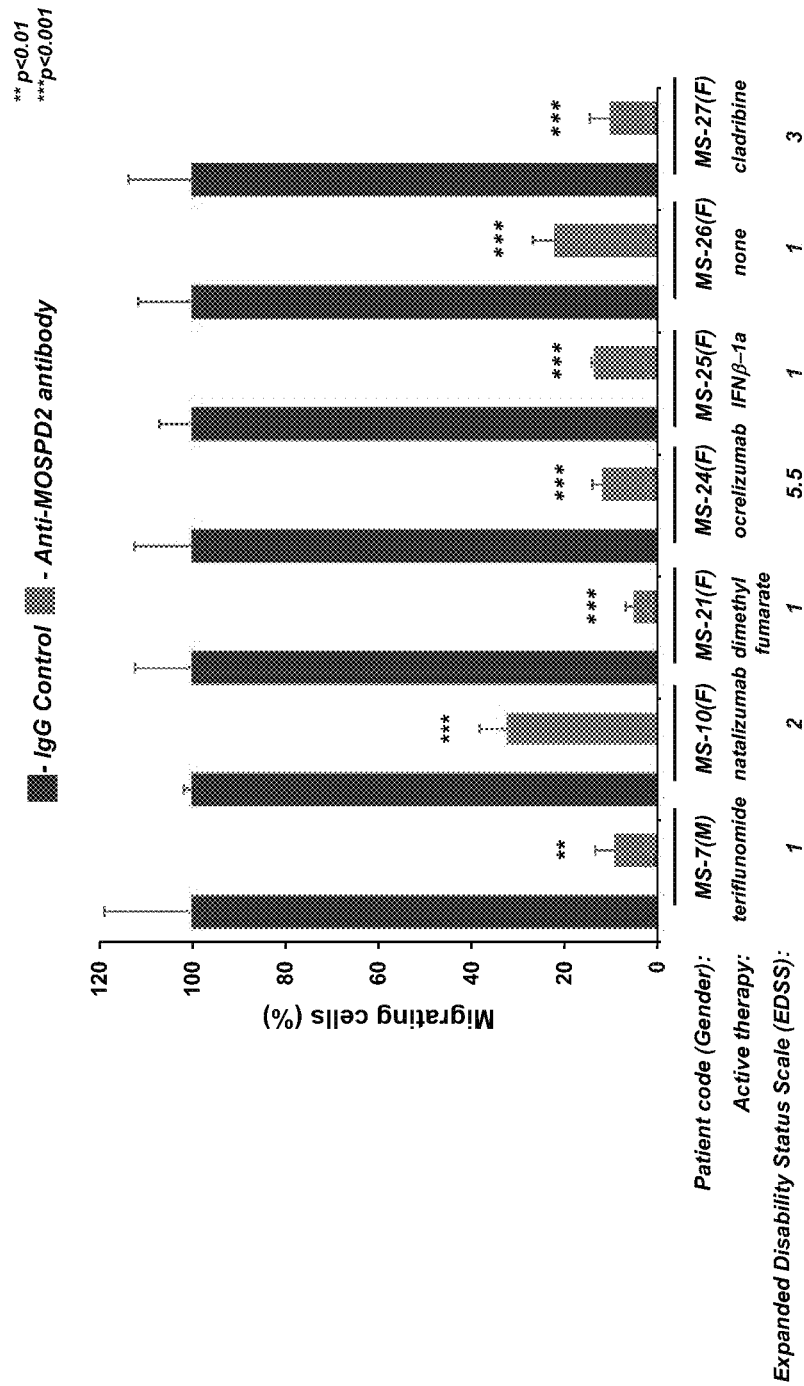
FIG. 9 (FIG. 9) shows that treatment with an anti-MOSPD2 antibody significantly inhibits migration of monocytes from relapsing-remitting multiple sclerosis (RRMS) patients. Results shown are from 7 out of 25 patients with different active therapies and disease severities.  p<0.01, *p<0.001.

As shown in FIG. 9, anti-MOSPD2 antibodies significantly inhibit migration of monocytes from RRMS patients having different active therapies and disease severities.

Example 11

Figure 10:
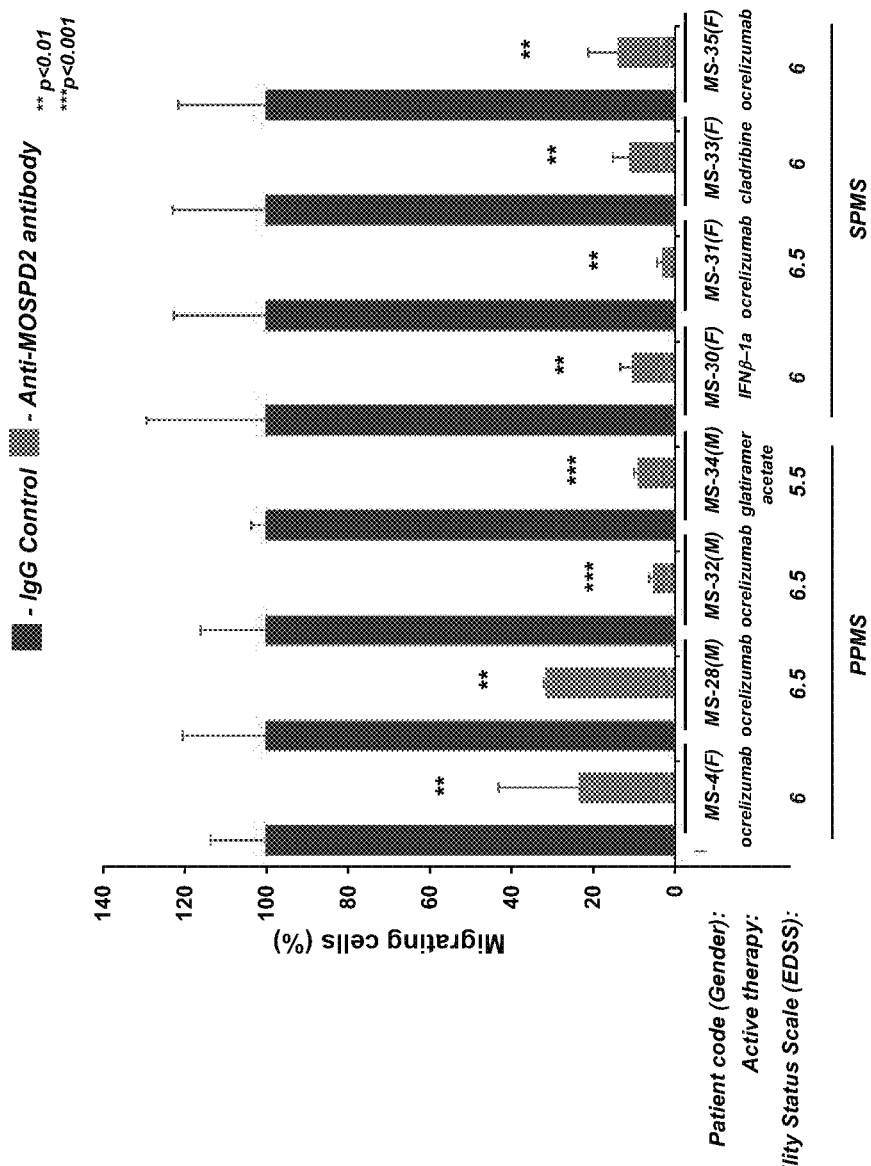
FIG. 10 (FIG. 10) shows that treatment with an anti-MOSPD2 antibody significantly inhibits migration of monocytes from primary progressive multiple sclerosis (PPMS) and secondary progressive multiple sclerosis (SPMS) patients. Results shown are from 7 out of 25 patients with different active therapies and disease severities. * p<0.05,  p<0.01, *p<0.001.

Anti-MOSPD2 Antibodies Significantly Inhibit Migration of Monocytes from PPMS and SPMS Patients SDF-1 and MCP-1 (100 ng/ml) were placed in the lower chamber of a QCM 24-well migration assay plate. Human primary monocytes ($3 \times 10^5$) from primary progressive or secondary progressive multiple sclerosis (PPMS or SPMS, respectively) patients were pre-incubated for 30 min with 10 μg/ml of anti-MOSPD2 mAb or with 10 μg/ml of an IgG1 control antibody. Monocytes were then seeded in the upper chamber for 3 h, after which the number of cells that migrated to the lower compartment was determined by FACS. As shown in FIG. 10, anti-MOSPD2 antibodies significantly inhibit migration of monocytes from PPMS and SPMS patients.

Example 12

Figure 11:
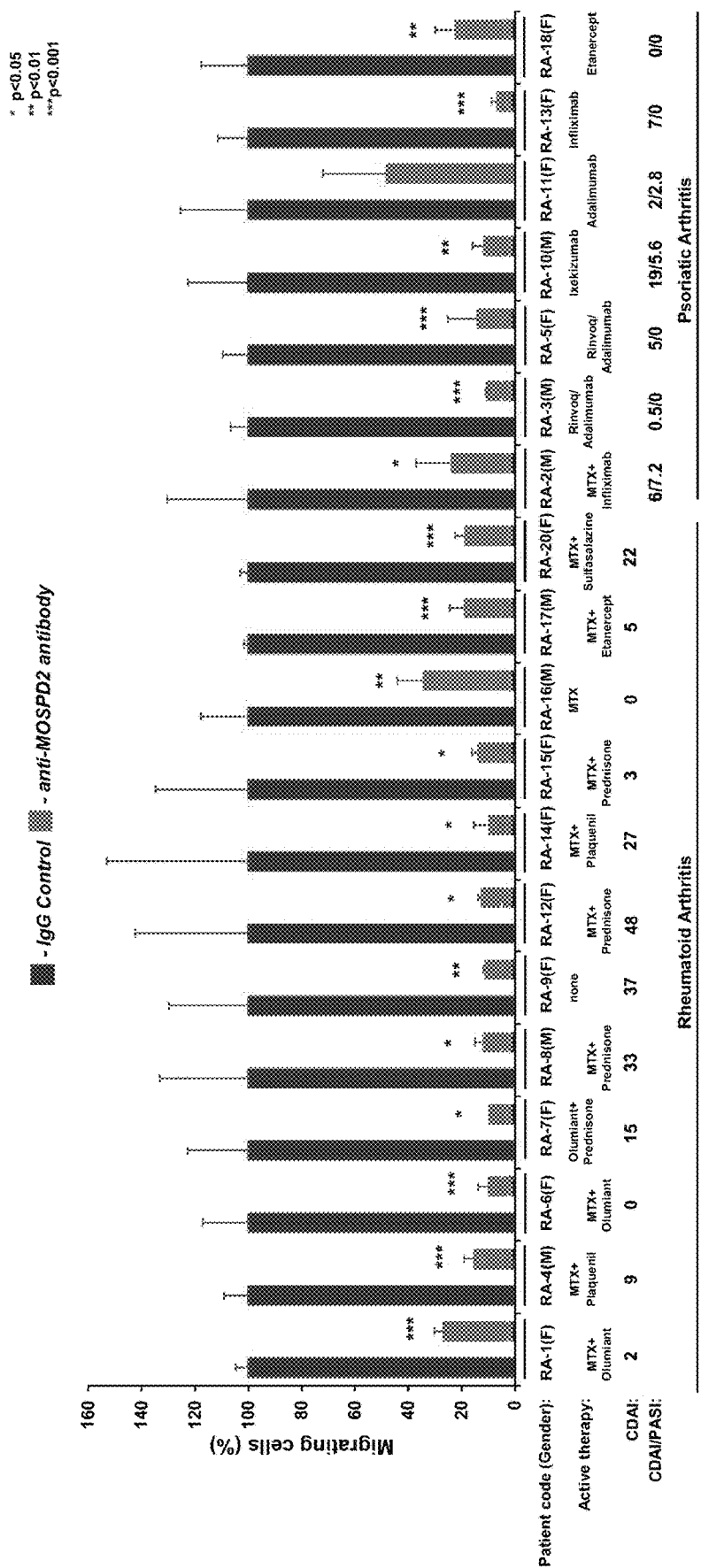
FIG. 11 (FIG. 11) shows that treatment with an anti-MOSPD2 antibody significantly inhibits migration of monocytes from rheumatoid arthritis (RA) and psoriatic arthritis (PsA) patients. * p<0.05,  p<0.01, *p<0.001.

Anti-MOSPD2 Antibodies Significantly Inhibit Migration of Monocytes from RA and PsA Patients SDF-1 and MCP-1 (100 ng/ml) were placed in the lower chamber of a QCM 24-well migration assay plate. Human primary monocytes ($3 \times 10^5$) from rheumatoid arthritis (RA) or psoriatic arthritis (PsA) patients were pre-incubated for 30 min with 10 µg/ml of anti-MOSPD2 mAb or with 10 µg/ml of an IgG1 control antibody. Monocytes were then seeded in the upper chamber for 3 h, after which the number of cells that migrated to the lower compartment was determined by FACS. As shown in FIG. 11 anti-MOSPD2 antibodies significantly inhibit migration of monocytes from RA and psoriatic arthritis PsA patients.

Example 13

Figure 12:
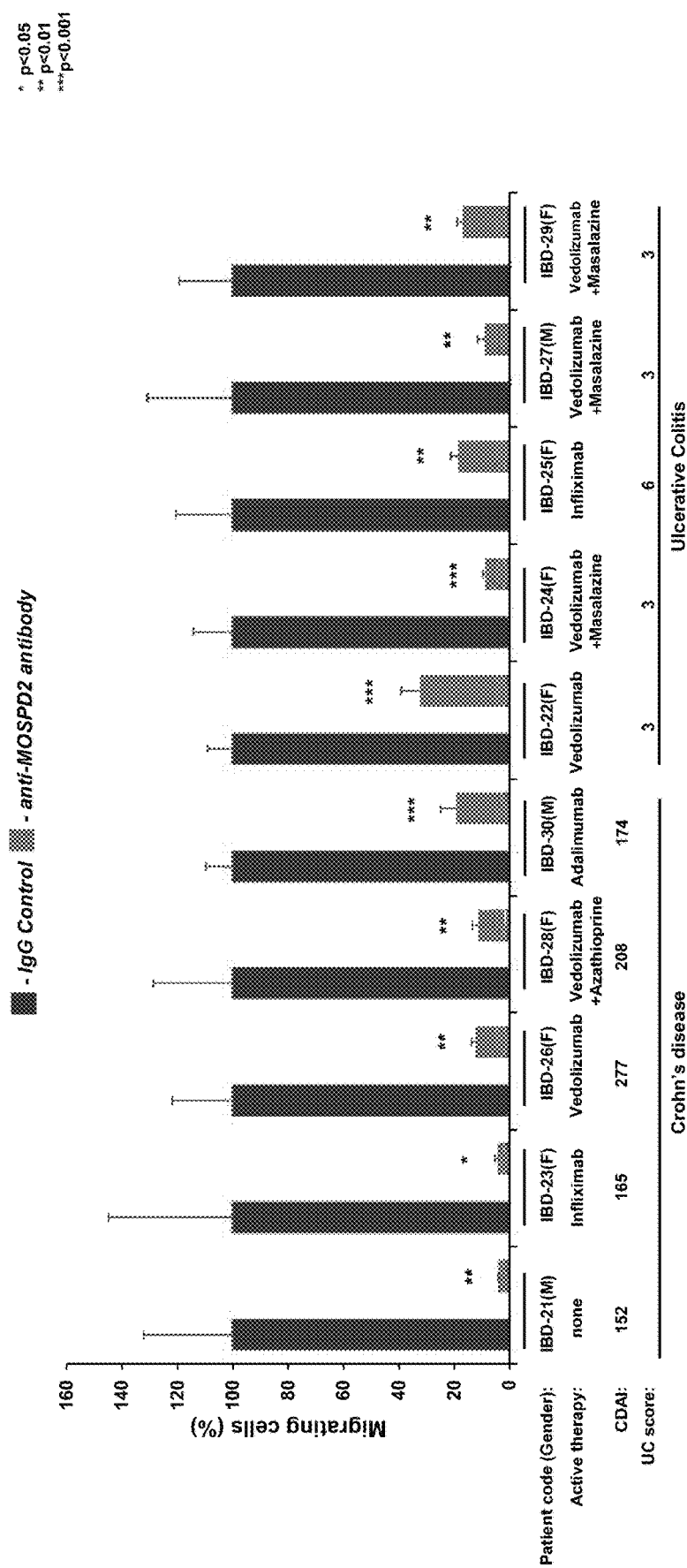
FIG. 12 (FIG. 12) shows that treatment with an anti-MOSPD2 antibody significantly inhibits migration of monocytes from Crohn's disease and ulcerative colitis patients. * p<0.05,  p<0.01, *p<0.001.
Figure 13A:
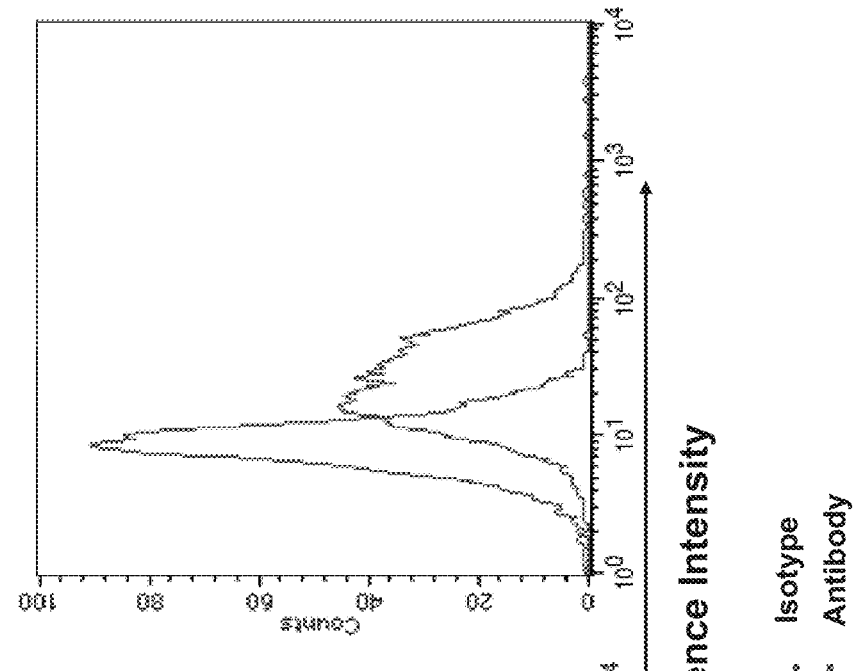
Figure 13B:
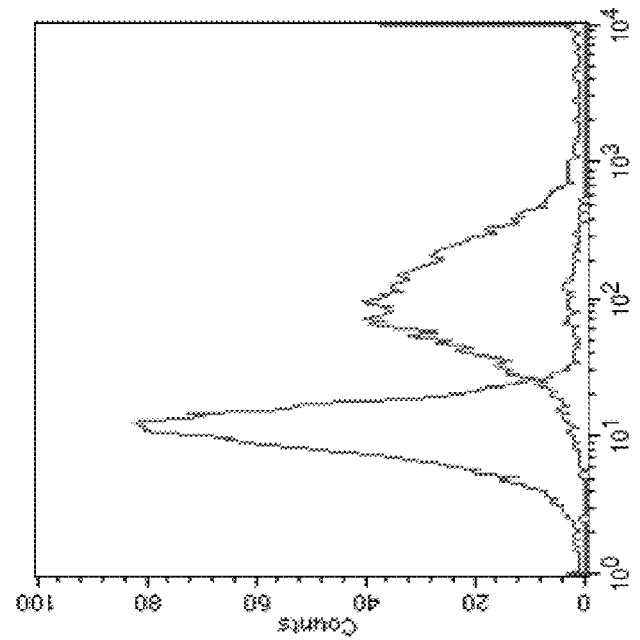

Anti-MOSPD2 Antibodies Significantly Inhibit Migration of Monocytes from Crohn's Disease and Ulcerative Colitis Patients SDF-1 and MCP-1 (100 ng/ml) were placed in the lower chamber of a QCM 24-well migration assay plate. Human primary monocytes ($3\times10^5$) from ulcerative colitis or Crohn's disease patients were pre-incubated for 30 min with 10 µg/ml of anti-MOSPD2 mAb or with 10 µg/ml of an IgG1 control antibody. Monocytes were then seeded in the upper chamber for 3 h, after which the number of cells that migrated to the lower compartment was determined by FACS. As shown in FIG. 12 anti-MOSPD2 antibodies significantly inhibit migration of monocytes from Crohn's disease and ulcerative colitis patients.

Example 14

Binding of Anti-MOSPD2 Antibodies to MOSPD2 on Human Cancer Cell Lines

Studies were performed to evaluate the binding of anti-MOSPD2 antibodies to MOSPD2 expressed on human cancer cells. For that, cervical cancer (Hela), triple negative (TN) breast cancer (MDA-231), melanoma (A2058) and myeloid (U937) cell lines ($1\times10^6$) were stained with an isotype control antibody or humanized anti-MOSPD2 antibody (2 µg) followed by incubation with a secondary APC conjugated anti-human Fcγ antibody (1:200). Analysis was performed by flow cytometry. The results in FIGS. 13A-13D show that anti-MOSPD2 antibodies bind surface expressed MOSPD2 on different cancer cell lines.

The following sequences in Table 5 are part of the present disclosure.

TABLE 5

| SEQ ID NO: | Sequence |
|---|---|
| 1 | SYSMS |
| 2 | TISRGGSYTYYPDSVKG |
| 3 | TISRSSSYIYYADSVKG |
| 4 | TISRGGSNKYYADSVKG |
| 5 | TISRSGGSTSYAQKVQG |
| 6 | TISRGGSNKYYAESVKG |
| 7 | TISRGGSYTYYPESVKG |
| 8 | TISRGGSYTYYPDTVKG |
| 9 | GK |
| 10 | KSSQSLLDSDGKTNLN |
| 11 | KSSQSLVDSDAKTNLN |
| 12 | RSSQSLVDSDAKTNLN |
| 13 | KSSQSLLESEGKTNLN |
| 14 | KSSQSLVESEGKTNLN |
| 15 | KSSQSLLESDGKTNLN |
| 16 | KSSQSLLDTDGKTNLN |
| 17 | KSSQSLLDSEGKTNLN |
| 18 | KSSQSLLDSDAKTNLN |
| 19 | LVSKLDS |
| 20 | LVSKRDS |
| 21 | LVSNRDS |
| 22 | LVSKLES |
| 23 | LVSKRES |

TABLE 5-continued

Sequences

| SEQ ID NO: | Sequence |
| --- | --- |
| 24 | LVSKLDT |
| 25 | WQGTHFPRT |
| 26 | *Homo sapiens* motile sperm domain containing 2 (MOSPD2), protein variant 1<br>Met Ala Glu Asn His Ala Gln Asn Lys Ala Lys Leu Ile Ser<br>Glu Thr Arg Arg Arg Phe Glu Ala Glu Tyr Val Thr Asp<br>Lys Ser Asp Lys Tyr Asp Ala Arg Asp Val Glu Arg Leu<br>Gln Gln Asp Asp Asn Trp Val Glu Ser Tyr Leu Ser Trp<br>Arg His Asn Ile Val Asp Glu Thr Leu Lys Met Leu Asp<br>Glu Ser Phe Gln Trp Arg Lys Glu Ile Ser Val Asn Asp Leu<br>Asn Glu Ser Ser Ile Pro Arg Trp Leu Leu Glu Ile Gly Val<br>Ile Tyr Leu His Gly Tyr Asp Lys Glu Gly Asn Lys Leu Phe<br>Trp Ile Arg Val Lys Tyr His Val Lys Asp Gln Lys Thr Ile<br>Leu Asp Lys Lys Lys Leu Ile Ala Phe Trp Leu Glu Arg<br>Tyr Ala Lys Arg Glu Asn Gly Lys Pro Val Thr Val Met<br>Phe Asp Leu Ser Glu Thr Gly Ile Asn Ser Ile Asp Met Asp<br>Phe Val Arg Phe Ile Ile Asn Cys Phe Lys Val Tyr Tyr Pro<br>Lys Tyr Leu Ser Lys Ile Val Ile Phe Asp Met Pro Trp Leu<br>Met Asn Ala Ala Phe Lys Ile Val Lys Thr Trp Leu Gly Pro<br>Glu Ala Val Ser Leu Leu Lys Phe Thr Ser Lys Asn Glu Val<br>Gln Asp Tyr Val Ser Val Glu Tyr Leu Pro Pro His Met Gly<br>Gly Thr Asp Pro Phe Lys Tyr Ser Tyr Pro Pro Leu Val Asp<br>Asp Asp Phe Gln Thr Pro Leu Cys Glu Asn Gly Pro Ile Thr<br>Ser Glu Asp Glu Thr Ser Ser Lys Glu Asp Ile Glu Ser Asp<br>Gly Lys Glu Thr Leu Glu Thr Ile Ser Asn Glu Glu Gln Thr<br>Pro Leu Leu Lys Lys Ile Asn Pro Thr Glu Ser Thr Ser Lys<br>Ala Glu Glu Asn Glu Lys Val Asp Ser Lys Val Lys Ala<br>Phe Lys Lys Pro Leu Ser Val Phe Lys Gly Pro Leu Leu His<br>Ile Ser Pro Ala Glu Glu Leu Tyr Phe Gly Ser Thr Glu Ser<br>Gly Glu Lys Lys Thr Leu Ile Val Leu Thr Asn Val Thr Lys<br>Asn Ile Val Ala Phe Lys Val Arg Thr Thr Ala Pro Glu Lys<br>Tyr Arg Val Lys Pro Ser Asn Ser Ser Cys Asp Pro Gly Ala<br>Ser Val Asp Ile Val Val Ser Pro His Gly Gly Leu Thr Val<br>Ser Ala Gln Asp Arg Phe Leu Ile Met Ala Ala Glu Met Glu<br>Gln Ser Ser Gly Thr Gly Pro Ala Glu Leu Thr Gln Phe Trp<br>Lys Glu Val Pro Arg Asn Lys Val Met Glu His Arg Leu<br>Arg Cys His Thr Val Glu Ser Ser Lys Pro Asn Thr Leu Thr<br>Leu Lys Asp Asn Ala Phe Asn Met Ser Asp Lys Thr Ser<br>Glu Asp Ile Cys Leu Gln Leu Ser Arg Leu Leu Glu Ser<br>Asn Arg Lys Leu Glu Asp Gln Val Gln Arg Cys Ile Trp<br>Phe Gln Gln Leu Leu Leu Ser Leu Thr Met Leu Leu Leu<br>Ala Phe Val Thr Ser Phe Phe Tyr Leu Leu Tyr Ser |
| 27 | *Homo sapiens* motile sperm domain containing 2 (MOSPD2), protein variant 2<br>MLDESFQWRKEISVNDLNESSIPRWLLEIGVIY<br>LHGYDKEGNKLFWIRVKYHVKDQKTILDKKK<br>LIAFWLERYAKRENGKPVTVMFDLSETGINSID<br>MDFVRFIINCFKVYYPKYLSKIVIFDMPWLMNA<br>AFKIVKTWLGPEAVSLLKFTSKNEVQDYVSVEY<br>LPPHMGGTDPFKYSYPPLVDDDFQTPLCENGPIT<br>SEDETSSKEDIESDGKETLETISNEEQTPLLKKINP<br>TESTSKAEENEKVDSKVKAFKKPLSVFKGPLLHI<br>SPAEELYFGSTESGEKKTLIVLTNVTKNIVAFKVR<br>TTAPEKYRVKPSNSSCDPGASVDIVVSPHGGLT<br>VSAQDRFLIMAAEMEQSSGTGPAELTQFWKEVP<br>RNKVMEHRLRCHTVESSKPNTLTLKDNAFNMSD<br>KTSEDICLQLSRLLESNRKLEDQVQRCIWFQQLLL<br>SLTMLLLAFVTSFFYLLYS |
| 28 | *Homo sapiens* motile sperm domain containing 2 (MOSPD2), protein variant 3<br>MAENHAQNKAKLISETRRRFEAEYVTDKSDKY<br>DARDVERLQQDDNWVESYLSWRHNIVDETLK<br>MLDESFQWRKEISVNDLNESSIPRWLLEIGVIYL<br>HGYDKEGNKLFWIRVKYHVKDQKTILDKKKLI<br>AFWLERYAKRENGKPVTVMFDLSETGINSIDMD<br>FVRFIINCFKVYYPKYLSKIVIFDMPWLMNAAFK<br>IVKTWLGPEAVSLLKFTSKNEVQDYVSVEYLPP<br>HMGGTDPFKYSYPPLVDDDFQTPLCENGPITSE<br>DETSSKEDIESDGKETLETISNEEQTPLLKKINPT<br>ESTSKAEENEKVDSKVKAFKKPLSVFKGPLLHIS<br>PAEELYFGSTESGEKKTLIVLTNVTKNIVAFKVR |

TABLE 5-continued

Sequences

| SEQ ID NO: | Sequence |
|---|---|
| | TTAPEKYRVKPSNSSCDPGASVDIVVSPHGGLTV
SAQDRFLIMAAEMEQSSGTGPAELTQFWKEVPR
NKVMEHRLRCHTVESSKPNTLTLKDNAFNMSDK
TSEDICLQFATSSCEMDCSPP |
| 29 | *Homo sapiens* motile sperm domain containing 2 (MOSPD2), protein variant X2
MAENHAQNKAKLISETRRRFEAEYVTDKSDKY
DARDVERLQQDDNWVESYLSWRHNIVDETLK
MLDESFQWRKEISVNDLNESSIPRWLLEIGVIYL
HGYDKEGNKLFWIRVKYHVKDQKTILDKKKLI
AFWLERYAKRENGKPVTVMFDLSETGINSIDMD
FVRFIINCFKVYYPKYLSKIVIFDMPWLMNAAFK
IVKTWLGPEAVSLLKFTSKNEVQDYVSVEYLPP
HMGGTDPFKYSYPPLVDDDFQTPLCENGPITSED
ETSSKEDIESDGKETLETISNEEQTPLLKKINPTES
TSKAEENEKVDSKVKAFKKPLSVFKGPLLHISPA
EELYFGSTESGEKKTLIVLTNVTKNIVAFKVRTT
APEKYRVKPSNSSCDPGASVDIVVSPHGGLTVSA
QDRFLIMAAEMEQSSGTGPAELTQFWKEVPRNK
VMEHRLRCHTVESSKPNTLTLKDNAFNMSDKTS
EDICLQYS |
| 30 | *Homo sapiens* motile sperm domain containing 2 (MOSPD2), transcript variant 1, mRNA Coding region 125-1678 |

```
   1 accgcctccc cctcccaccc ttctctgtct acctctgggc ggactgccg ggtgatgaga
  61 tactcggtcg gcgacggtag aacgggcgac ggcgacaacc gcaatcacat ccacgacggt
 121 gatcatggca gagaatcacg cccagaataa agccaagctc atctctgaga cccggaggag
 181 gttcgaagct gagtatgtga cagataagtc agataaatat gatgcacgtg atgttgaaag
 241 gctacaacaa gatgataact gggtgaaag ttacttatct tggagacata atattgtaga
 301 tgaaacactg aagatgctcg atgagagttt tcagtggagg aaagaaattt ctgtcaatga
 361 ccttaatgaa tcctccattc ccagatggtt attggaaatt ggtgttattt atctccatgg
 421 ttatgacaaa gaaggtaaca aattgttctg gatcagggtg aagtatcatg taaaagacca
 481 gaaaaccata ttggacaaaa agaagctcat agcattctgt ttggaacgtt atgctaagag
 541 ggaaaatggg aaacctgtaa cagtgatgtt tgacctgtca gaaactggaa taaatagcat
 601 tgacatggac tttgtacgct ttatcatcaa ctgctttaag gtttattacc ctaaatacct
 661 ctcaaaaata gtgatctttg atatgccttg gttaatgaat gctgctttca aaattgtgaa
 721 aacctggctt ggtccagaag cagtgagctt gttgaagttt acaagcaaaa atgaagtcca
 781 ggactatgtc agtgtagaat acctgcctcc ccacatgggt ggaactgatc cttttcaagta
 841 tagctatcca ccactagtag atgatgactt ccagaccccca ctgtgtgaga atgggcctat
 901 taccagtgag gatgaaactt caagtaaaga agacatagaa agtgatggca agaaaacatt
 961 ggaaacaatt tctaatgaag aacaaacacc tcttcttaaa aagattaacc caaccgaatc
1021 tacttccaaa gcagaagaaa atgaaaaagt tgattcaaaa gtgaagctt tcaagaaacc
1081 attgagtgta tttaaaggcc ccttactaca catcagccca gcagaagaac tgtactttgg
1141 aagtacagaa tccggagaga agaaaacctt aatagtgttg acaaatgtaa ctaaaaatat
1201 agtggcattt aaggtgagaa caacagctcc agaaaaatac agagtcaagc caagcaatag
1261 cagctgtgac ccgggtgcat cagtggatat agttgtgtct ccccatgggg gtttaacagt
1321 ctctgcccaa gaccgttttc tgataatggc tgcagaaatg gaacagtcat ctggcacagg
1381 cccagcagaa ttaactcagt tttggaaaga agttcccaga aacaaagtga tggaacatag
1441 gttaagatgc catactgttg aaagcagtaa accaaacact cttacgttaa aagacaatgc
1501 tttcaatatg tcagataaaa ccagtgaaga tatatgtcta caactcagtc gtttactaga
1561 aagcaatagg aagcttgaag accaagttca gcgttgtatc tggttccagc agctgctgct
1621 ttccttaaca atgctcttgc ttgcttttgt cacctctttc ttctatttat tgtacagtta
1681 aagaagtggt gccgggtagg aaccacggtt ccttcgtcca ttagttggaa aaagtaacag
1741 acctaaaact ctaccaagct actaaaaaca ttgcacatct gtgcttccta aaaggaaata
1801 tgcagcacgt ggaggggaac acatacatgt cttgaaaata aactgctaga ataaagaaat
1861 gctggagaaa ttgattataa gagactatag ctatttagta aagtaagtaa aggcatatcc
1921 attgtgtaaa ttaatagttt aaatataatt tatttttttcc ttttgatctg aatacttta
1981 aagcttaagt tttatcgtgt aaatacatta gctaaactga aagtataag taacatgctt
2041 tgttgcagcc aaaaaatgta atctgctttt ttatgacaga attattatag ctgagctgac
2101 ttactagctt ttctatacta tgtatataga agaacatgta tattgagaaa gaaaacatac
2161 ttatatagag gaatttatgt aaccatgact tgtaatttt gagaattcct cccagtgatg
2221 gtcagtattc ttttggaatg taaaccgatt taatgccaaa ccacctaac cttttgtttct
2281 cagtgttcct taacagcctg cctttttatta atctcaggct ttttatgaa cactctcatt
2341 tcagtagaat ttggaaaact aagcgtggtt ggaatttctt tgaattctgt tagtaatgcc
2401 caaaagaaaa gtctcaagca gtcccccctat ccagtcattt ttatggagtt tcatgttgtc
2461 cactatagct ggacactgaa ccttttgcct aatttattat aaaggcctga ccctctattg
2521 tcccatcttc accccccattc cagagcagag gagtctctgt ggaccatgaa ttgcactgtc
2581 tccctcctca tttctaaatg aaaggtatta gatataaatt tttttgaaag gttagttgtt
2641 tgagatgcta agcaggataa taaatttaga ttttaaaatg ttccctgtaa aagtcagccc
2701 atgacaagga aatttacaaa atactagagt atctagaagg gtgaaaacaa aaaaaaataa
2761 aaagaaacac agacgcccag gtgtcagctc tccgtttaaa gaatgaaaaa tgtaactcat
2821 gatgatctgt gaaaccttca aactaggacc aattgactta cttgatattc tgcctttgat
2881 atggtagtac ccaccccggta ttcctaaatt cctaaaagga tacaccttgc agtagcagag
2941 gcaatgacat gagtttgttt tctcattaat atgaccagtt ggggtctatg ttggttcaca
3001 tgtacatcta ctttatatga aagaaaaaac agttgtctgc ctgtaaaatg ttgagtttcg
```

TABLE 5-continued

Sequences

| SEQ ID NO: | Sequence |
|---|---|

```
          3061  attgagccat gtttggagat tttattacta ttctgaaggg tagtgttgtt ggttttcatc
          3121  ttcaagaagt tgattccaaa actgagttat gaagaatgat ataacagttc cttcaaaatt
          3181  ggcctaggaa ataaaacctt aaaaggacaa aaaaaaaaa
```

31         Homo sapiens motile sperm domain containing 2
           (MOSPD2), transcript variant 2, mRNA Coding region 278-1642

```
             1  agtcacaata ataggtactt aaaaacatgt catatgatag gaaactagaa taacacacct
            61  ctaaataatc catggattac caacttctca gcaatggtgt aaattcttct gctaaataac
           121  ccgtgggtta aagaggacat cacattggaa attccagagt acttaaaata agtcagataa
           181  atatgatgca cgtgatgttg aaaggctaca acaagatgat aactgggttg aaagttactt
           241  atcttggaga cataatattg tagatgaaac actgaagatg ctcgatgaga gttttcagtg
           301  gaggaaagaa atttctgtca atgacccttaa tgaatcctcc attcccagat ggttattgga
           361  aattggtgtt atttatctcc atggttatga caaagaaggt aacaaattgt tctggatcag
           421  ggtgaagtat catgtaaaag accagaaaac catattggac aaaaagaagc tcatagcatt
           481  ctggttggaa cgttatgcta agagggaaaa tgggaaacct gtaacagtga tgtttgacct
           541  gtcagaaact ggaataaata gcattgacat ggactttgta cgctttatca tcaactgctt
           601  taaggtttat taccctaaat acctctcaaa aatagtgatc tttgatatgc cttggttaat
           661  gaatgctgct ttcaaaattg tgaaaacctg gcttggtcca gaagcagtga gcttgttgaa
           721  gtttacaagc aaaaatgaag tccaggacta tgtcagtgta gaatacctgc ctccccacat
           781  gggtggaact gatcctttca agtatagcta tccaccacta gtagatgatg acttccagac
           841  cccactgtgt gagaatgggc ctattaccag tgaggatgaa acttcaagta aagaagacat
           901  agaaagtgat ggcaaagaaa cattggaaac aatttctaat gaagaacaaa cacctcttct
           961  taaaaagatt aacccaaccg aatctacttc caaagcagaa gaaaatgaaa aagttgattc
          1021  aaaagtgaaa gctttcaaga aaccattgag tgtatttaaa ggcccctac tacacatcag
          1081  cccagcagaa gaactgtact tggaagtac agaatccgga gagaagaaaa ccttaatagt
          1141  gttgacaaat gtaactaaaa atatagtggc atttaaggtg agaacaacag ctccagaaaa
          1201  atacagagtc aagccaagca atagcagctg tgacccgggt gcatcagtgg atatagttgt
          1261  gtctccccat gggggtttaa cagtctctgc ccaagaccgt tttctgataa tggctgcaga
          1321  aatggaacag tcatctggca caggcccagc agaattaact cagttttgga aagaagttcc
          1381  cagaaacaaa gtgatggaac ataggttaag atgccatact gttgaaagca gtaaaccaaa
          1441  cactcttacg ttaaaagaca atgctttcaa tatgtcagat aaaaccagtg aagatatatg
          1501  tctacaactc agtcgtttac tagaaagcaa taggaagctt gaagaccaag ttcagcgttg
          1561  tatctggttc cagcagctgc tgcttttcctt aacaatgctc ttgcttgctt ttgtcacctc
          1621  tttcttctat ttattgtaca gttaaagaag tggtgccggg taggaaccac ggttccttcg
          1681  tccattagtt ggaaaaagta acagacctaa aactctacca agctactaaa aacattgcac
          1741  atctgtgctt cctaaaagga aatatgcagc acgtggaggg gaacacatac atgtcttgaa
          1801  aataaactgc tagaataaag aaatgctgga gaaattgatt ataagagact atagctattt
          1861  agtaaagtaa gtaaaggcat atccattgtg taaattaata gtttaaatat aatttatttt
          1921  ttccttttga tctgaatact tttaaagctt aagttttatc gtgtaaatac attagctaaa
          1981  ctgaaaagta taagtaacat gctttgttgc agccaaaaaa tgtaatctgc tttttttatga
          2041  cagaattatt atagctgagc tgacttacta gcttttctat actatgtata tagaagaaca
          2101  tgtatattga gaaagaaaac atacttatat agaggaattt gttaaccat gactttgtaa
          2161  ttttgagaat tcctcccagt gatggtcagt attctttttgg aatgtaaacc gatttaatgc
          2221  caaaccacct taacctttgt ttctcagtgt tccttaacag cctgcctttt attaatctca
          2281  ggctttttta tgaacactct catttcagta gaatttggaa aactaagcgt ggttggaatt
          2341  tctttgaatt ctgttagtaa tgcccaaaag aaaagtctca agcagtcccc ctatccagtc
          2401  atttttatgg agtttcatgt tgtccactat agctggacac tgaacctttt gcctaattta
          2461  ttataaaggc ctgaccctct attgtcccat cttcaccccc attccagagc agaggagtct
          2521  ctgtggacca tgaattgcac tgtctccctc ctcatttcta aatgaaaggt attagatata
          2581  aatttttttg aaaggttagt tgtttgagat gctaagcagg ataataaatt tagattttaa
          2641  aatgttccct gtaaaagtca gcccatgaca aggaaattta caaaatacta gagtatctag
          2701  aagggtgaaa acaaaaaaaa ataaaaagaa acacagacgc ccaggtgtca gctctccgtt
          2761  taaagaatga aaaatgtaac tcatgatgat ctgtgaaacc ttcaaactag gaccaattga
          2821  cttacttgat attctgcctt tgatatggta gtacccaccc ggtattccta aaatcctaaa
          2881  aagatacacc ttgcagtagc agaggcaatg acatgagttt gttttctcat taatatgacc
          2941  agtttgggtc tatgttggtt cacatgtaca tctactttat atgaaagaaa aaacagttgt
          3001  ctgcctgtaa aatgttgagt ttcgattgag ccatgtttgg agattttatt actattctga
          3061  agggtagtgt tgttggtttt catcttcaag aagttgattc caaaactgag ttatgaagaa
          3121  tgatataaca gttccttcaa aattggccta ggaaataaaa ccttaaaagg acaaaaaaaa
          3181  aaa
```

32         Homo sapiens motile sperm domain containing 2
           (MOSPD2), transcript variant 3, mRNA Coding region 125-1582

```
             1  accgcctccc cctcccaccc ttctctgtct acctctgggc gggactgccg ggtgatgaga
            61  tactcggtcg gcgacggtag aacgggcgac ggcgacaacc gcaatcacat ccacgacggt
           121  gatcatggca gagaatcacg cccagaataa agccaagctc atctctgaga cccggaggag
           181  gttcgaagct gagtatgtga cagataagtc agataaatat gatgcacgtg atgttgaaag
           241  gctacaacaa gatgataact gggttgaaag ttacttatct tggagacata atattgtaga
           301  tgaaacactg aagatgctcg atgagagttt cagtggagg aaagaaattt ctgtcaatga
           361  ccttaatgaa tcctccattc cagatggtt attggaaatt ggtgttattt atctccatgg
           421  ttatgacaaa gaaggtaaca aattgttctg gatcagggtg aagtatcatg taaaagacca
           481  gaaaaccata ttggacaaaa agaagctcat agcattctgg ttggaacgtt atgctaagag
           541  ggaaaatggg aaacctgtaa cagtgatgtt tgacctgtca gaaactggaa taaatagcat
           601  tgacatggac tttgtacgct ttatcatcaa ctgctttaag gtttattacc ctaaatacct
           661  ctcaaaaata gtgatctttg atatgccttg gttaatgaat gctgctttca aaattgtgaa
           721  aacctggctt ggtccagaag cagtgagctt gttgaagttt acaagcaaaa atgaagtcca
```

TABLE 5-continued

Sequences

| SEQ ID NO: | Sequence | |
|---|---|---|
| | 781 | ggactatgtc agtgtagaat acctgcctcc ccacatgggt ggaactgatc ctttcaagta |
| | 841 | tagctatcca ccactagtag atgatgactt ccagacccca ctgtgtgaga atgggcctat |
| | 901 | taccagtgag gatgaaactt caagtaaaga agacatagaa agtgatggca aagaaacatt |
| | 961 | ggaaacaatt tctaatgaag aacaaacacc tcttcttaaa aagattaacc caaccgaatc |
| | 1021 | tacttccaaa gcagaagaaa atgaaaaagt tgattcaaaa gtgaaagctt tcaagaaacc |
| | 1081 | attgagtgta tttaaaggcc ccttactaca catcagccca gcagaagaac tgtactttgg |
| | 1141 | aagtacagaa tccggagaga agaaaacctt aatagtgttg acaaatgtaa ctaaaaatat |
| | 1201 | agtggcattt aaggtgagaa caacagctcc agaaaaatac agagtcaagc caagcaatag |
| | 1261 | cagctgtgac ccgggtgcat cagtggatat agttgtgtct ccccatgggg gtttaacagt |
| | 1321 | ctctgcccaa gaccgttttc tgataatggc tgcagaaatg gaacagtcat ctggcacagg |
| | 1381 | cccagcagaa ttaactcagt tttggaaaga agttcccaga aacaaagtga tggaacatag |
| | 1441 | gttaagatgc catactgttg aaagcagtaa accaaacact cttacgttaa aagacaatgc |
| | 1501 | tttcaatatg tcagataaaa ccagtgaaga tatatgtcta caatttgcca cctccagctg |
| | 1561 | tgaaatggac tgcagtccac cctaagtact gtgcacagta tctccctgtg tgtgtgcaca |
| | 1621 | gtggcttccc cttacatggt agattttttgg ccttaatata atctaatccc aaagtagttg |
| | 1681 | tgtatgtttt ctgttccttg gcaaataaat gaagaaataa ttagccaaga ttgaaaatgt |
| | 1741 | attgtcctaa cggtgtccct ttaatgtttc atatgaaaaa ttatgttgac ccactaaaat |
| | 1801 | atccttgctc aatgtctggt cagttgaatt taataacata tcttgttaat gtttgtgtgt |
| | 1861 | ctattaaatg tgactaagca ggattactga aaattcacta taaaatcaaa ggcatctaaa |
| | 1921 | cgtttgtact tgtcttgatt aatcatatat ttacacttga ttttttttctg tcttcatttg |
| | 1981 | tttttattta atcataattg catgattttt ttggtactct aatcagtaat tttattttta |
| | 2041 | atcatgtcat tacctattca tgaccaaatt accaaggaac caacatttag atttagatat |
| | 2101 | ttgttttcac ttaggaatgg aaattaatag attttccatg aaagcattag tgaaatatca |
| | 2161 | ttaccttgat ctgcaagtag cctaaaaatg cgattgctgg taaacctggc ctcaaatttc |
| | 2221 | atactaccat aactgttttt atatattgcc actaattttg actggattta atagcactttt |
| | 2281 | attgtacaac tacaaaaaaa aatatatttcc tagaattgtt gccagtgtaa |
| 33 | Homo sapiens motile sperm domain containing 2 (MOSPD2), transcript variant X2, mRNA Coding region 125-1549 | |
| | 1 | accgcctccc cctcccaccc ttctctgtct acctctgggc gggactgccg ggtgatgaga |
| | 61 | tactcggtcg gcgacggtag aacgggcgac ggcgacaacc gcaatcacat ccacgacggt |
| | 121 | gatcatggca gagaatcacg cccagaataa agccaagctc atctctgaga cccggaggag |
| | 181 | gttcgaagct gagtatgtga cagataagtc agataaatat gatgcacgtg atgttgaaag |
| | 241 | gctacaacaa gatgataact gggttgaaag ttacttatct tggagacata atattgtaga |
| | 301 | tgaaacactg aagatgctcg atgagagttt tcagtggagg aaagaaattt ctgtcaatga |
| | 361 | ccttaatgaa tcctccattc ccagatggtt attggaaatt ggtgttattt atctccatgg |
| | 421 | ttatgacaaa gaaggtaaca aattgttctg gatcagggtg aagtatcatg taaaagacca |
| | 481 | gaaaaccata ttggacaaaa agaagctcat agcattctgg ttggaacgtt atgctaagag |
| | 541 | ggaaaatggg aaacctgtaa cagtgatgtt tgacctgtca gaaactggaa taaatagcat |
| | 601 | tgacatggac tttgtacgct ttatcatcaa ctgctttaag gtttattacc ctaaataccct |
| | 661 | ctcaaaaata gtgatctttg atatgccttg gttaatgaat gctgcttttca aaattgtgaa |
| | 721 | aacctggctt ggtccagaag cagtgagctt gttgaagttt acaagcaaaa atgaagtcca |
| | 781 | ggactatgtc agtgtagaat acctgcctcc ccacatgggt ggaactgatc ctttcaagta |
| | 841 | tagctatcca ccactagtag atgatgactt ccagacccca ctgtgtgaga atgggcctat |
| | 901 | taccagtgag gatgaaactt caagtaaaga agacatagaa agtgatggca aagaaacatt |
| | 961 | ggaaacaatt tctaatgaag aacaaacacc tcttcttaaa aagattaacc caaccgaatc |
| | 1021 | tacttccaaa gcagaagaaa atgaaaaagt tgattcaaaa gtgaaagctt tcaagaaacc |
| | 1081 | attgagtgta tttaaaggcc ccttactaca catcagccca gcagaagaac tgtactttgg |
| | 1141 | aagtacagaa tccggagaga agaaaacctt aatagtgttg acaaatgtaa ctaaaaatat |
| | 1201 | agtggcattt aaggtgagaa caacagctcc agaaaaatac agagtcaagc caagcaatag |
| | 1261 | cagctgtgac ccgggtgcat cagtggatat agttgtgtct ccccatgggg gtttaacagt |
| | 1321 | ctctgcccaa gaccgttttc tgataatggc tgcagaaatg gaacagtcat ctggcacagg |
| | 1381 | cccagcagaa ttaactcagt tttggaaaga agttcccaga aacaaagtga tggaacatag |
| | 1441 | gttaagatgc catactgttg aaagcagtaa accaaacact cttacgttaa aagacaatgc |
| | 1501 | tttcaatatg tcagataaaa ccagtgaaga tatatgtcta caatacagtt aaagaagtgg |
| | 1561 | tgccgggtag gaaccacggt tccttcgtcc attagttgga aaaagtaaca gacctaaaac |
| | 1621 | tctaccaagc tactaaaaac attgcacatc tgtgcttcct aaaaggaaat atgcagcacg |
| | 1681 | tggaggggaa cacatacatg tcttgaaaat aaactgctag aataaagaaa tgctggagaa |
| | 1741 | attgattata agagactata gctatttagt aaagtaagta aaggcaatgc cattgtgtaa |
| | 1801 | attaatagtt taaatataat ttatttttctc cttttgatct gaatacttttt aaagcttaag |
| | 1861 | ttttatcgtg taaatacatt agctaaactg aaaagtataa gtaacatgct tgttgcagc |
| | 1921 | caaaaaatgt aatctgcttt tttatgacag aattattata gctgagctga cttactagct |
| | 1981 | tttctatact atgtatatag aagaacatgt atattgagaa agaaaacata cttatataga |
| | 2041 | ggaatttatg taaccatgac tttgtaattt tgagaattcc tcccagtgat ggtcagtatt |
| | 2101 | cttttggaat gtaaaccgat ttaatgccaa accacttaa cctttgtttc tcagtgttcc |
| | 2161 | ttaacagcct gcctttttatt aatctcaggc tttttttatga acactctcat ttcagtagaa |
| | 2221 | tttggaaaac taagcgtggt tggaatttct ttgaattctg ttagtaatgc ccaaaagaaa |
| | 2281 | agtctcaagc agtcccccta tccagtcatt tttatggagt ttcatgttgt ccactatagc |
| | 2341 | tggacactga accttttgcc taatttatta taaaggcctg accctctatt gtcccatctt |
| | 2401 | caccccatt ccagagcaga gggtctctgt ggaccatga attgcactgt ctccctcctc |
| | 2461 | attttcaaat gaaaggtatt agatataaat tttttttgaaa ggttagttgt ttgagatgct |
| | 2521 | aagcaggata ataaattttag attttaaaat gttccctgta aaagtcagcc catgacaagg |
| | 2581 | aaatttacaa aatactagag tatctagaag ggtgaaaaca aaaaaaaata aaaagaaaca |
| | 2641 | cagacgccca ggtgtcagct ctccgttttaa agaatgaaaa atgtaactca tgatgatctg |
| | 2701 | tgaaaccttc aaactaggac caattgactt acttgatatt ctgcctttga tatggtagta |
| | 2761 | cccacccggt attcctaaaa tcctaaaaag atacaccttg cagtagcaga ggcaatgaca |

TABLE 5-continued

Sequences

| SEQ ID NO: | Sequence | | | | | |
|---|---|---|---|---|---|---|
| | 2821 | tgagtttgtt | ttctcattaa | tatgaccagt | ttgggtctat | gttggttcac atgtacatct |
| | 2881 | actttatatg | aaagaaaaaa | cagttgtctg | cctgtaaaat | gttgagtttc gattgagcca |
| | 2941 | tgtttggaga | ttttattact | attctgaagg | gtagtgttgt | tggttttcat cttcaagaag |
| | 3001 | ttgattccaa | aactgagtta | tgaagaatga | tataacagtt | ccttcaaaat tggcctagga |
| | 3061 | aataaaacct | taaaaggaca | ctggtgtgct | actttgtctt | aatttgggct tttctgtttc |
| | 3121 | agtttgccac | ctccagctgt | gaaatggact | gcagtccacc | ctaagtactg tgcacagtat |
| | 3181 | ctccctgtgt | gtgtgcacag | tggcttcccc | ttacatggta | gattttggc cttaatataa |
| | 3241 | tctaatccca | aagtagttgt | gtatgttttc | tgttccttgg | caaataaatg aagaaataat |
| | 3301 | tagccaagat | tgaaaatgta | ttgtcctaac | ggtgtccctt | taatgtttca tatgaaaaat |
| | 3361 | tatgttgacc | cactaaaata | tccttgctca | atgtctggtc | agttgaattt aataacatat |
| | 3421 | cttgttaatg | tttgtgtgtc | tattaaatgt | gactaagcag | gattactgaa aattcactat |
| | 3481 | aaaatcaaag | gcatctaaac | gtttgtactt | gtcttgatta | atcatatatt tacacttgat |
| | 3541 | tttttctgt | cttcatttgt | ttttatttaa | tcataattgc | atgattttt tggtactcta |
| | 3601 | atcagtaatt | ttatttttaa | tcatgtcatt | acctattcat | gaccaaatta ccaaggaacc |
| | 3661 | aacatttaga | tttagatatt | tgttttcact | taggaatgga | aattaataga ttttccatga |
| | 3721 | aagcattagt | gaaatatcat | taccttgatc | tgcaagtagc | ctaaaaatgc gattgctggt |
| | 3781 | aaacctggcc | tcaaatttca | tactaccata | actgttttta | tatattgcca ctaatttttga |
| | 3841 | ctggatttaa | tagcacttta | ttgtacaact | acaaaaaaaa | atatattcct agaattgttg |
| | 3901 | ccagtgtaa | | | | |

All publications, patents and patent applications mentioned in this application are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An antibody or antigen binding fragment thereof that binds MOSPD2 comprising:
   a heavy chain CDR1 comprising the amino acid sequence of SEQ ID NO:1;
   a heavy chain CDR2 comprising the amino acid sequence of any one of SEQ ID NOs:2-8;
   a heavy chain CDR3 comprising the amino acid sequence of SEQ ID NO:9;
   a light chain CDR1 comprising the amino acid sequence of any one of SEQ ID NOs:10-18;
   a light chain CDR2 comprising the amino acid sequence of any one of SEQ ID NOs:19-24; and
   a light chain CDR3 comprising the amino acid sequence of SEQ ID NO:25.

2. The antibody or antigen binding fragment thereof of claim 1, wherein the antigen binding fragment is a Fab, Fab', F(ab')2, Fv, scFv, or sdFv fragment.

3. The antibody or antigen binding fragment thereof of claim 1, wherein the antibody or antigen binding fragment thereof binds to MOSPD2 with a Ka value of from about $1\times10^5$ (1/Ms) to about $7\times10^6$ (1/Ms); a Kd value of from about $1\times10^{-4}$ (1/s) to about 0.4 (1/s); and/or a calculated KD of from about $2\times10^{-10}$ (M) to about $6\times10^{-8}$ (M).

4. The antibody or antigen binding fragment thereof of claim 1, wherein the MOSPD2 is human MOSPD2.

5. A nucleic acid encoding the antibody or antigen binding fragment thereof of claim 1.

6. A vector comprising the nucleic acid of claim 5.

7. A cell comprising the vector of claim 6.

8. A composition comprising the antibody or antigen binding fragment thereof of claim 1, and a carrier.

9. A kit comprising the antibody or antigen binding fragment of claim 1, and an instruction for use.

10. The antibody or antigen binding fragment thereof claim 1, wherein the heavy chain CDR2 comprises the amino acid sequence of SEQ ID NO:4.

11. The antibody or antigen binding fragment thereof claim 1, wherein the light chain CDR1 comprises the amino acid sequence of SEQ ID NO:11.

12. The antibody or antigen binding fragment thereof of claim 1, wherein the light chain CDR2 comprises the amino acid sequence of SEQ ID NO:20.

13. The antibody or antigen binding fragment thereof of claim 1, wherein:
   the heavy chain CDR2 comprises the amino acid sequence of SEQ ID NO:4;
   the light chain CDR1 comprises the amino acid sequence of SEQ ID NO:11; and
   the light chain CDR2 comprises the amino acid sequence of SEQ ID NO:20.

14. A composition comprising the antibody or antigen binding fragment thereof of claim 13, and a carrier.

15. A kit comprising the antibody or antigen binding fragment of claim 13, and an instruction for use.

16. A method of inhibiting migration of monocytes in a subject in need thereof, comprising administering to the subject the antibody or antigen binding fragment thereof of claim 1, wherein the subject has cancer.

17. A method of inhibiting migration of monocytes in a subject in need thereof, comprising administering to the subject the antibody or antigen binding fragment thereof of claim 1, wherein the subject has rheumatoid arthritis.

18. A method of inhibiting migration of monocytes in a subject in need thereof, comprising administering to the subject the antibody or antigen binding fragment thereof of claim 1, wherein the subject has multiple sclerosis.

19. A method of inhibiting migration of monocytes in a subject in need thereof, comprising administering to the subject the antibody or antigen binding fragment thereof of claim 1, wherein the subject has Crohn's disease.

20. A method of treating nonalcoholic steatohepatitis in subject in need thereof, comprising administering to the subject the antibody or antigen binding fragment thereof of claim 1.

21. A method of treating liver fibrosis in subject in need thereof, comprising administering to the subject the antibody or antigen binding fragment thereof of claim 1.

22. A method of treating ulcerative colitis in subject in need thereof, comprising administering to the subject the antibody or antigen binding fragment thereof of claim 1.

23. A method of inhibiting migration of monocytes in a subject in need thereof, comprising administering to the subject the antibody or antigen binding fragment thereof of claim 13, wherein the subject has cancer.

24. A method of inhibiting migration of monocytes in a subject in need thereof, comprising administering to the subject the antibody or antigen binding fragment thereof of claim 13, wherein the subject has rheumatoid arthritis.

25. A method of inhibiting migration of monocytes in a subject in need thereof, comprising administering to the subject the antibody or antigen binding fragment thereof of claim 13, wherein the subject has multiple sclerosis.

26. A method of inhibiting migration of monocytes in a subject in need thereof, comprising administering to the subject the antibody or antigen binding fragment thereof of claim 13, wherein the subject has Crohn's disease.

27. A method of treating nonalcoholic steatohepatitis in subject in need thereof, comprising administering to the subject the antibody or antigen binding fragment thereof of claim 13.

28. A method of treating liver fibrosis in subject in need thereof, comprising administering to the subject the antibody or antigen binding fragment thereof of claim 13.

29. A method of treating ulcerative colitis in subject in need thereof, comprising administering to the subject the antibody or antigen binding fragment thereof of claim 13.

* * * * *

SEQUENCE LISTING

<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: Anti-MOSPD2 Antibodies VH CDR1

<400> SEQUENCE: 1

Ser Tyr Ser Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 2

Thr Ile Ser Arg Gly Gly Ser Tyr Thr Tyr Tyr Pro Asp Ser Val Lys
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 3

Thr Ile Ser Arg Ser Ser Ser Tyr Ile Tyr Tyr Ala Asp Ser Val Lys
1               5                   10                  15

Gly

<210> SEQ ID NO 4
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 4

Thr Ile Ser Arg Gly Gly Ser Asn Lys Tyr Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 5

Thr Ile Ser Arg Ser Gly Gly Ser Thr Ser Tyr Ala Gln Lys Val Gln
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 6

Thr Ile Ser Arg Gly Gly Ser Asn Lys Tyr Tyr Ala Glu Ser Val Lys
1               5                   10                  15

Gly

<210> SEQ ID NO 7
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 7

Thr Ile Ser Arg Gly Gly Ser Tyr Thr Tyr Tyr Pro Glu Ser Val Lys
1               5                   10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: Anti-MOSPD2 Antibodies VH CDR2

<400> SEQUENCE: 8

Thr Ile Ser Arg Gly Gly Ser Tyr Thr Tyr Tyr Pro Asp Thr Val Lys
1               5                   10                  15

Gly

```
<210> SEQ ID NO 9
<211> LENGTH: 2
<212> TYPE: PRT
<213> ORGANISM: Artificial Sequence
<220> FEATURE:
<223> OTHER INFORMATION: Anti-MOSPD2 Antibodies VH CDR3

<400> SEQUENCE: 9

Gly Lys
1

<210> SEQ ID NO 10
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 10

Lys Ser Ser Gln Ser Leu Leu Asp Ser Asp Gly Lys Thr Asn Leu Asn
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 11

Lys Ser Ser Gln Ser Leu Val Asp Ser Asp Ala Lys Thr Asn Leu Asn
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 12

Arg Ser Ser Gln Ser Leu Val Asp Ser Asp Ala Lys Thr Asn Leu Asn
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 13

Lys Ser Ser Gln Ser Leu Leu Glu Ser Glu Gly Lys Thr Asn Leu Asn
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 14

Lys Ser Ser Gln Ser Leu Val Glu Ser Glu Gly Lys Thr Asn Leu Asn
1               5                   10                  15

<210> SEQ ID NO 15
```

```
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 15

Lys Ser Ser Gln Ser Leu Leu Glu Ser Asp Gly Lys Thr Asn Leu Asn
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 16

Lys Ser Ser Gln Ser Leu Leu Asp Thr Asp Gly Lys Thr Asn Leu Asn
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 17

Lys Ser Ser Gln Ser Leu Leu Asp Ser Glu Gly Lys Thr Asn Leu Asn
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Anti-MOSPD2 Antibodies VL CDR1

<400> SEQUENCE: 18

Lys Ser Ser Gln Ser Leu Leu Asp Ser Asp Ala Lys Thr Asn Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 19

Leu Val Ser Lys Leu Asp Ser
1               5

<210> SEQ ID NO 20
<211> LENGTH: 7
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 20

Leu Val Ser Lys Arg Asp Ser
1               5

<210> SEQ ID NO 21
<211> LENGTH: 7
```

```
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 21

Leu Val Ser Asn Arg Asp Ser
1               5

<210> SEQ ID NO 22
<211> LENGTH: 7
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 22

Leu Val Ser Lys Leu Glu Ser
1               5

<210> SEQ ID NO 23
<211> LENGTH: 7
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 23

Leu Val Ser Lys Arg Glu Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Anti-MOSPD2 Antibodies VL CDR2

<400> SEQUENCE: 24

Leu Val Ser Lys Leu Asp Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Anti-MOSPD2 Antibodies VL CDR3

<400> SEQUENCE: 25

Trp Gln Gly Thr His Phe Pro Arg Thr
1               5

<210> SEQ ID NO 26
<211> LENGTH: 518
<212> TYPE: PRT
<213> ORGANISM: Artificial Sequence
<220> FEATURE:
<223> OTHER INFORMATION: Homo sapiens motile sperm domain containing 2
      (MOSPD2), protein variant 1

<400> SEQUENCE: 26

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
                20                  25                  30
```

-continued

Asp Ala Arg Asp Val Glu Arg Leu Gln Gln Asp Asp Asn Trp Val Glu
            35                  40                  45

Ser Tyr Leu Ser Trp Arg His Asn Ile Val Asp Glu Thr Leu Lys Met
 50                  55                  60

Leu Asp Glu Ser Phe Gln Trp Arg Lys Glu Ile Ser Val Asn Asp Leu
 65                  70                  75                  80

Asn Glu Ser Ser Ile Pro Arg Trp Leu Leu Glu Ile Gly Val Ile Tyr
                 85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
            115                 120                 125

Ile Ala Phe Trp Leu Glu Arg Tyr Ala Lys Arg Glu Asn Gly Lys Pro
 130                 135                 140

Val Thr Val Met Phe Asp Leu Ser Glu Thr Gly Ile Asn Ser Ile Asp
 145                 150                 155                 160

Met Asp Phe Val Arg Phe Ile Ile Asn Cys Phe Lys Val Tyr Tyr Pro
                 165                 170                 175

Lys Tyr Leu Ser Lys Ile Val Ile Phe Asp Met Pro Trp Leu Met Asn
            180                 185                 190

Ala Ala Phe Lys Ile Val Lys Thr Trp Leu Gly Pro Glu Ala Val Ser
            195                 200                 205

Leu Leu Lys Phe Thr Ser Lys Asn Glu Val Gln Asp Tyr Val Ser Val
            210                 215                 220

Glu Tyr Leu Pro Pro His Met Gly Gly Thr Asp Pro Phe Lys Tyr Ser
225                 230                 235                 240

Tyr Pro Pro Leu Val Asp Asp Phe Gln Thr Pro Leu Cys Glu Asn
                 245                 250                 255

Gly Pro Ile Thr Ser Glu Asp Glu Thr Ser Ser Lys Glu Asp Ile Glu
            260                 265                 270

Ser Asp Gly Lys Glu Thr Leu Glu Thr Ile Ser Asn Glu Glu Gln Thr
            275                 280                 285

Pro Leu Leu Lys Lys Ile Asn Pro Thr Glu Ser Thr Ser Lys Ala Glu
 290                 295                 300

Glu Asn Glu Lys Val Asp Ser Lys Val Lys Ala Phe Lys Lys Pro Leu
305                 310                 315                 320

Ser Val Phe Lys Gly Pro Leu Leu His Ile Ser Pro Ala Glu Glu Leu
                 325                 330                 335

Tyr Phe Gly Ser Thr Glu Ser Gly Glu Lys Lys Thr Leu Ile Val Leu
            340                 345                 350

Thr Asn Val Thr Lys Asn Ile Val Ala Phe Lys Val Arg Thr Thr Ala
            355                 360                 365

Pro Glu Lys Tyr Arg Val Lys Pro Ser Asn Ser Ser Cys Asp Pro Gly
 370                 375                 380

Ala Ser Val Asp Ile Val Val Ser Pro His Gly Gly Leu Thr Val Ser
385                 390                 395                 400

Ala Gln Asp Arg Phe Leu Ile Met Ala Ala Glu Met Glu Gln Ser Ser
                 405                 410                 415

Gly Thr Gly Pro Ala Glu Leu Thr Gln Phe Trp Lys Glu Val Pro Arg
            420                 425                 430

Asn Lys Val Met Glu His Arg Leu Arg Cys His Thr Val Glu Ser Ser
            435                 440                 445

Lys Pro Asn Thr Leu Thr Leu Lys Asp Asn Ala Phe Asn Met Ser Asp

```
                450                 455                 460
Lys Thr Ser Glu Asp Ile Cys Leu Gln Leu Ser Arg Leu Leu Glu Ser
465                 470                 475                 480

Asn Arg Lys Leu Glu Asp Gln Val Gln Arg Cys Ile Trp Phe Gln Gln
                485                 490                 495

Leu Leu Leu Ser Leu Thr Met Leu Leu Ala Phe Val Thr Ser Phe
                500                 505                 510

Phe Tyr Leu Leu Tyr Ser
        515

<210> SEQ ID NO 27
<211> LENGTH: 455
<212> TYPE: PRT
<213> ORGANISM: Artificial Sequence
<220> FEATURE:
<223> OTHER INFORMATION: Homo sapiens motile sperm domain containing 2
      (MOSPD2), protein variant 2

<400> SEQUENCE: 27

Met Leu Asp Glu Ser Phe Gln Trp Arg Lys Glu Ile Ser Val Asn Asp
1               5                   10                  15

Leu Asn Glu Ser Ser Ile Pro Arg Trp Leu Glu Ile Gly Val Ile
                20                  25                  30

Tyr Leu His Gly Tyr Asp Lys Glu Gly Asn Lys Leu Phe Trp Ile Arg
            35                  40                  45

Val Lys Tyr His Val Lys Asp Gln Lys Thr Ile Leu Asp Lys Lys Lys
    50                  55                  60

Leu Ile Ala Phe Trp Leu Glu Arg Tyr Ala Lys Arg Glu Asn Gly Lys
65                  70                  75                  80

Pro Val Thr Val Met Phe Asp Leu Ser Glu Thr Gly Ile Asn Ser Ile
                85                  90                  95

Asp Met Asp Phe Val Arg Phe Ile Ile Asn Cys Phe Lys Val Tyr Tyr
            100                 105                 110

Pro Lys Tyr Leu Ser Lys Ile Val Ile Phe Asp Met Pro Trp Leu Met
        115                 120                 125

Asn Ala Ala Phe Lys Ile Val Lys Thr Trp Leu Gly Pro Glu Ala Val
    130                 135                 140

Ser Leu Leu Lys Phe Thr Ser Lys Asn Glu Val Gln Asp Tyr Val Ser
145                 150                 155                 160

Val Glu Tyr Leu Pro Pro His Met Gly Gly Thr Asp Pro Phe Lys Tyr
                165                 170                 175

Ser Tyr Pro Pro Leu Val Asp Asp Phe Gln Thr Pro Leu Cys Glu
            180                 185                 190

Asn Gly Pro Ile Thr Ser Glu Asp Glu Thr Ser Ser Lys Glu Asp Ile
        195                 200                 205

Glu Ser Asp Gly Lys Glu Thr Leu Glu Thr Ile Ser Asn Glu Glu Gln
    210                 215                 220

Thr Pro Leu Leu Lys Lys Ile Asn Pro Thr Glu Ser Thr Ser Lys Ala
225                 230                 235                 240

Glu Glu Asn Glu Lys Val Asp Ser Lys Val Lys Ala Phe Lys Lys Pro
                245                 250                 255

Leu Ser Val Phe Lys Gly Pro Leu Leu His Ile Ser Pro Ala Glu Glu
            260                 265                 270

Leu Tyr Phe Gly Ser Thr Glu Ser Gly Glu Lys Lys Thr Leu Ile Val
        275                 280                 285
```

```
Leu Thr Asn Val Thr Lys Asn Ile Val Ala Phe Lys Val Arg Thr Thr
            290                 295                 300

Ala Pro Glu Lys Tyr Arg Val Lys Pro Ser Asn Ser Ser Cys Asp Pro
305                 310                 315                 320

Gly Ala Ser Val Asp Ile Val Val Ser Pro His Gly Gly Leu Thr Val
                325                 330                 335

Ser Ala Gln Asp Arg Phe Leu Ile Met Ala Ala Glu Met Glu Gln Ser
                340                 345                 350

Ser Gly Thr Gly Pro Ala Glu Leu Thr Gln Phe Trp Lys Glu Val Pro
                355                 360                 365

Arg Asn Lys Val Met Glu His Arg Leu Arg Cys His Thr Val Glu Ser
370                 375                 380

Ser Lys Pro Asn Thr Leu Thr Leu Lys Asp Asn Ala Phe Asn Met Ser
385                 390                 395                 400

Asp Lys Thr Ser Glu Asp Ile Cys Leu Gln Leu Ser Arg Leu Leu Glu
                405                 410                 415

Ser Asn Arg Lys Leu Glu Asp Gln Val Gln Arg Cys Ile Trp Phe Gln
                420                 425                 430

Gln Leu Leu Leu Ser Leu Thr Met Leu Leu Leu Ala Phe Val Thr Ser
            435                 440                 445

Phe Phe Tyr Leu Leu Tyr Ser
450                 455

<210> SEQ ID NO 28
<211> LENGTH: 486
<212> TYPE: PRT
<213> ORGANISM: Artificial Sequence
<220> FEATURE:
<223> OTHER INFORMATION: Homo sapiens motile sperm domain containing 2
      (MOSPD2), protein variant 3

<400> SEQUENCE: 28

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
            20                  25                  30

Asp Ala Arg Asp Val Glu Arg Leu Gln Gln Asp Asp Asn Trp Val Glu
        35                  40                  45

Ser Tyr Leu Ser Trp Arg His Asn Ile Val Asp Glu Thr Leu Lys Met
    50                  55                  60

Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
            100                 105                 110

Lys Tyr His Val Lys Asp Gln Lys Thr Ile Leu Asp Lys Lys Lys Leu
        115                 120                 125

Ile Ala Phe Trp Leu Glu Arg Tyr Ala Lys Arg Glu Asn Gly Lys Pro
    130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
            180                 185                 190
```

Ala Ala Phe Lys Ile Val Lys Thr Trp Leu Gly Pro Glu Ala Val Ser
            195                 200                 205

Leu Leu Lys Phe Thr Ser Lys Asn Glu Val Gln Asp Tyr Val Ser Val
210                 215                 220

Glu Tyr Leu Pro Pro His Met Gly Gly Thr Asp Pro Phe Lys Tyr Ser
225                 230                 235                 240

Tyr Pro Pro Leu Val Asp Asp Phe Gln Thr Pro Leu Cys Glu Asn
            245                 250                 255

Gly Pro Ile Thr Ser Glu Asp Glu Thr Ser Ser Lys Glu Asp Ile Glu
            260                 265                 270

Ser Asp Gly Lys Glu Thr Leu Glu Thr Ile Ser Asn Glu Glu Gln Thr
            275                 280                 285

Pro Leu Leu Lys Lys Ile Asn Pro Thr Glu Ser Thr Ser Lys Ala Glu
            290                 295                 300

Glu Asn Glu Lys Val Asp Ser Lys Val Lys Ala Phe Lys Lys Pro Leu
305                 310                 315                 320

Ser Val Phe Lys Gly Pro Leu Leu His Ile Ser Pro Ala Glu Glu Leu
            325                 330                 335

Tyr Phe Gly Ser Thr Glu Ser Gly Glu Lys Lys Thr Leu Ile Val Leu
            340                 345                 350

Thr Asn Val Thr Lys Asn Ile Val Ala Phe Lys Val Arg Thr Thr Ala
            355                 360                 365

Pro Glu Lys Tyr Arg Val Lys Pro Ser Asn Ser Ser Cys Asp Pro Gly
            370                 375                 380

Ala Ser Val Asp Ile Val Val Ser Pro His Gly Gly Leu Thr Val Ser
385                 390                 395                 400

Ala Gln Asp Arg Phe Leu Ile Met Ala Ala Glu Met Glu Gln Ser Ser
            405                 410                 415

Gly Thr Gly Pro Ala Glu Leu Thr Gln Phe Trp Lys Glu Val Pro Arg
            420                 425                 430

Asn Lys Val Met Glu His Arg Leu Arg Cys His Thr Val Glu Ser Ser
            435                 440                 445

Lys Pro Asn Thr Leu Thr Leu Lys Asp Asn Ala Phe Asn Met Ser Asp
            450                 455                 460

Lys Thr Ser Glu Asp Ile Cys Leu Gln Phe Ala Thr Ser Ser Cys Glu
465                 470                 475                 480

Met Asp Cys Ser Pro Pro
            485

<210> SEQ ID NO 29
<211> LENGTH: 475
<212> TYPE: PRT
<213> ORGANISM: Artificial Sequence
<220> FEATURE:
<223> OTHER INFORMATION: Homo sapiens motile sperm domain containing 2
      (MOSPD2), protein variant X2

<400> SEQUENCE: 29

Met Ala Glu Asn His Ala Gln Asn Lys Ala Lys Leu Ile Ser Glu Thr
1               5                   10                  15

Arg Arg Arg Phe Glu Ala Glu Tyr Val Thr Asp Lys Ser Asp Lys Tyr
            20                  25                  30

Asp Ala Arg Asp Val Glu Arg Leu Gln Gln Asp Asp Asn Trp Val Glu
            35                  40                  45

Ser Tyr Leu Ser Trp Arg His Asn Ile Val Asp Glu Thr Leu Lys Met

```
                50                  55                  60
Leu Asp Glu Ser Phe Gln Trp Arg Lys Glu Ile Ser Val Asn Asp Leu
65                  70                  75                  80

Asn Glu Ser Ser Ile Pro Arg Trp Leu Leu Glu Ile Gly Val Ile Tyr
                85                  90                  95

Leu His Gly Tyr Asp Lys Glu Gly Asn Lys Leu Phe Trp Ile Arg Val
                100                 105                 110

Lys Tyr His Val Lys Asp Gln Lys Thr Ile Leu Asp Lys Lys Lys Leu
                115                 120                 125

Ile Ala Phe Trp Leu Glu Arg Tyr Ala Lys Arg Glu Asn Gly Lys Pro
130                 135                 140

Val Thr Val Met Phe Asp Leu Ser Glu Thr Gly Ile Asn Ser Ile Asp
145                 150                 155                 160

Met Asp Phe Val Arg Phe Ile Ile Asn Cys Phe Lys Val Tyr Tyr Pro
                165                 170                 175

Lys Tyr Leu Ser Lys Ile Val Ile Phe Asp Met Pro Trp Leu Met Asn
                180                 185                 190

Ala Ala Phe Lys Ile Val Lys Thr Trp Leu Gly Pro Glu Ala Val Ser
                195                 200                 205

Leu Leu Lys Phe Thr Ser Lys Asn Glu Val Gln Asp Tyr Val Ser Val
210                 215                 220

Glu Tyr Leu Pro Pro His Met Gly Gly Thr Asp Pro Phe Lys Tyr Ser
225                 230                 235                 240

Tyr Pro Pro Leu Val Asp Asp Phe Gln Thr Pro Leu Cys Glu Asn
                245                 250                 255

Gly Pro Ile Thr Ser Glu Asp Glu Thr Ser Ser Lys Glu Asp Ile Glu
                260                 265                 270

Ser Asp Gly Lys Glu Thr Leu Glu Thr Ile Ser Asn Glu Glu Gln Thr
                275                 280                 285

Pro Leu Leu Lys Lys Ile Asn Pro Thr Glu Ser Thr Ser Lys Ala Glu
                290                 295                 300

Glu Asn Glu Lys Val Asp Ser Lys Val Lys Ala Phe Lys Lys Pro Leu
305                 310                 315                 320

Ser Val Phe Lys Gly Pro Leu Leu His Ile Ser Pro Ala Glu Glu Leu
                325                 330                 335

Tyr Phe Gly Ser Thr Glu Ser Gly Glu Lys Lys Thr Leu Ile Val Leu
                340                 345                 350

Thr Asn Val Thr Lys Asn Ile Val Ala Phe Lys Val Arg Thr Thr Ala
                355                 360                 365

Pro Glu Lys Tyr Arg Val Lys Pro Ser Asn Ser Ser Cys Asp Pro Gly
370                 375                 380

Ala Ser Val Asp Ile Val Ser Pro His Gly Gly Leu Thr Val Ser
385                 390                 395                 400

Ala Gln Asp Arg Phe Leu Ile Met Ala Ala Glu Met Glu Gln Ser Ser
                405                 410                 415

Gly Thr Gly Pro Ala Glu Leu Thr Gln Phe Trp Lys Glu Val Pro Arg
                420                 425                 430

Asn Lys Val Met Glu His Arg Leu Arg Cys His Thr Val Glu Ser Ser
                435                 440                 445

Lys Pro Asn Thr Leu Thr Leu Lys Asp Asn Ala Phe Asn Met Ser Asp
450                 455                 460

Lys Thr Ser Glu Asp Ile Cys Leu Gln Tyr Ser
465                 470                 475
```

<210> SEQ ID NO 30
<211> LENGTH: 3218
<212> TYPE: DNA
<213> ORGANISM: Artificial Sequence
<220> FEATURE:
<223> OTHER INFORMATION: Homo sapiens motile sperm domain containing 2 (MOSPD2), transcript variant 1, mRNA

<400> SEQUENCE: 30

```
accgcctccc cctcccaccc ttctctgtct acctctgggc ggactgccgg gtgatgagat      60
actcggtcgg cgacggtaga acgggcgacg gcgacaaccg caatcacatc cacgacggtg     120
atcatggcag agaatcacgc ccagaataaa gccaagctca tctctgagac ccggaggagg     180
ttcgaagctg agtatgtgac agataagtca gataaatatg atgcacgtga tgttgaaagg     240
ctacaacaag atgataactg ggttgaaagt tacttatctt ggagacataa tattgtagat     300
gaaacactga gatgctcga tgagagtttt cagtggagga agaaatttc tgtcaatgac      360
cttaatgaat cctccattcc cagatggtta ttggaaattg tgttatttta tctccatggt     420
tatgacaaag aaggtaacaa attgttctgg atcagggtga agtatcatgt aaaagaccag     480
aaaaccatat tggacaaaaa gaagctcata gcattctggt tggaacgtta tgctaagagg     540
gaaaatggga aacctgtaac agtgatgttt gacctgtcag aaactggaat aaatagcatt     600
gacatggact ttgtacgctt tatcatcaac tgctttaagg tttattaccc taaatacctc     660
tcaaaaatag tgatctttga tatgccttgg ttaatgaatg ctgctttcaa aattgtgaaa     720
acctggcttg gtccagaagc agtgagcttg ttgaagttta caagcaaaaa tgaagtccag     780
gactatgtca gtgtagaata cctgcctccc cacatgggtg gaactgatcc tttcaagtat     840
agctatccac cactagtaga tgatgacttc cagaccccac tgtgtgagaa tgggcctatt     900
accagtgagg atgaaacttc aagtaaagaa gacatagaaa gtgatggcaa agaaacattg     960
gaaacaattt ctaatgaaga acaaacacct cttcttaaaa agattaaccc aaccgaatct    1020
acttccaaag cagaagaaaa tgaaaaagtt gattcaaaag tgaaagcttt caagaaacca    1080
ttgagtgtat ttaaaggccc cttactacac atcagcccag cagaagaact gtactttgga    1140
agtacagaat ccggagagaa gaaaaccta atagtgttga caaatgtaac taaaaatata    1200
gtggcattta aggtgagaac aacagctcca gaaaaataca gagtcaagcc aagcaatagc    1260
agctgtgacc cgggtgcatc agtggatata gttgtgtctc cccatggggg tttaacagtc    1320
tctgcccaag accgttttct gataatggct gcagaaatgg aacagtcatc tggcacaggc    1380
ccagcagaat taactcagtt ttggaaagaa gttcccagaa acaaagtgat ggaacatagg    1440
ttaagatgcc atactgttga aagcagtaaa ccaaacactc ttacgttaaa agacaatgct    1500
ttcaatatgt cagataaaac cagtgaagat atatgtctac aactcagtcg tttactagaa    1560
agcaatagga agcttgaaga ccaagttcag cgttgtatct ggttccagca gctgctgctt    1620
tccttaacaa tgctcttgct tgcttttgtc acctctttct tctatttatt gtacagttaa    1680
agaagtggtg ccgggtagga accacggttc cttcgtccat tagttggaaa agtaacaga    1740
cctaaaactc taccaagcta ctaaaaacat tgcacatctg tgcttcctaa aaggaaatat    1800
gcagcacgtg gaggggaaca catacatgtc ttgaaaataa actgctagaa taagaaatg    1860
ctggagaaat tgattataag agactatagc tatttagtaa agtaagtaaa ggcatatcca    1920
ttgtgtaaat taatagttta aatataattt atttttttcct tttgatctga atacttttaa    1980
agcttaagtt ttatcgtgta aatacattag ctaaactgaa aagtataagt aacatgcttt    2040
```

```
gttgcagcca aaaaatgtaa tctgctttt tatgacagaa ttattatagc tgagctgact    2100
tactagcttt tctatactat gtatatagaa gaacatgtat attgagaaag aaaacatact    2160
tatatagagg aatttatgta accatgactt tgtaattttg agaattcctc ccagtgatgg    2220
tcagtattct tttggaatgt aaaccgattt aatgccaaac caccttaacc tttgtttctc    2280
agtgttcctt aacagcctgc cttttattaa tctcaggctt ttttatgaac actctcattt    2340
cagtagaatt tggaaaacta agcgtggttg gaatttcttt gaattctgtt agtaatgccc    2400
aaaagaaaag tctcaagcag tcccccctatc cagtcatttt tatggagttt catgttgtcc    2460
actatagctg gacactgaac cttttgccta atttattata aaggcctgac cctctattgt    2520
cccatcttca cccccattcc agagcagagg agtctctgtg gaccatgaat tgcactgtct    2580
ccctcctcat ttctaaatga aaggtattag atataaattt ttttgaaagg ttagttgttt    2640
gagatgctaa gcaggataat aaatttagat tttaaaatgt tccctgtaaa agtcagccca    2700
tgacaaggaa atttacaaaa tactagagta tctagaaggg tgaaaacaaa aaaaaataaa    2760
aagaaacaca gacgcccagg tgtcagctct ccgtttaaag aatgaaaaat gtaactcatg    2820
atgatctgtg aaaccttcaa actaggacca attgacttac ttgatattct gcctttgata    2880
tggtagtacc cacccggtat tcctaaaatc ctaaaaagat acaccttgca gtagcagagg    2940
caatgacatg agtttgtttt ctcattaata tgaccagttt gggtctatgt tggttcacat    3000
gtacatctac tttatatgaa agaaaaaaca gttgtctgcc tgtaaaatgt tgagtttcga    3060
ttgagccatg tttggagatt ttattactat tctgaagggt agtgttgttg gttttcatct    3120
tcaagaagtt gattccaaaa ctgagttatg aagaatgata taacagttcc ttcaaaattg    3180
gcctaggaaa taaaacctta aaaggacaaa aaaaaaa                            3218
```

<210> SEQ ID NO 31
<211> LENGTH: 3183
<212> TYPE: DNA
<213> ORGANISM: Artificial Sequence
<220> FEATURE:
<223> OTHER INFORMATION: Homo sapiens motile sperm domain containing 2
      (MOSPD2), transcript variant 2, mRNA

<400> SEQUENCE: 31

```
agtcacaata ataggtactt aaaaacatgt catatgatag gaaactagaa taacacacct      60
ctaaataatc catggattac caacttctca gcaatggtgt aaattcttct gctaaataac     120
ccgtgggtta aagaggacat cacattggaa attccagagt acttaaaata agtcagataa     180
atatgatgca cgtgatgttg aaaggctaca acaagatgat aactgggttg aaagttactt     240
atcttggaga cataatattg tagatgaaac actgaagatg ctcgatgaga gttttcagtg     300
gaggaaagaa atttctgtca atgaccttaa tgaatcctcc attcccagat ggttattgga     360
aattggtgtt attatctcc atggttatga caaagaaggt aacaaattgt tctggatcag     420
ggtgaagtat catgtaaaag accagaaaac catattggac aaaaagaagc tcatagcatt     480
ctggttggaa cgttatgcta gagggaaaa tgggaaacct gtaacagtga tgtttgacct     540
gtcagaaact ggaataaata gcattgacat ggactttgta cgctttatca tcaactgctt     600
taaggtttat tacccctaaat acctctcaaa aatagtgatc tttgatatgc cttggttaat     660
gaatgctgct ttcaaaattg tgaaaacctg gcttggtcca gaagcagtga gcttgttgaa     720
gtttacaagc aaaaatgaag tccaggacta tgtcagtgta gaataccttgc ctccccacat     780 gggtggaact gatcctttca gtatagctta tccaccacta gtagatgatg acttccagac     840
```

```
cccactgtgt gagaatgggc ctattaccag tgaggatgaa acttcaagta aagaagacat    900
agaaagtgat ggcaaagaaa cattggaaac aatttctaat gaagaacaaa cacctcttct    960
taaaaagatt aacccaaccg aatctacttc caaagcagaa gaaaatgaaa aagttgattc   1020
aaaagtgaaa gctttcaaga aaccattgag tgtatttaaa ggccccttac tacacatcag   1080
cccagcagaa gaactgtact ttggaagtac agaatccgga gagaagaaaa ccttaatagt   1140
gttgacaaat gtaactaaaa atatagtggc atttaaggtg agaacaacag ctccagaaaa   1200
atacagagtc aagccaagca atagcagctg tgacccgggt gcatcagtgg atatagttgt   1260
gtctccccat gggggtttaa cagtctctgc ccaagaccgt tttctgataa tggctgcaga   1320
aatggaacag tcatctggca caggcccagc agaattaact cagttttgga agaagttcc    1380
cagaaacaaa gtgatggaac ataggttaag atgccatact gttgaaagca gtaaaccaaa   1440
cactcttacg ttaaaagaca atgctttcaa tatgtcagat aaaaccagtg aagatatatg   1500
tctacaactc agtcgtttac tagaaagcaa taggaagctt gaagaccaag ttcagcgttg   1560
tatctggttc cagcagctgc tgcttttcct aacaatgctc ttgcttgctt ttgtcacctc   1620
tttcttctat ttattgtaca gttaaagaag tggtgccggg taggaaccac ggttccttcg   1680
tccattagtt ggaaaaagta acagacctaa aactctacca agctactaaa aacattgcac   1740
atctgtgctt cctaaaagga aatatgcagc acgtggaggg gaacacatac atgtcttgaa   1800
aataaactgc tagaataaag aaatgctgga gaaattgatt ataagagact atagctattt   1860
agtaaagtaa gtaaaggcat atccattgtg taaattaata gtttaaatat aatttatttt   1920
ttcctttga  tctgaatact tttaaagctt aagttttatc gtgtaaatac attagctaaa   1980
ctgaaaagta taagtaacat gctttgttgc agccaaaaaa tgtaatctgc tttttatga    2040
cagaattatt atagctgagc tgacttacta gcttttctat actatgtata tagaagaaca   2100
tgtatattga gaaagaaaac atactttatat agaggaattt atgtaaccat gactttgtaa   2160
ttttgagaat tcctcccagt gatggtcagt attcttttgg aatgtaaacc gatttaatgc   2220
caaaccacct taacctttgt ttctcagtgt tccttaacag cctgccttt  attaatctca   2280
ggctttttta tgaacactct catttcagta gaatttggaa aactaagcgt ggttggaatt   2340
tcttttgaatt ctgttagtaa tgcccaaaag aaaagtctca agcagtcccc ctatccagtc   2400
attttttatgg agtttcatgt tgtccactat agctggacac tgaaccttttt gcctaattta   2460
ttataaaggc ctgaccctct attgtcccat cttcaccccc attccagagc agaggagtct   2520
ctgtggacca tgaattgcac tgtctccctc ctcatttcta atgaaaggt  attagatata   2580
aatttttttg aaaggttagt tgtttgagat gctaagcagg ataataaatt tagattttaa   2640
aatgttccct gtaaagtca  gcccatgaca aggaaattta caaatacta  gagtatctag   2700
aagggtgaaa acaaaaaaaa ataaaaagaa acacagacgc ccaggtgtca gctctccgtt   2760
taaagaatga aaaatgtaac tcatgatgat ctgtgaaacc ttcaaactag gaccaattga   2820
cttacttgat attctgcctt tgatatggta gtacccaccc ggtattccta aaatcctaaa   2880
aagatacacc ttgcagtagc agaggcaatg acatgagttt gttttctcat taatatgacc   2940
agtttgggtc tatgttggtt cacatgtaca tctactttat atgaaagaaa aaacagttgt   3000
ctgcctgtaa aatgttgagt ttcgattgag ccatgtttgg agattttatt actattctga   3060
agggtagtgt tgttggtttt catcttcaag aagttgattc caaaactgag ttatgaagaa   3120
tgatataaca gttccttcaa aattggccta ggaaataaaa ccttaaaagg acaaaaaaaa   3180
```

| | |
|---|---:|
| aaa | 3183 |

<210> SEQ ID NO 32
<211> LENGTH: 2320
<212> TYPE: DNA
<213> ORGANISM: Artificial Sequence
<220> FEATURE:
<223> OTHER INFORMATION: Homo sapiens motile sperm domain containing 2 (MOSPD2), transcript variant 3, mRNA

<400> SEQUENCE: 32

| | |
|---|---:|
| accgcctccc cctcccaccc ttctctgtct acctctgggc gggactgccg ggtgatgaga | 60 |
| tactcggtcg gcgacggtag aacgggcgac ggcgacaacc gcaatcacat ccacgacggt | 120 |
| gatcatggca gagaatcacg cccagaataa agccaagctc atctctgaga cccggaggag | 180 |
| gttcgaagct gagtatgtga cagataagtc agataaatat gatgcacgtg atgttgaaag | 240 |
| gctacaacaa gatgataact gggttgaaag ttacttatct tggagacata atattgtaga | 300 |
| tgaaacactg aagatgctcg atgagagttt tcagtggagg aaagaaattt ctgtcaatga | 360 |
| ccttaatgaa tcctccattc ccagatggtt attggaaatt ggtgttattt atctccatgg | 420 |
| ttatgacaaa gaaggtaaca aattgttctg gatcagggtg aagtatcatg taaaagacca | 480 |
| gaaaaccata ttggacaaaa agaagctcat agcattctgg ttggaacgtt atgctaagag | 540 |
| ggaaaatggg aaacctgtaa cagtgatgtt tgacctgtca gaaactggaa taaatagcat | 600 |
| tgacatggac tttgtacgct ttatcatcaa ctgctttaag gtttattacc ctaaatacct | 660 |
| ctcaaaaata gtgatctttg atatgccttg gttaatgaat gctgctttca aaattgtgaa | 720 |
| aacctggctt ggtccagaag cagtgagctt gttgaagttt acaagcaaaa atgaagtcca | 780 |
| ggactatgtc agtgtagaat acctgcctcc ccacatgggt ggaactgatc ctttcaagta | 840 |
| tagctatcca ccactagtag atgatgactt ccagacccca ctgtgtgaga atgggcctat | 900 |
| taccagtgag gatgaaactt caagtaaaga agacatagaa agtgatggca agaaacatt | 960 |
| ggaaacaatt tctaatgaag aacaaacacc tcttcttaaa aagattaacc caaccgaatc | 1020 |
| tacttccaaa gcagaagaaa tgaaaaagt tgattcaaaa gtgaaagctt tcaagaaacc | 1080 |
| attgagtgta tttaaaggcc ccttactaca catcagccca gcagaagaac tgtactttgg | 1140 |
| aagtacagaa tccggagaga agaaaaacctt aatagtgttg acaaatgtaa ctaaaaatat | 1200 |
| agtggcattt aaggtgagaa caacagctcc agaaaaatac agagtcaagc caagcaatag | 1260 |
| cagctgtgac ccgggtgcat cagtggatat agttgtgtct ccccatgggg gtttaacagt | 1320 |
| ctctgcccaa gaccgttttc tgataatggc tgcagaaatg gaacagtcat ctggcacagg | 1380 |
| cccagcagaa ttaactcagt tttggaaaga agttcccaga aacaaagtga tggaacatag | 1440 |
| gttaagatgc catactgttg aaagcagtaa accaaacact cttacgttaa agacaatgc | 1500 |
| tttcaatatg tcagataaaa ccagtgaaga tatatgtcta caatttgcca cctccagctg | 1560 |
| tgaaatggac tgcagtccac cctaagtact gtgcacagta tctccctgtg tgtgtgcaca | 1620 |
| gtggcttccc cttacatggt agatttttgg ccttaatata atctaatccc aaagtagttg | 1680 |
| tgtatgtttt ctgttccttg gcaaataaat gaagaaataa ttagccaaga ttgaaaatgt | 1740 |
| attgtcctaa cggtgtccct ttaatgtttc atatgaaaaa ttatgttgac ccactaaaat | 1800 |
| atccttgctc aatgtctggt cagttgaatt taataacata tcttgttaat gtttgtgtgt | 1860 |
| ctattaaatg tgactaagca ggattactga aaattcacta taaaatcaaa ggcatctaaa | 1920 |
| cgtttgtact tgtcttgatt aatcatatat ttacacttga ttttttctg tcttcatttg | 1980 |

| | |
|---|---|
| tttttattta atcataattg catgatttttt ttggtactct aatcagtaat tttatttttta | 2040 |
| atcatgtcat tacctattca tgaccaaatt accaaggaac caacatttag atttagatat | 2100 |
| ttgtttttcac ttaggaatgg aaattaatag attttccatg aaagcattag tgaaatatca | 2160 |
| ttaccttgat ctgcaagtag cctaaaaatg cgattgctgg taaacctggc ctcaaatttc | 2220 |
| atactaccat aactgttttt atatattgcc actaattttg actggattta atagcacttt | 2280 |
| attgtacaac tacaaaaaaa aatatattcc tagaattgtt | 2320 |

<210> SEQ ID NO 33
<211> LENGTH: 3909
<212> TYPE: DNA
<213> ORGANISM: Artificial Sequence
<220> FEATURE:
<223> OTHER INFORMATION: Homo sapiens motile sperm domain containing 2
      (MOSPD2), transcript variant X2, mRNA

<400> SEQUENCE: 33

| | |
|---|---|
| accgcctccc cctcccaccc ttctctgtct acctctgggc gggactgccg ggtgatgaga | 60 |
| tactcggtcg gcgacggtag aacgggcgac ggcgacaacc gcaatcacat ccacgacggt | 120 |
| gatcatggca gagaatcacg cccagaataa agccaagctc atctctgaga cccggaggag | 180 |
| gttcgaagct gagtatgtga cagataagtc agataaatat gatgcacgtg atgttgaaag | 240 |
| gctacaacaa gatgataact gggttgaaag ttacttatct tggagacata atattgtaga | 300 |
| tgaaacactg aagatgctcg atgagagttt tcagtggagg aaagaaattt ctgtcaatga | 360 |
| ccttaatgaa tcctccattc ccagatggtt attggaaatt ggtgttattt atctccatgg | 420 |
| ttatgacaaa gaaggtaaca aattgttctg gatcagggtg aagtatcatg taaaagacca | 480 |
| gaaaaccata ttggacaaaa agaagctcat agcattctgg ttggaacgtt atgctaagag | 540 |
| ggaaaatggg aaacctgtaa cagtgatgtt tgacctgtca gaaactggaa taaatagcat | 600 |
| tgacatggac tttgtacgct ttatcatcaa ctgctttaag gtttattacc ctaaatacct | 660 |
| ctcaaaaata gtgatctttg atatgccttg gttaatgaat gctgctttca aaattgtgaa | 720 |
| aacctggctt ggtccagaag cagtgagctt gttgaagttt acaagcaaaa atgaagtcca | 780 |
| ggactatgtc agtgtagaat acctgcctcc ccacatgggt ggaactgatc cttcaagta | 840 |
| tagctatcca ccactagtag atgatgactt ccagacccca ctgtgtgaga atgggcctat | 900 |
| taccagtgag gatgaaactt caagtaaaga agacatagaa agtgatggca agaaacatt | 960 |
| ggaaacaatt tctaatgaag aacaaacacc tcttcttaaa aagattaacc caaccgaatc | 1020 |
| tacttccaaa gcaagaaaa atgaaaaagt tgattcaaaa gtgaaagctt caagaaacc | 1080 |
| attgagtgta tttaaaggcc ccttactaca catcagccca gcagaagaac tgtactttgg | 1140 |
| aagtacagaa tccggagaga agaaaacctt aatagtgttg acaaatgtaa ctaaaaatat | 1200 |
| agtggcattt aaggtgagaa caacagctcc agaaaaatac agagtcaagc caagcaatag | 1260 |
| cagctgtgac ccgggtgcat cagtggatat agttgtgtct ccccatgggg gtttaacagt | 1320 |
| ctctgcccaa gaccgttttc tgataatggc tgcagaaatg aacagtcat ctggcacagg | 1380 |
| cccagcagaa ttaactcagt tttggaaaga agttcccaga acaaagtga tggaacatag | 1440 |
| gttaagatgc catactgttg aaagcagtaa accaaacact cttacgttaa aagacaatgc | 1500 |
| tttcaatatg tcagataaaa ccagtgaaga tatatgtcta caatacagtt aaagaagtgg | 1560 |
| tgccgggtag gaaccacggt tccttcgtcc attagttgga aaaagtaaca gacctaaaac | 1620 |
| tctaccaagc tactaaaaac attgcacatc tgtgcttcct aaaaggaaat atgcagcacg | 1680 |

-continued

```
tggagggaa cacatacatg tcttgaaaat aaactgctag aataaagaaa tgctggagaa      1740
attgattata agagactata gctatttagt aaagtaagta aaggcatatc cattgtgtaa      1800
attaatagtt taaatataat ttattttttc cttttgatct gaatactttt aaagcttaag      1860
ttttatcgtg taaatacatt agctaaactg aaaagtataa gtaacatgct tgttgcagc       1920 caaaaatgt aatctgcttt tttatgacag aattattata gctgagctga cttactagct       1980
tttctatact atgtatatag aagaacatgt atattgagaa agaaaacata cttatataga      2040
ggaatttatg taaccatgac tttgtaattt tgagaattcc tcccagtgat ggtcagtatt      2100
cttttggaat gtaaaccgat ttaatgccaa accaccttaa cctttgtttc tcagtgttcc      2160
ttaacagcct gccttttatt aatctcaggc ttttttatga acactctcat ttcagtagaa      2220 tttgaaaac taagcgtggt tggaatttct ttgaattctg ttagtaatgc ccaaaagaaa       2280
agtctcaagc agtcccccta tccagtcatt tttatggagt ttcatgttgt ccactatagc     2340
tggacactga accttttgcc taatttatta aaaggcctg accctctatt gtcccatctt      2400 caccccatt ccagagcaga ggagtctctg tggaccatga attgcactgt ctccctcctc      2460
atttctaaat gaaaggtatt agatataaat ttttttgaaa ggttagttgt ttgagatgct     2520
aagcaggata taaatttag atttaaaat gttccctgta aaagtcagcc catgacaagg       2580
aaatttacaa aatactagag tatctagaag ggtgaaaaca aaaaaaaata aaaagaaaca     2640
cagacgccca ggtgtcagct ctccgtttaa agaatgaaaa atgtaactca tgatgatctg     2700
tgaaaccttc aaactaggac caattgactt acttgatatt ctgcctttga tatggtagta    2760
cccacccggt attcctaaaa tcctaaaaag atacaccttg cagtagcaga ggcaatgaca    2820
tgagtttgtt ttctcattaa tatgaccagt ttgggtctat gttggttcac atgtacatct    2880
actttatatg aaagaaaaaa cagttgtctg cctgtaaaat gttgagtttc gattgagcca    2940
tgtttggaga ttttattact attctgaagg gtagtgttgt tggttttcat cttcaagaag    3000
ttgattccaa aactgagtta tgaagaatga tataacagtt ccttcaaaat tggcctagga    3060
aataaaacct taaaaggaca ctggtgtgct actttgtctt aatttgggct tttctgtttc    3120
agtttgccac ctccagctgt gaaatggact gcagtccacc ctaagtactg tgcacagtat    3180
ctccctgtgt gtgtgcacag tggcttcccc ttacatggta gatttttggc cttaatataa    3240
tctaatccca aagtagttgt gtatgttttc tgttccttgg caaataaatg aagaaataat    3300
tagccaagat tgaaaatgta ttgtcctaac ggtgtccctt taatgtttca tatgaaaat     3360 tatgttgacc cactaaaata tccttgctca atgtctggtc agttgaattt aataacatat    3420
cttgttaatg tttgtgtgtc tattaaatgt gactaagcag gattactgaa aattcactat    3480
aaaatcaaag gcatctaaac gtttgtactt gtcttgatta atcatatatt tacacttgat    3540
ttttttctgt cttcatttgt tttttattaa tcataattgc atgatttttt tggtactcta    3600
atcagtaatt ttattttaa tcatgtcatt acctattcat gaccaaatta ccaaggaacc     3660
aacatttaga tttagatatt tgttttcact taggaatgga aattaataga ttttccatga    3720
aagcattagt gaaatatcat taccttgatc tgcaagtagc ctaaaaatgc gattgctggt    3780
aaacctggcc tcaaatttca tactaccata actgttttta tatattgcca ctaatttga    3840 ctggatttaa tagcactttta ttgtacaact acaaaaaaaa atatattcct agaattgttg   3900
ccagtgtaa                                                            3909
```